United States Patent
Hartz

(10) Patent No.: US 6,894,045 B2
(45) Date of Patent: May 17, 2005

(54) TETRAHYDROPURINONES AND DERIVATIVES THEREOF AS CORTICOTROPIN RELEASING FACTOR RECEPTOR LIGANDS

(75) Inventor: Richard A. Hartz, Kennett Square, PA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 212 days.

(21) Appl. No.: 10/192,061

(22) Filed: Jul. 10, 2002

(65) Prior Publication Data

US 2003/0149059 A1 Aug. 7, 2003

Related U.S. Application Data

(60) Provisional application No. 60/304,921, filed on Jul. 12, 2001.

(51) Int. Cl.$^7$ .................... C07D 473/30; A61K 31/522; A61P 25/24; A61P 25/22
(52) U.S. Cl. .................. 514/234.2; 514/263.2; 514/263.3; 514/263.22; 544/265; 544/276; 544/118
(58) Field of Search .................. 544/265, 276; 514/263.22, 263.2, 263.3

(56) References Cited

U.S. PATENT DOCUMENTS 6,004,966 A   12/1999 Singh
6,310,205 B1 * 10/2001 Chasin et al. ................ 544/276

FOREIGN PATENT DOCUMENTS

| EP | 0856310 | 8/1998 |
|---|---|---|
| WO | WO 95/10506 | 4/1995 |
| WO | WO 96/01761 | 1/1996 |
| WO | WO 97/35539 | 10/1997 |
| WO | WO 97/35846 | 10/1997 |
| WO | WO 97/44308 | 11/1997 |
| WO | WO 98/03510 | 1/1998 |
| WO | WO 99/01439 | 1/1999 |
| WO | WO 99/01454 | 1/1999 |
| WO | WO 99/11643 | 3/1999 |
| WO | WO 99/18707 | 4/1999 |
| WO | WO 99/51608 | 10/1999 |
| WO | WO 00/01675 | 1/2000 |
| WO | WO 02/19975 | 3/2002 |

OTHER PUBLICATIONS

J. Rivier et. al., Proc. Nat. Acad. Sci. (USA), 80:4851 (1983).
W. Vale et al., Science 213:1394 (1981).
W. Vale et al., Rec. Prog. Horm. Res. 39:245 (1983).
G.F. Koob, Persp. Behav. Med. 2:39 (1985).
E.D. De Souza et al., J. Neurosci. 5:3189 (1985).
J.E. Blalock, Physiological Reviews 69:1 (1989).
J.E. Morley, Life Sci. 41:527 (1987).
E.B. De Souza, Hosp. Practice 23:59 (1988).
C.B. Nemeroff et al., Science 226:1342 (1984).
C.M Banki et al., Am. J. Psychiatry 144:873 (1987).
R.D. France et al., Biol. Psychiatry 28:86 (1986).
M. Arato et al., Biol Psychiatry 25:355 (1989).
C.B. Nemeroff et al., Arch. Gen. Psychiatry 45:577 (1988).
P.W. Gold et al., Am J. Psychiatry 141:619 (1984).
F. Holsboer et al., Psychoneuroendocrinology 9:147 (1984).
P.W. Gold et al., New Eng. J. Med. 314:1129 (1986).
R.M. Sapolsky, Arch. Gen. Psychiatry 46:1047 (1989).
Grigoriadis et al., Neuropsychopharmacology 2:53 (1989).
D.R. Britton et al., Life Sci. 31:363 (1982).
C.W. Berridge and A.J. Dunn, Regul. Peptides 16:83 (1986).
C.W. Berridge and A.J. Dunn, Horm. Behav. 21:393 (1987).
Dunn, Brain Research Reviews 15:71 (1990).
K.T. Britton et al., Psychopharmacology 86:170 (1985).
K.T. Britton et al., Psychopharmacology 94:306 (1988).
N.R. Swerdlow et al., Psychopharmacology 88:147 (1986).
G.F. Koob and K.T. Britton, In: Corticotropin–Releasing Factor: Basic and Clinical Studies of a Neuropeptide, E.B. De Souza and C.B. Nemeroff eds., CRC press p221 (1990).
C. Maillot, M. Million, J.Y. Wei, A. Gauthier, Y. Tache, Gastroenterology, 119, 1569–1979 (2000).
J.R. McCarthy, S.C. Heinrichs and D.E. Grigoriadis, Cuur. Pharm. Res., 5, 289–315 (1999).
P.J. Gilligan, D.W. Robertson and R. Zaczek, J. Medicinal chem., 43, 1641–1660 (2000).
G.P. Chrousos, Int. J. Obesity, 24, Suppl. S50–S55 (2000).
E. webster, D.J. Torpy, I.J. Elenkov, G.P. Chrousos, Ann, N.Y. Acad. Sci., 840, 21–32 (1988).
D.J. Newport and C.B. Nemeroff, Curr. Opin. Neurobiology, 10, 211–218 (2000).
G. Mastorakos and I. Ilias, Ann N.Y. Acad. Sci., 900, 95–106 (2000).
M.J. Owens and C.B. Nemeroff, Expert Opin. Invest. Drugs, 8 1849–1858 (1999).
G.F. Koob, Ann N.Y. Acad. Sci., 909, 170–185 (2000).
Remington's Pharmaceutical Sciences, 17$^{th}$ ed., Mack Publishing Company, Easton, PA, 1985, p. 1418.
Wolfe, J.P.; Tomori, H.; Sadighi, J.P.; Yin, J.; Bushwald, S.L., J. Org. Chem. 2000, 65,1158–1174.

* cited by examiner

Primary Examiner—Mark L. Berch
(74) Attorney, Agent, or Firm—Shah R. Makujina; Christine A. Goddard; Woodcook Washburn LLP

(57) ABSTRACT

Compounds provided herein are novel substituted tetrahydropurinones of Formula (I):

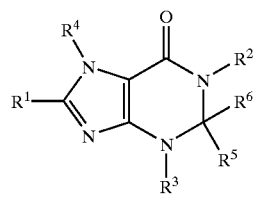

(I)

wherein $R^3$ is aryl substituted with 0–5 $X^{Ar}$ or heteroaryl substituted with 0–4 $X^{hAr}$. Such compounds are particularly useful as CRF receptor ligands, and hence, in the treatment of various neurologically-related disorders such as affective disorder, anxiety and depression.

27 Claims, No Drawings

TETRAHYDROPURINONES AND DERIVATIVES THEREOF AS CORTICOTROPIN RELEASING FACTOR RECEPTOR LIGANDS

CROSS-REFERENCE TO RELATED APPLICATIONS

This application claims the benefit of U.S. Provisional App. No. 60/304,921, filed Jul. 12, 2001, the disclosure of which is incorporated herein by reference in its entirety.

FIELD OF THE INVENTION

This invention relates to novel 1,2,3,7-tetrahydro-6H-purin-6-ones, pharmaceutical compositions containing the same, and methods of using the same in the treatment of psychiatric disorders and neurological diseases including affective disorder, anxiety related disorders, depression, headache, post-traumatic stress disorder, supranuclear palsy, Alzheimer's disease, head and spinal cord traumas, anorexia nervosa or other feeding disorders, as well as treatment of irritable bowel syndrome, gastrointestinal diseases, cardiovascular or heart-related diseases, immune supression, human immunodeficiency virus infections, fertility problems, or a disorder the treatment of which can be effected or facilitated by antagonizing CRF, including but not limited to disorders induced or facilitated by CRF.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebrospinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15–1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

It has been further postulated that CRF has a role in cardiovascular or heart-related diseases as well as gastrointestinal disorders arising from stress such as hypertension, tachycardia and congestive heart failure, stroke, irritable bowel syndrome post-operative ileus and colonic hypersensitivity associated with psychopathological disturbance and stress [for reviews see E. D. DeSouza, C. B. Nemeroff, Editors; Corticotropin-Releasing Factor: Basic and Clinical Studies of a Neuropeptide, E. B. De Souza and C. B. Nemeroff eds., CRC Press p221 (1990) and C. Maillot, M. Million, J. Y. Wei, A. Gauthier, Y. Tache, Gastroenterology, 119, 1569–1579 (2000)].

Over-expression or under-expression of CRF has been proposed as an underlying cause for several medical disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, postoperative ileus and colonic hypersensitivity associated with psychopathological disturbance and stress [for reviews see J. R. McCarthy, S. C. Heinrichs and D. E. Grigoriadis, Cuur. Pharm. Res., 5, 289–315 (1999); P. J. Gilligan, D. W. Robertson and R. Zaczek, J. Medicinal Chem., 43, 1641–1660 (2000), G. P. Chrousos, Int. J. Obesity, 24, Suppl. 2, S50–S55 (2000); E. Webster, D. J. Torpy, I. J. Elenkov, G. P. Chrousos, Ann. N.Y. Acad. Sci., 840, 21–32 (1998); D. J. Newport and C. B. Nemeroff, Curr. Opin. Neurobiology, 10, 211–218 (2000); G. Mastorakos and I. Ilias, Ann. N.Y. Acad. Sci., 900, 95–106 (2000); M. J. Owens and C. B. Nemeroff, Expert Opin. Invest. Drugs, 8, 1849–1858 (1999); G. F. Koob, Ann. N.Y. Acad. Sci., 909, 170–185 (2000)].

Further, studies have demonstrated that CRF-1 antagonists may be useful as hair growth stimulators. PCT publication WO 02/19975 discloses cell culture assays for the used of CRF antagonists in stimulating KBM-2 cell production. Thus, CRF antagonists may be useful in treatment of hair loss.

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; and, WO00/01675. Other bicyclic compounds have been reported in EP 856310; WO 96/1761; and U.S. Pat. No. 6,004,966.

SUMMARY OF THE INVENTION

The present invention provides classes of novel compounds which can function as CRF receptor ligands, including CRF antagonists. These compounds can be represented by Formula (I):

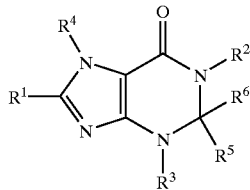

(I)

or a pharmaceutically acceptable salt form thereof, wherein $R^1$, $R^2$, $R^3$, $R^4$, $R^5$, $R^6$ are defined hereinbelow.

Also provided are pharmaceutical compositions comprising a compound of Formula (I) and a pharmaceutically acceptable carrier.

The present invention further provides methods of treating a mammal having a disorder characterized by hypersecretion or overexpression of corticotropin releasing factor comprising administering to the mammal a therapeutically effective amount of a compound of Formula (I). Some treatable disorders include affective disorder, anxiety, or depression.

DETAILED DESCRIPTION OF THE INVENTION

The present invention provides, inter alia, compounds having Formula (I):

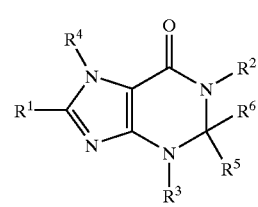

(I)

or pharmaceutically acceptable salt forms thereof, wherein:

$R^1$ is H, $C_1$–$C_4$ alkyl substituted with 0–3 $X^1$, $C_3$–$C_8$ cycloalkyl substituted with 0–3 $X^1$, $C_2$–$C_4$ alkenyl substituted with 0–3 $X^1$, or $C_2$–$C_4$ alkynyl substituted with 0–3 $X^1$;

each $X^1$ is, independently at each occurrence, CN, hydroxy, halo, or $C_1$–$C_4$ alkoxy;

alternatively, $R^1$ is CN, $C_1$–$C_4$ haloalkyl, $C_1$–$C_6$ alkyl-$NR^{1a}R^{1b}$, $NR^{1a}C(O)R^{1b}$, $C(O)NR^{1a}R^{1b}$, $OR^{1a}$, $S(O)_nR^{1a}$, or $OC(O)R^{1a}$;

each $R^{1a}$ and $R^{1b}$ is, independently, H, $C_1$–$C_4$ alkyl substituted with 0–3 $X^2$ or $C_3$–$C_6$ cycloalkyl substituted with 0–3 $X^2$;

each $X^2$ is, independently, at each occurrence, CN, hydroxy, halo, or $C_1$–$C_4$ alkoxy;

n is 0, 1 or 2;

$R^2$ is H, $C_1$–$C_6$ alkyl substituted with 0 to 4 $X^3$, $C_3$–$C_7$ cycloalkyl substituted with 0 to 4 $X^3$, $C_3$–$C_6$-cycloalkyl-$C_1$–$C_6$ alkyl substituted with 0 to 4 $X^3$, $C_3$–$C_6$-alkenyl substituted with 0 to 4 $X^3$, $C_3$–$C_6$-alkynyl substituted with 0 to 4 $X^3$, aryl substituted with 0 to 4 $X^3$, heteroaryl substituted with 0 to 4 $X^3$, or $C_5$–$C_8$ cycloalkenyl substituted with 0 to 4 $X^3$;

each $X^3$ is, independently at each occurrence, halogen, OH, $C_2$–$C_4$ alkenyl, $C_2$–$C_4$ alkynyl, $C_2$–$C_4$ cycloalkyl, $C_1$–$C_4$ haloalkyl, $CO_2R^7OC(O)R^7$, $COR^7$, $OC(O)OR^7$, $CO_2H$, $OR^7$, $NR^8R^9$, $NR^7COR^9$, $NHR^7SO_2R^9$, $OC(O)NR^7R^8$, $N(COR^7)_2$, $NR^7CONR^8R^9$, $NR^7CO_2R^9$, $CONR^7R^9$, $S(O)_nR^7$, $SO_2NR^7R^9$, SH, CN, aryl, heteroaryl, or heterocyclyl;

$R^3$ is aryl substituted with 0–5 $X^{Ar}$ or heteroaryl substituted with 0–4 $X^{hAr}$;

each $X^{Ar}$ is, independently at each occurrence, phenyl, $C_1$–$C_6$ alkyl, $C_3$–$C_6$ cycloalkyl, methylenedioxy, $C_1$–$C_4$ alkoxy-$C_1$–$C_4$ alkoxy, $OR^{15}$, Br, Cl, F, I, $C_1$–$C_4$ haloalkyl, CN, $NO_2$, SH, $S(O)_nR^{16}$, $COR^{15}$, $CO_2R^{15}$, $OC(O)R^{16}$, $NR^{20}COR^{15}$, $N(COR^{15})_2$, $NR^{20}CONR^{15}R^{17}$, $NR^{20}CO_2R^{16}$, $NR^{15}R^{17}$, or $CONR^{15}R^{17}$;

each $X^{hAr}$ is, independently at each occurrence, $C_1$–$C_6$ alkyl, $C_3$–$C_6$ cycloalkyl, Br, Cl, F, I, $C_1$–$C_4$ haloalkyl, CN, nitro, $OR^{15}$, SH, $S(O)_nR^{16}$, $COR^{15}$, $CO_2R^{15}$, $OC(O)R^{16}$, $NR^{20}COR^{15}$, $N(COR^{15})_2$, $NR^{20}CONR^{15}R^{17}$, $NR^{20}CO_2R^{16}$, $NR^{15}R^{17}$, $CONR^{15}R^{17}$, $R^{20}$, $CO_2R^{21}$, $COR^{21}$, or $SO_2R^{21}$;

$R^4$ is $C_1$–$C_{10}$ alkyl substituted with 0–1 $X^4$ or 0–3 $X^5$, $C_2$–$C_{10}$ alkenyl substituted with 0–1 $X^4$ or 0–3 $X^5$, $C_2$–$C_{10}$ alkynyl substituted with 0–1 $X^4$ or 0–3 $X^5$, $C_3$–$C_8$ cycloalkyl substituted with 0–1 $X^4$ or 0–3 $X^5$, $C_3$–$C_6$ cycloalkyl-$C_{1-6}$ alkyl substituted with 0–1 $X^4$ or 0–3 $X^5$, $C_1$–$C_4$ alkoxy-$C_{1-4}$ alkyl substituted with 0–1 $X^4$ or 0–3 $X^5$, aryl substituted with 0–1 $X^4$ or 0–3 $X^5$, heteroaryl substituted with 0–1 $X^4$ or 0–3 $X^5$, heterocyclyl substituted with 0–1 $X^4$ or 0–3 $X^5$, or aryl-$C_1$–$C_4$ alkyl substituted with 0–1 $X^5$ or 0–3 $X^5$;

each $X^4$ is, independently at each occurrence, CN, $S(O)_n R^{11}$, $COR^{12}$, $CO_2 R^{12}$, $NR^{13}COR^{12}$, $N(COR^{12})_2$, $NR^{13}CONR^{12}R^{14}$, $NR^{13}CO_2R^{11}$, $CONR^{12}R^{14}$, 1-naphthalenyl, 1-morpholinyl, 1-piperidinyl, 1-piperazinyl, or $C_{3-8}$ cycloalkyl, wherein 0–1 carbon atoms in said $C_{3-8}$ cycloalkyl is replaced by a group selected from the group consisting of —$S(O)_n$—, —$NR^{12}$—, —$NCO_2R^{11}$—, —$NCOR^{11}$—and —$NSO_2R^{11}$—, and wherein $N^4$ in 1-piperazinyl is substituted with 0–1 substituents selected from the group consisting of $R^{12}$, $CO_2R^{11}$, $COR^{11}$ and $SO_2R^{11}$;

each $X^5$ is, independently at each occurrence, aryl, heteroaryl, heterocyclyl, $C_1$–$C_6$ alkyl, $C_2$–$C_8$ alkenyl, $C_2$–$C_8$ alkynyl, Br, Cl, F, I, $C_{1-4}$ haloalkyl, $OR^{12}$, $NR^{12}R^{14}$, $C_1$–$C_4$ alkoxy-$C_1$–$C_4$ alkyl substituted with 0–1 $R^{10}$, or $C_3$–$C_8$ cycloalkyl optionally substituted with 0–1 $R^{10}$, and wherein 0–1 carbon atoms in said $C_3$–$C_8$ cycloalkyl is replaced by —O—;

each $R^5$ and $R^6$ is, independently, H, $C_1$–$C_4$ alkyl, $C_3$–$C_4$ alkenyl, or $C_3$–$C_4$ alkynyl;

each $R^7$ is, independently at each occurrence, H, $C_1$–$C_4$ alkyl substituted with 0–2 $X^6$, $C_3$–$C_6$ cycloalkyl substituted with 0–2 $X^6$, $C_3$–$C_4$ alkenyl substituted with 0–2 $X^6$, $C_3$–$C_4$ alkynyl substituted with 0–2 $X^6$, $C_1$–$C_4$ haloalkyl substituted with 0–2 $X^6$, $C_1$–$C_4$ alkyloxy-$C_1$–$C_4$ alkyl substituted with 0–2 $X^6$, or $C_3$–$C_6$ cycloalkyl-$C_1$–$C_4$ alkyl substituted with 0–2 $X^6$, wherein one carbon atom in any cycloalkyl ring is optionally replaced with O, S or $NR^8$;

each $X^6$ is, independently at each occurrence, OH, $C_1$–$C_4$ alkoxy, or halogen;

$R^8$ is H, $C_1$–$C_4$ alkyl, $C_3$–$C_6$ cycloalkyl, $C_3$–$C_6$ cycloalkyl-$C_1$–$C_4$ alkyl, or $C_1$–$C_4$ haloalkyl;

$R^9$ is H, $C_1$–$C_4$ alkyl substituted with 0–2 $X^7$, $C_3$–$C_6$ cycloalkyl substituted with 0–2 $X^7$, $C_3$–$C_4$ alkenyl substituted with 0–2 $X^7$, $C_3$–$C_4$ alkynyl substituted with 0–2 $X^7$, $C_1$–$C_4$ haloalkyl substituted with 0–2 $X^7$, aryl substituted with 0–2 $X^7$, $C_1$–$C_4$ alkyloxy-$C_1$–$C_4$ alkyl substituted with 0–2 $X^7$, or $C_3$–$C_6$ cycloalkyl-$C_1$–$C_4$ alkyl substituted with 0–2 $X^7$, wherein one carbon in any cycloalkyl ring is optionally replaced with O, S or $NR^8$;

each $X^7$ is, independently at each occurrence, $C_1$–$C_4$ alkoxy or halogen;

$R^{10}$ is H, $C_1$–$C_4$ alkyl, $C_3$–$C_6$ cycloalkyl-$C_1$–$C_4$ alkyl, or $C_3$–$C_8$ cycloalkyl;

$R^{11}$ is $C_1$–$C_4$ alkyl, $C_1$–$C_4$ haloalkyl, $C_1$–$C_4$ alkoxy-$C_1$–$C_4$ alkyl, $C_3$–$C_6$ cycloalkyl, or $C_3$–$C_6$ cycloalkyl-$C_{1-6}$ alkyl;

$R^{12}$ is H, benzyl, aryl, $C_1$–$C_4$ alkyl, $C_1$–$C_4$ haloalkyl, $C_1$–$C_4$ alkoxy-$C_1$–$C_4$ alkyl, $C_3$–$C_6$ cycloalkyl, or $C_3$–$C_6$ cycloalkyl-$C_{1-6}$ alkyl;

$R^{13}$ is H, $C_1$–$C_4$ alkyl, $C_3$–$C_7$ cycloalkyl, or $C_3$–$C_6$ cycloalkyl-$C_1$–$C_6$ alkyl;

$R^{14}$ is H, $C_1$–$C_4$ alkyl, $C_1$–$C_4$ haloalkyl, $C_1$–$C_4$ alkoxy-$C_1$–$C_4$ alkyl, $C_3$–$C_6$ cycloalkyl, or $C_3$–$C_6$ cycloalkyl-$C_1$–$C_6$ alkyl;

$R^{15}$ is H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-4}$ alkyl, $C_{1-4}$ haloalkyl, $R^{18}S(O)_n$—$C_{1-4}$ alkyl, or $R^{11}R^{12}N$—$C_{2-4}$ alkyl;

each $R^{16}$ and $R^{17}$ is, independently at each occurrence, H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, or $C_{1-4}$ haloalkyl;

alternatively, in an $NR^{15}R^{17}$ moiety, $R^{15}$ and $R^{17}$ are taken together with the nitrogen atom to which they are both attached to form 1-pyrrolidinyl, 1-morpholinyl, 1-piperidinyl, or 1-piperazinyl, wherein $N^4$ in 1-piperazinyl is substituted with 0–1 substituents selected from the group consisting of $R^{19}$, $CO_2R^{18}$, $COR^{18}$ and $SO_2R^{18}$;

$R^{18}$ is $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl-$C_{1-4}$ alkyl, heteroaryl, or heteroaryl-$C_{1-4}$ alkyl, wherein said aryl-$C_{1-4}$ alkyl is substituted with 0–1 substituents selected from the group consisting of $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{19}$ is H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl-$C_{1-4}$ alkyl, heteroaryl, or heteroaryl-$C_{1-4}$ alkyl;

$R^{20}$ is H, $C_{1-4}$ alkyl, $C_{3-7}$ cycloalkyl, $C_{3-6}$ cycloalkyl-$C_{1-6}$ alkyl, aryl substituted with 0–3 $X^8$, or aryl-$C_1$–$C_4$ alkyl substituted with 0–3 $X^8$;

each $X^8$ is, independently at each occurrence, $C_{1-4}$ alkyl, Br, Cl, F, I, $C_{1-4}$ haloalkyl, nitro, $C_{1-4}$ alkoxy, $C_{1-4}$ haloalkoxy, or dimethylamino;

$R^{21}$ is $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, or aryl-$C_1$–$C_4$ alkyl, wherein said aryl-$C_1$–$C_4$ alkyl is substituted with 0–1 $X^9$; and each $X^9$ is, independently at each occurrence, $C_{1-4}$ alkyl, Br, Cl, F, I, $C_{1-4}$ haloalkyl, nitro, $C_{1-4}$ alkoxy, $C_{1-4}$ haloalkoxy, or dimethylamino.

According to some embodiments, $R^1$ can be $C_1$–$C_4$ alkyl, $C_3$–$C_8$ cycloalkyl, $C_2$–$C_4$ alkenyl, or $C_2$–$C_4$ alkynyl, while in other embodiments $R^1$ can be $OR^{1a}$ and $R^{1a}$ can be $C_1$–$C_4$ alkyl.

Some further first embodiments include compounds of Formula (I) where $R^2$ is $C_1$–$C_6$ alkyl or $C_3$–$C_7$ cycloalkyl. Additionally, in some embodiments, $R^3$ is phenyl, naphthyl, indanyl, or indenyl, each of which can substituted with 0–5 $X^{Ar}$. In other embodiments, $R^3$ is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl, or benzodioxane, each of which can be substituted with 0–4 $X^{hAr}$. In further embodiments, $R^3$ is phenyl substituted with 0–5 $X^{Ar}$ or pyridyl substituted with 0–4 $X^{hAr}$. In some compounds of the Formula (I), $R^4$ is $C_1$–$C_{10}$ alkyl, $C_3$–$C_8$ cycloalkyl, or benzyl. Additionally, each $R^5$ and $R^6$ can be, independently, H or $C_1$–$C_4$ alkyl.

In further embodiments, the present invention provides compounds of Formula (I) or pharmaceutically acceptable salt forms thereof, wherein:

$R^1$ is $C_1$–$C_4$ alkyl substituted with 0–3 $X^1$, $C_3$–$C_8$ cycloalkyl substituted with 0–3 $X^1$, $C_2$–$C_4$ alkenyl substituted with 0–3 $X^1$, $C_2$–$C_4$ alkynyl substituted with 0–3 $X^1$, $C_1$–$C_4$ haloalkyl, CN, $OR^{1a}$, or $S(O)_n R^{1a}$;

$R^2$ is $C_1$–$C_6$ alkyl substituted with 0 to 4 $X^3$, $C_3$–$C_7$ cycloalkyl substituted with 0 to 4 $X^3$, $C_3$–$C_6$-alkenyl substituted with 0 to 4 $X^3$, or $C_3$–$C_6$-alkynyl substituted with 0 to 4 $X^3$;

each $X^3$ is, independently at each occurrence, halogen, OH, $C_2$–$C_4$ alkenyl, $C_2$–$C_4$ alkynyl, $C_2$–$C_4$ cycloalkyl, $C_1$–$C_4$ haloalkyl, $CO_2R^7OC(O)R^7$, $COR^7$, $OC(O)OR^7$, $CO_2H$, $OR^7$, $NR^8R^9$, $NR^7COR^9$, $NHR^7SO_2R^9$, $OC(O)NR^7R^8$, $N(COR^7)_2$, $NR^7CONR^8R^9$, $NR^7CO_2R^9$, $CONR^7R^9$, $S(O)_nR^7$, $SO_2NR^7R^9$, SH, or CN;

$R^3$ is phenyl substituted with 0–5 $X^{Ar}$ or pyridyl substituted with 0–4 $X^{hAr}$;

$R^4$ is $C_1$–$C_{10}$ alkyl substituted with 0–1 $X^4$ or 0–3 $X^5$; $C_2$–$C_{10}$ alkenyl substituted with 0–1 $X^4$ or 0–3 $X^5$; $C_2$–$C_{10}$ alkynyl substituted with 0–1 $X^4$ or 0–3 $X^5$; $C_3$–$C_8$ cycloalkyl substituted with 0–1 $X^4$ or 0–3 $X^5$, or aryl-$C_1$–$C_4$ alkyl substituted with 0–1 $X^4$ or 0–3 $X^5$;

each $X^4$ is, independently at each occurrence, CN, $S(O)_nR^{11}$, $CO_2R^{12}$, or 1-naphthalenyl;

each $X^5$ is, independently at each occurrence, aryl, $C_1$–$C_6$ alkyl, $C_2$–$C_8$ alkenyl, $C_1$–$C_4$ haloalkyl, $OR^{12}$, $NR^{12}R^{14}$, $C_1$–$C_4$ alkoxy-$C_{1-4}$ alkyl substituted with 0–1 $R^{10}$, or $C_3$–$C_8$ cycloalkyl optionally substituted with 0–1 $R^{10}$, and wherein 0–1 carbon atoms in said $C_3$–$C_8$ cycloalkyl is replaced by —O—; and each $R^5$ and $R^6$ is, independently, H or $C_1$–$C_4$ alkyl. Remaining substituents are defined as provided hereinabove.

In other embodiments, the present invention further provides compounds of Formula (I) or pharmaceutically acceptable salt forms thereof, wherein:

$R^1$ is $C_1$–$C_4$ alkyl, CN, $C_1$–$C_4$ haloalkyl, or $OR^{1a}$;

$R^{1a}$ is $C_1$–$C_4$ alkyl substituted with 0–3 halo;

$R^2$ is $C_1$–$C_6$ alkyl substituted with 0 to 4 $X^3$ or $C_3$–$C_7$ cycloalkyl substituted with 0 to 4 $X^3$;

$R^3$ is phenyl substituted with 0–5 $X^{Ar}$ or pyridyl substituted with 0–4 $X^{hAr}$;

$R^4$ is $C_1$–$C_{10}$ alkyl substituted with O-1 $X^4$ or 0–3 $X^5$; $C_2$–$C_{10}$ alkenyl substituted with 0–1 $X^4$ or 0–3 $X^5$; $C_2$–$C_{10}$ alkynyl substituted with 0–1 $X^4$ or 0–3 $X^5$; $C_3$–$C_8$ cycloalkyl substituted with 0–1 $X^4$ or 0–3 $X^5$, or aryl-$C_1$–$C_4$ alkyl substituted with 0–1 $X^4$ or 0–3 $X^5$; and each $R^5$ and $R^6$ is, independently, H or $C_1$–$C_4$ alkyl. Remaining variables can be defined as provided hereinabove.

According to some of such embodiments, $R^3$ can be phenyl substituted with 0–3 $X^{Ar}$ or pyridyl substituted with 0–2 $X^{hAr}$. Further, according to such embodiments, $X^{Ar}$ can be selected from phenyl, $C_1$–$C_6$ alkyl (such as, e.g., methyl, ethyl, or propyl), $OR^{15}$ (such as, e.g., methoxy, ethoxy, or $OCF_3$), Br, Cl, F, I, or $C_1$–$C_4$ haloalkyl (such as, e.g., $CF_3$). In still other of such embodiments, $X^{hAr}$ can be selected from $C_1$–$C_6$ alkyl (such as, e.g., methyl, ethyl, or propyl), $C_3$–$C_6$ cycloalkyl (such as, e.g., cyclopropyl, cyclobutyl, or cyclopentyl), Br, Cl, F, I, $C_1$–$C_4$ haloalkyl (such as, e.g., $CF_3$), CN, or $OR^{15}$ (such as, e.g., methoxy, ethoxy, or $OCF_3$). In still further of such embodiments, $R^4$ is substituted by 0–1 $X^4$ and $X^4$ is 1-naphthalenyl.

The present invention further provides for compounds of of Formula (I) or pharmaceutically acceptable salt forms thereof, wherein:

$R^1$ is methyl, ethyl, methoxy, ethoxy, $CF_3$, or CN;

$R^2$ is methyl, ethyl, propyl, butyl, pentyl, cyclopropyl, cyclobutyl, cyclopentyl, cyclohexyl, or cycloheptyl;

$R^3$ is phenyl substituted with 0–4 $X^{Ar}$ or pyridyl substituted with 0–3 $X^{hAr}$;

each $X^{Ar}$ is, independently at each occurrence, methyl, ethyl, propyl, butyl, methoxy, ethoxy, $CF_3$, $OCF_3$, CN, Br, Cl, F, or I;

each $X^{hAr}$ is, independently at each occurrence, methyl, ethyl, propyl, butyl, methoxy, ethoxy, $CF_3$, $OCF_3$, CN, Br, Cl, F, or I;

$R^4$ is methyl, ethyl, propyl, butyl, pentyl, hexyl, heptyl, cyclopropyl, cyclobutyl, cyclopentyl, cyclohexyl, cycloheptyl, ethenyl, propenyl, butenyl, or benzyl, wherein $R^4$ is optionally substituted with one 1-naphthalenyl group;

alternatively, $R^4$ is substituted with 0–3 substituents independently selected from phenyl, methyl, ethyl, propyl, butyl, pentyl, hexyl, cyclopropyl, cyclobutyl, cyclopentyl, cyclohexyl, cycloheptyl, $CF^3$, $OCF^3$, ethenyl, propenyl, methoxy, ethoxy, propoxy, butoxy, benzyloxy; and each $R^5$ and $R^6$ is, independently, H, methyl, or ethyl.

In some of such embodiments, $R^1$ can be ethyl or methoxy, and in further of such embodiments, $R^2$ can be methyl.

The present invention further provides the following compounds:

3-(2,4-dichlorophenyl)-8-ethyl-1-methyl-7-(3-pentyl)-1,2,3,7-tetrahydro-6H-purin-6-one;

3-(2,4-dichlorophenyl)-8-ethyl-7-(4-heptyl)-1-methyl-1,2,3,7-tetrahydro-6H-purin-6-one;

3-(2,4-dichlorophenyl)-1,2-dimethyl-8-ethyl-7-(3-pentyl)-1,2,3,7-tetrahydro-6H-purin-6-one;

3-(2,4-dichlorophenyl)-2,8-diethyl-1-methyl-7-(3-pentyl)-1,2,3,7-tetrahydro-6H-purin-6-one;

3-(2,4-dichlorophenyl)-1,2-dimethyl-8-ethyl-7-(4-heptyl)-1,2,3,7-tetrahydro-6H-purin-6-one;

3-(2,4-dichlorophenyl)-2,8-diethyl-7-(4-heptyl)-1-methyl-1,2,3,7-tetrahydro-6H-purin-6-one;

7-[benzyloxymethyl]-3-(2,4-dichlorophenyl)-8-ethyl-1-methyl-1,2,3,7-tetrahydro-6H-purin-6-one;

3-(2,4-dichlorophenyl)-8-ethyl-7-[1-(methoxymethyl)butyl]-1-methyl-1,2,3,7-tetrahydro-6H-purin-6-one;

3-(2,4-dichlorophenyl)-8-ethyl-1-methyl-7-[1-(2-propenyl)-3-butenyl]-1,2,3,7-tetrahydro-6H-purin-6-one;

3-(2,4-dichlorophenyl)-1-methyl-7-(3-pentyl)-1,2,3,7-tetrahydro-6H-purin-6-one;

3-(2,4-dichlorophenyl)-7-(4-heptyl)-1-methyl-1,2,3,7-tetrahydro-6H-purin-6-one;

3-(2,4-dichlorophenyl)-8-ethyl-7-[(4-methoxyphenyl)methyl]-1-methyl-1,2,3,7-tetrahydro-6H-purin-6-one;

3-(2,4-dichlorophenyl)-7-dicyclopropylmethyl-8-ethyl-1-methyl-1,2,3,7-tetrahydro-6H-purin-6-one;

3-(2,4-dichlorophenyl)-8-ethyl-1-methyl-7-(2-pentyl)-1,2,3,7-tetrahydro-6H-purin-6-one;

3-(2,4-dichlorophenyl)-8-ethyl-1-methyl-7-[(2-methylphenyl)methyl]-1,2,3,7-tetrahydro-6H-purin-6-one;

3-(2,4-dichlorophenyl)-8-ethyl-1-methyl-7-(1-naphthalenylmethyl)-1,2,3,7-tetrahydro-6H-purin-6-one;

3-(2,4-dichlorophenyl)-8-ethyl-7-[3-methoxy-1-(2-methoxyethyl)propyl]-1-methyl-1,2,3,7-tetrahydro-6H-purin-6-one;

7-(1-cyclopropylethyl)-3-(2,4-dichlorophenyl)-8-ethyl-1-methyl-1,2,3,7-tetrahydro-6H-purin-6-one;

7-(1-cyclopropylpropyl)-3-(2,4-dichlorophenyl)-8-ethyl-1-methyl-1,2,3,7-tetrahydro-6H-purin-6-one;

7-(1-cyclopropylbutyl)-3-(2,4-dichlorophenyl)-8-ethyl-1-methyl-1,2,3,7-tetrahydro-6H-purin-6-one;

7-([1,1'-biphenyl]-4-ylmethyl)-3-(2,4-dichlorophenyl)-8-ethyl-1-methyl-1,2,3,7-tetrahydro-6H-purin-6-one;

3-(2,4-dichlorophenyl)-8-ethyl-7-(3-heptyl)-1-methyl-1,2,3,7-tetrahydro-6H-purin-6-one;

3-(2-chloro-4-methoxyphenyl)-8-ethyl-1-methyl-7-(3-pentyl)-1,2,3,7-tetrahydro-6H-purin-6-one;

3-(2-chloro-4-methoxyphenyl)-8-ethyl-7-(4-heptyl)-1-methyl-1,2,3,7-tetrahydro-6H-purin-6-one;

3-(2-chloro-4-methoxyphenyl)-8-ethyl-1-methyl-7-(2-pentyl)-1,2,3,7-tetrahydro-6H-purin-6-one;

3-(2-chloro-4-methoxyphenyl)-8-ethyl-7-[1-(methoxymethyl)butyl]-1-methyl-1,2,3,7-tetrahydro-6H-purin-6-one;

3-(2-chloro-4-methoxyphenyl)-7-(1-cyclopropylpropyl)-8-ethyl-1-methyl-1,2,3,7-tetrahydro-6H-purin-6-one;

7-([1,1'-biphenyl]-4-ylmethyl)-3-(2-chloro-4-methoxyphenyl)-8-ethyl-1-methyl-1,2,3,7-tetrahydro-6H-purin-6-one;

3-(2-chloro-4-methoxyphenyl)-8-ethyl-1-methyl-7-[(2-methylphenyl)methyl]-1,2,3,7-tetrahydro-6H-purin-6-one;

3-(2-chloro-4-methoxyphenyl)-7-(1-cyclopropylbutyl)-8-ethyl-1-methyl-1,2,3,7-tetrahydro-6H-purin-6-one;

3-(2-chloro-4-methoxyphenyl)-7-(1-cyclobutylethyl)-8-ethyl-1-methyl-1,2,3,7-tetrahydro-6H-purin-6-one;

3-[2-chloro-4-isopropylphenyl]-8-ethyl-7-(4-heptyl)-1-methyl-1,2,3,7-tetrahydro-6H-purin-6-one;

3-[2-chloro-4-isopropylphenyl]-8-ethyl-7-(1-ethyl-2-methylpropyl)-1-methyl-1,2,3,7-tetrahydro-6H-purin-6-one;

8-ethyl-7-(4-heptyl)-1-methyl-3-(2,4,6-trimethylphenyl)-1,2,3,7-tetrahydro-6H-purin-6-one;

8-ethyl-7-(1-ethyl-2-methylpropyl)-1-methyl-3-(2,4,6-trimethylphenyl)-1,2,3,7-tetrahydro-6H-purin-6-one; and 8-ethyl-7-(4-heptyl)-3-(4-methoxy-2-methylpyrid-3-yl)-1-methyl-1,2,3,7-tetrahydro-6H-purin-6-one.

3-(2-chloro-4-methoxyphenyl)-8-ethyl-7-(3-heptyl)-1-methyl-1,2,3,7-tetrahydro-6H-purin-6-one;

3-[2-chloro-4-isopropylphenyl]-8-ethyl-7-(3-heptyl)-1-methyl-1,2,3,7-tetrahydro-6H-purin-6-one;

8-ethyl-7-(3-heptyl)-3-(4-methoxy-2-methylpyrid-3-yl)-1-methyl-1,2,3,7-tetrahydro-6H-purin-6-one;

8-ethyl-7-(3-heptyl)-1-methyl-3-(2,4,6-trimethylphenyl)-1,2,3,7-tetrahydro-6H-purin-6-one;

3-(2-chloro-5-fluoro-4-methoxyphenyl)-8-ethyl-7-(4-heptyl)-1-methyl-1,2,3,7-tetrahydro-6H-purin-6-one;

3-(2-chloro-5-fluoro-4-methoxyphenyl)-8-ethyl-7-(3-heptyl)-1-methyl-1,2,3,7-tetrahydro-6H-purin-6-one;

8-ethyl-3-(5-fluoro-4-methoxy-2-methylphenyl)-7-(4-heptyl)-1-methyl-1,2,3,7-tetrahydro-6H-purin-6-one;

8-ethyl-3-(5-fluoro-4-methoxy-2-methylphenyl)-7-(3-heptyl)-1-methyl-1,2,3,7-tetrahydro-6H-purin-6-one;

3-(2-chloro-4,5-dimethoxyphenyl)-8-ethyl-7-(4-heptyl)-1-methyl-1,2,3,7-tetrahydro-6H-purin-6-one;

3-(2-chloro-4,5-dimethoxyphenyl)-8-ethyl-7-(3-heptyl)-1-methyl-1,2,3,7-tetrahydro-6H-purin-6-one;

3-(2,4-dimethylphenyl)-8-ethyl-7-(4-heptyl)-1-methyl-1,2,3,7-tetrahydro-6H-purin-6-one;

3-(2,4-dimethoxyphenyl)-8-ethyl-7-(4-heptyl)-1-methyl-1,2,3,7-tetrahydro-6H-purin-6-one; and 3-(2,4-dimethylpyrid-3-yl)-8-ethyl-7-(4-heptyl)-1-methyl-1,2,3,7-tetrahydro-6H-purin-6-one.

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" as used herein is meant to refer to a saturated hydrocarbon group (designated by the formula $C_nH_{2+n}$ which is straight-chained or branched. Alkyl groups can be unsubstituted or substituted so that one or more of its hydrogens are replaced by another chemical group. Example alkyl groups include methyl (Me), ethyl (Et). propyl (e.g., n-propyl and isopropyl), butyl (e.g., n-butyl, isobutyl, t-butyl), pentyl (n-pentyl, isopentyl, neopentyl), and the like. "Alkenyltm" refers to hydrocarbon chains of either a straight-chained or branched configuration having one or more unsaturated carbon-carbon bonds. Example alkenyl groups include ethenyl, propenyl, and the like. "Alkynyl" refers to hydrocarbon chains of either a straight-chained or branched configuration having one or more triple carbon-carbon bonds. Example alkynyl groups include ethynyl, propynyl, and the like. "Haloalkyl" refers to branched and straight-chained alkyl groups having one or more halogen substituents. Example haloalkyl groups include $CF_3$, $C_2F_5$, $CHF_2$, $CH_2F$, $CCl_3$, $CHCl_2$, $CH_2Cl$, and the like. The term "alkoxy" refers to an —O-alkyl group. Example alkoxy groups include, methoxy, ethoxy, t-butoxy, and the like. The term "cycloalkyl" refers to cyclized alkyl groups, including mono- ,bi- or poly-cyclic ring systems. Example cycloalkyl groups include cyclopropyl, cyclobutyl, cyclopentyl, cyclohexyl, norbornyl, and so forth. "Halo" or whalogen includes fluoro, chioro, bromo, and iodo.

"Aryl" groups refer to monocyclic or polycyclic aromatic hydrocarbons, including, for example, phenyl, naphthyl, anthracenyl, phenanthrenyl, indanyl, indenyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubsituted.

"Heteroaryl" groups are monocyclic and polycyclic aromatic hydrocarbons that include at least one heteroatom ring member, such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, indolinyl, benzodioxolanyl, benzodioxanyl, and the like. Heteroaryl groups can be substituted or unsubsituted.

"Heterocyclyl" groups are saturated or partially saturated heteroaryl groups. Hetterocyclyl groups can be substituted or unsubstituted. Examples of heterocyclyl groups include piperazinyl, tetrahydrofuranyl, tetrahydrothienyl, piperidinyl, pyrrolidinyl, isoxazolidinyl, isothiazolidiriyl, pyrazolidinyl, oxazolidinyl. thiazolidiriyl, imidazolidinyl, and the like. Some example heteroaryl substituents can include $C_1$–$C_4$ alkyl, $C_3$–$C_6$ cycloalkyl, $C_2$–$C_6$ alkenyl, $C_2$–$C_6$, alkynyl, halogen, $C_1$–$C_4$ haloalkyl, CN, OR, SH, $NO_2$, $OCF_3$, $S(O)_nR^7$, $COR^7$, $CO_2R^7$, $OC(O)R^7$, $NR^3COR^8$, $N(COR^7)_2$, $NR^3CONR^7R^8$, $NR^7CO_2R^8$, $NR^7R^8$, or $CONR^7R^8$.

"Substituted" means that one or more hydrogen on the designated atom is replaced with a selection from the indicated group, provided that the designated atom's normal valency is not exceeded, and that the substitution results in a stable compound.

"Unsubstituted" atoms bear all of the hydrogen atoms dictated by their valency. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically acceptable salt forms of compounds provided herein can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples or prodrugs include, but are not limited to, acetate, formate and benzoate derivatives of alcohol and amine functional groups in the compounds of Formula (I), and the like.

The term "therapeutically effective amount" of a compound of this invention refers to an amount effective to reduce or eliminate the undesirable symptoms associated with abnormal levels, such as elevated levels due to hypersecretion, of CRF in a host.

The novel compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques in this section. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of Formula (I) are prepared by the method outlined in Scheme 1. An appropriately substituted aryl or heteroaryl isocyanate (3) is treated with a primary alkylamine in a suitable solvent, such as THF, to form ureas of formula 4. The ureas of formula 4 are dissolved in acetic anhydride and treated with cyanoactic acid. Subsequent treatment with a base such as aqueous NaOH results in the formation of uricils of formula 5. Nitrosation of intermediate 5 with a reagent, such as $NaNO_2$, and subsequent reduction with a suitable reagent, such as $Na_2S_2O_4$, affords the corresponding diamines (7). Appropriate cyclization conditions, such as the use of orthoesters, yields compounds of formula 8. Compounds of Formula (I) can be derived from compounds of formula 8 by treatment of 8 with a suitable base such as, but not limited to, NaH, KH, $K_2CO_3$, $Na_2CO_3$, i-$Pr_2$NEt, NaOMe, NaOEt and $Et_3$N and a suitable alkylating agent $R_4$X such as, but not limited to, alkyl halides, tosylates, mesylates and triflates in a suitable inert solvent such as, but not limited to, DMF, THF, $CH_2Cl_2$, dioxane, toluene and DMSO. Compounds of Formula (I) can also be derived from compounds of formula 8 by treatment of 8 with an alcohol $R_4$OH, a phosphine $PR^a{}_3$ (where $R^a$ is lower alkyl, phenyl or substituted phenyl or furyl) and an azodicarboxylate ester $R^bO_2CN=NCO_2R^b$ (where $R^b$ is lower alkyl) in an inert solvent at temperatures ranging from 0° C. to 150° C. Inert solvent may include but is not limited to polyethers (preferably 1,2-dimethoxyethane), dialkyl ethers (preferably diethylether), cyclic ethers (preferably tetrahydrofuran or 1,4-dioxane) or aromatic hydrocarbons (preferably benzene or toluene). The choices of phosphine, solvent or azodicarboxylate ester are known to those skilled in the art of organic chemistry as described by Mitsunobu (Mitsunobu, O. *Synthesis* 1981, 1).

SCHEME 1

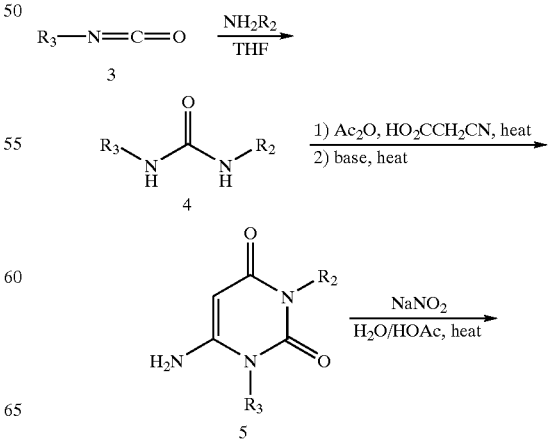

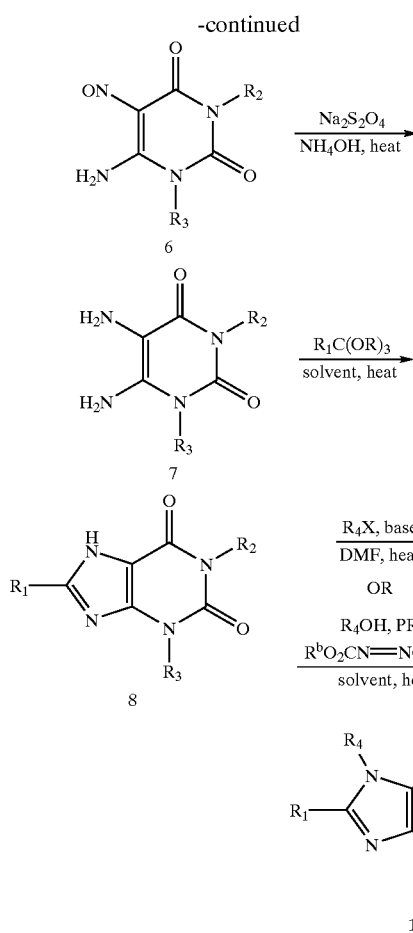

For some of the examples, the aryl or heteroaryl $R_3$ substituent can be functionalized further by treatment with reagents known to one skilled in the art of organic synthesis (for example, N-bromosuccinimide, bromine, N-chlorosuccinimide, alkyl halides, acid chlorides, etc., preferably N-chlorosuccinimide) (Scheme 2).

SCHEME 2

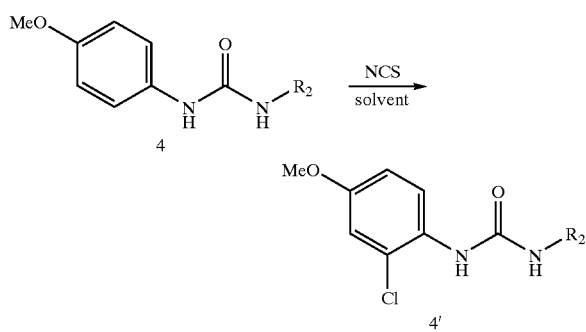

A series of compounds of formula 2 are prepared by the methods outlined in Schemes 3, 4 or 5. A compound of Formula (I) (preparation illustrated in Scheme 1) is treated with a base, such as, but not limited to, NaOMe, NaOEt, NaOH or KOH in a solvent, such as, but not limited to, lower alcoholic solvents, $H_2O$, THF, dioxane or organic amines (preferably ethanol/$H_2O$) at temperatures ranging from 20° C. to 120° C. Alternatively, a compound of Formula (I) is treated with a reducing agent such as, but not limited to, $NaBH_4$, $LiBH_4$, $LiAlH_4$, $BH_3$, or DIBAL (preferably $LiBH_4$ or $LiAlH_4$) in a polar aprotic solvent such as, but not limited to, $CH_2Cl_2$, THF or dioxane at temperatures ranging from −78° C. to 120° C. The resulting intermediate 9 is treated with either an aldehyde, ketone, acetal or ketal and an acid catalyst and is heated between 25° C. to 150° C. to afford a compound of formula 2. Aldehydes, ketones, acetals and ketals may include, but are not limited to, formaldehyde, paraformaldehyde, lower alkyl aldehydes, acetone, lower alkyl ketones, lower alkyl acetals, or lower alkyl ketals ($R_c=C_1-C_6$ alkyl and may be joined together to form a ring). Acid catalysts may include, but are not limited to, p-toluenesulfonic acid and salts thereof as well as resin bound sulfonic acids (e.g. amberlyst, Dowex resin) (preferably p-toluenesulfonic acid).

SCHEME 3

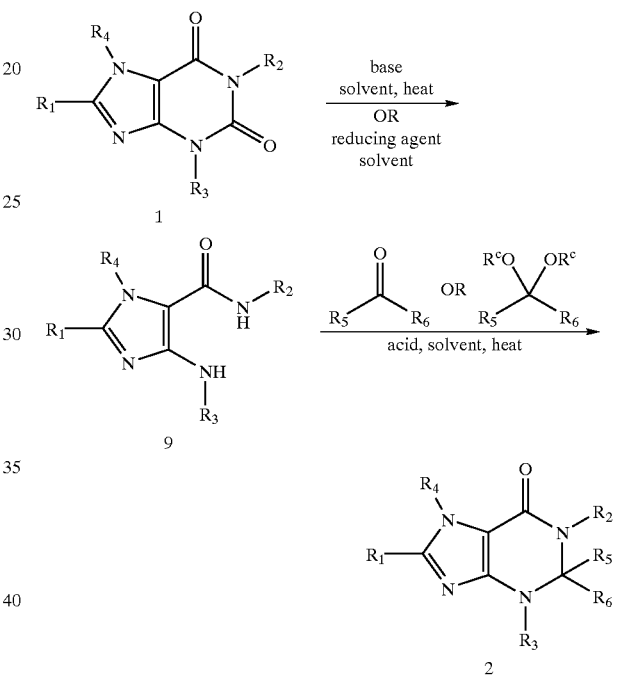

As stated above, a series of compounds of formula 2 are also prepared by the method outlined in Scheme 4. The imidazole nitrogen of a compound of formula 8 is protected with an appropriate protecting group reagent as described in *Protective Groups in Organic Synthesis* (Greene, Wuts; 3rd ed., 1999, John Wiley & Sons, Inc.), preferably benzyloxymethyl chloride. The reaction is carried out in the presence of tetrabutylammonium iodide and an appropriate base, such as $K_2CO_3$, in a suitable inert solvent, such as DMF. Preferred reaction temperatures range from 25° C. to 150° C. A compound of formula 10 is treated with a base such as, but not limited to, NaOMe, NaOEt, NaOH or KOH in a solvent such as, but not limited to, lower alcoholic solvents, H O, THF, dioxane or organic amines (preferably ethanol/$H_2O$) at temperatures ranging from 20° C. to 120° C. Alternatively, a compound of formula 10 is treated with a reducing agent such as, but not limited to, $NaBH_4$, $LiBH_4$, $LiAlH_4$, $BH_3$, or DIBAL (preferably $LiBH_4$ or $LiAlH_4$) in a polar aprotic solvent such as, but not limited to, $CH_2Cl_2$, THF or dioxane at temperatures ranging from −78° C. to 120° C. The resulting product 11 is treated with an aldehyde, ketone, acetal, or ketal and an acid catalyst and is heated between 25° C. to 150° C. to afford intermediate 12.

Aldehydes, ketones, acetals and ketals may include, but are not limited to, formaldehyde, paraformaldehyde, lower alkyl aldehydes, acetone, lower alkyl ketones, lower alkyl acetals, or lower alkyl ketals ($R^c=C_1-C_6$ alkyl and may be joined together to form a ring). Acid catalysts may include, but are not limited to, p-toluenesulfonic acid and salts thereof as well as resin bound sulfonic acids (e.g. amberlyst, Dowex resin) (preferably p-toluenesulfonic acid). Intermediate 12 is treated with an appropriate acid such as, but not limited to, triflouroacetic acid in the presence or absence of solvent to remove the protecting group. Preferred reaction temperatures range from 0° C. to 150° C.

Compounds of formula 2 can be derived from compounds of formula 13 by treatment of 13 with a suitable base such as, but not limited to, NaH, KH, $K_2CO_3$, $Na_2CO_3$, i-$Pr_2$NEt, NaOMe, NaOEt and $Et_3$N and a suitable alkylating agent $R_4$X such as, but not limited to, alkyl halides, tosylates, mesylates and triflates in a suitable inert solvent such as, but not limited to, DMF, THF, $CH_2Cl_2$, dioxane, toluene and DMSO. Compounds of formula 2 can also be derived from compounds of formula 13 by treatment of 13 with an alcohol $R_4$OH, a phosphine $PR^a_3$ (where $R^a$ is lower alkyl, phenyl or substituted phenyl or furyl) and an azodicarboxylate ester $R^bO_2CN=NCO_2R^b$ (where $R^b$ is lower alkyl) in an inert solvent at temperatures ranging from 0° C. to 150° C. Inert solvent may include but are not limited to polyethers (preferably 1,2-dimethoxyethane), dialkyl ethers (preferably diethylether), cyclic ethers (preferably tetrahydrofuran or 1,4-dioxane) or aromatic hydrocarbons (preferably benzene or toluene). The choices of phosphine, solvent or azodicarboxylate ester are known to those skilled in the art of organic chemistry as described by Mitsunobu (Mitsunobu, O. *Synthesis* 1981, 1).

SCHEME 4

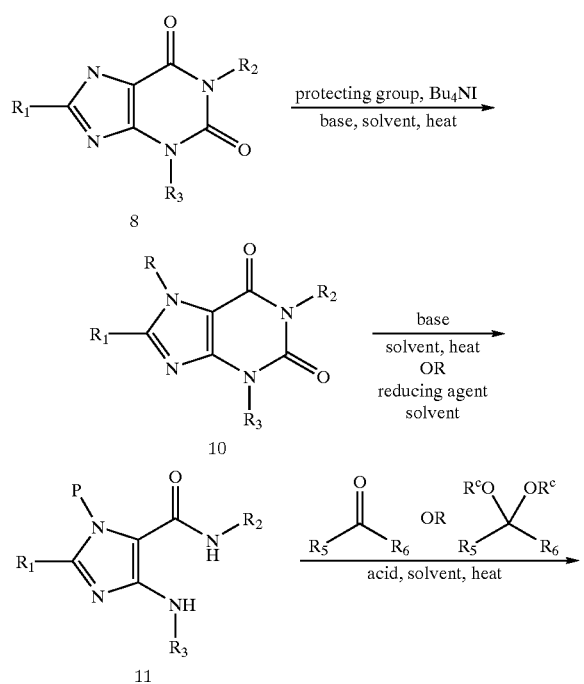

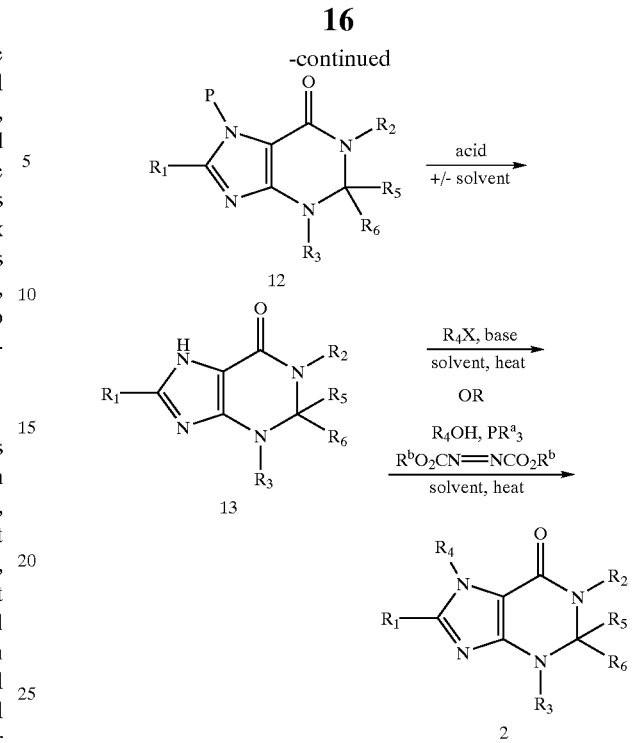

As stated above, a series of compounds of formula 2 are also prepared by the method outlined in Scheme 5. A compound of formula 14 is prepared using the route outlined in Scheme 1 where P is a protecting group which can be removed using conditions under which the other functional groups of the compound are stable. The protecting group, preferably p-methoxybenzyl, is removed using conditions described in *Protective Groups in Organic Synthesis* (Greene, Wuts; 3$^{rd}$ ed., 1999, John Wiley & Sons, Inc.), preferably by heating in trifluoroacetic acid at temperatures ranging from 25° C. to 150° C. to provide intermediate 15. If the reaction temperature exceeds the boiling point of trifluoroacetic acid, the reaction must be carried out in a pressure tube. Intermediate 15 is coupled with aryl or heteroarylboronic acids using conditions described by Lam et. al. (Lam, P. Y. S.; Clarck, C. G.; Saubern, S.; Adams, J.; Averill, K. M.; Chan, D. M. T.; Combs, A. *Synlett.* 2000, 5, 674.) to form the corresponding compound of Formula (I). The compound of Formula (I) is treated with a base such as, but not limited to, NaOMe, NaOEt, NaOH or KOH in a solvent such as, but not limited to, lower alcoholic solvents, $H_2O$, THF, dioxane or organic amines (preferably ethanol/$H_2O$) at temperatures ranging from 20° C. to 120° C. Alternatively, a compound of Formula (I) is treated with a reducing agent such as, but not limited to, $NaBH_4$ $LiBH_4$, $LiAlH_4$, $BH_3$, or DIBAL (preferably $LiBH_4$ or $LiAlH_4$) in a polar aprotic solvent such as, but not limited to, $CH_2Cl_2$, THF, or dioxane at temperatures ranging from −78° C. to 120° C. The resulting intermediate 9 is treated with an aldehyde, ketone, acetal, or ketal and an acid catalyst and is heated between 25° C. to 150° C. to afford a compound of formula 2. Aldehydes, ketones, acetals and ketals may include, but are not limited to, formaldehyde, paraformaldehyde, lower alkyl aldehydes, acetone, lower alkyl ketones, lower alkyl acetals, or lower alkyl ketals ($R=C_1-C_6$ alkyl and may be joined together to form a ring). Acid catalysts may include, but are not limited to p-toluenesulfonic acid and salts thereof as well as resin bound sulfonic acids (e.g. amberlyst, Dowex resin) (preferably p-toluenesulfonic acid).

SCHEME 5

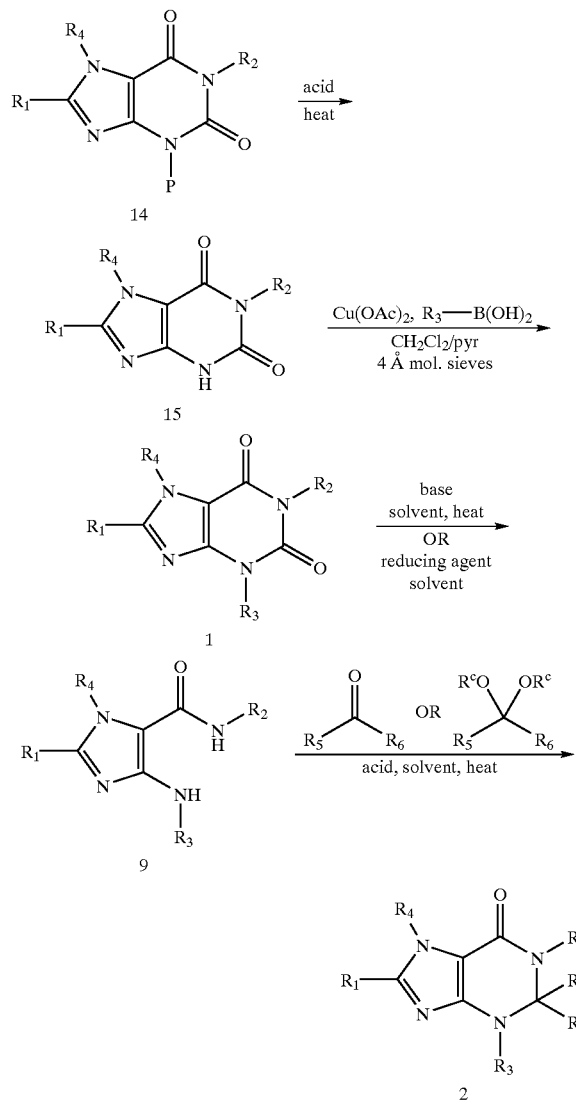

A series of compounds of formula 2 may also be prepared by the method outlined in Scheme 6. A compound of formula 16 may be treated with a brominating agent, such as bromine, in the presence of a base, such as potassium bicarbonate, in a solvent, such as DMF, to form the corresponding intermediate dibromide 17. The resulting imidazole 17 may be protected with an appropriate protecting group reagent as described in *Protective Groups in Organic Synthesis* (Greene, Wuts; 3$^{rd}$ ed., 1999, John Wiley & Sons, Inc.), preferably benzyloxymethyl chloride. The reaction is carried out in the presence of tetrabutylammonium iodide and an appropriate base, such as $K_2CO_3$, in a suitable inert solvent, such as DMF. Preferred reaction temperatures range from 25° C. to 150° C. A compound of formula 18 may then be treated with an alkyl lithium base, such as n-BuLi or t-BuLi and an acylating agent, such as methyl chloroformate, in a solvent, such as THF, at temperatures ranging from −90° C.–25° C. to form a compound of formula 19. A compound of formula 19 may then be treated with an aniline ($R_3$—$NH_2$) in the presence of a palladium catalyst, a trialkylphosphine catalyst, and sodium butoxide in a solvent such as toluene using reaction conditions described by Wolfe et. al. (Wolfe, J. P.; Tomori, H.; Sadighi, J. P.; Yin, J.; Buchwald, S. L. *J. Org. Chem.* 2000, 65, 1158–1174) to form a compound of formula 20. A compound of formula 20 may then be converted to the amide using typical conditions for ester hydrolysis and amide formation. The reaction may be carried out in the presence of $R_2NH_2$, in the presence or absence of a Lewis acid, such as but not limited to, trimethylaluminum, in a solvent suitable for the reaction conditions, and at temperatures ranging from 0° C. to 150° C. to form a compound of formula 11. The resulting product of formula 11 may be treated with an aldehyde, ketone, acetal, or ketal and an acid catalyst and is heated between 25° C. to 150° C. to afford a compound of formula 12. Aldehydes, ketones, acetals and ketals may include, but are not limited to, formaldehyde, paraformaldehyde, lower alkyl aldehydes, acetone, lower alkyl ketones, lower alkyl acetals, or lower alkyl ketals ($R^c=C_1–C_6$ alkyl and may be joined together to form a ring). Acid catalysts may include, but are not limited to, p-toluenesulfonic acid and salts thereof as well as resin bound sulfonic acids (e.g. amberlyst, Dowex resin) (preferably p-toluenesulfonic acid). Compound 12 may be treated with an appropriate acid such as, but not limited to, triflouroacetic acid in the presence or absence of solvent to remove the protecting group. Preferred reaction temperatures range from 0° C. to 150° C.

Compounds of formula 2 may be derived from compounds of formula 13 by treatment of 13 with a suitable base such as, but not limited to, NaH, KH, $K_2CO_3$, $Na_2CO_3$, i-$Pr_2NEt$, NaOMe, NaOEt and $Et_3N$ and a suitable alkylating agent $R_4X$ such as, but not limited to, alkyl halides, tosylates, mesylates, and triflates in a suitable inert solvent such as, but not limited to, DMF, THF, $CH_2Cl_2$, dioxane, toluene, and DMSO. Compounds of formula 2 may also be derived from compounds of formula 13 by treatment of 13 with an alcohol $R_4OH$, a phosphine $PR^a{}_3$ (where $R^a$ is lower alkyl, phenyl or substituted phenyl or furyl) and an azodicarboxylate ester $R^bO_2CN=NCO_2R^b$ (where $R^b$ is lower alkyl) in an inert solvent at temperatures ranging from 0° C. to 150° C. Inert solvents may include, but are not limited to, polyethers (preferably 1,2-dimethoxyethane), dialkyl ethers (preferably diethylether), cyclic ethers (preferably tetrahydrofuran or 1,4-dioxane) or aromatic hydrocarbons (preferably benzene or toluene). The choices of phosphine, solvent, or azodicarboxylate ester are known to those skilled in the art of organic chemistry as described by Mitsunobu (Mitsunobu, O. *Synthesis* 1981, 1).

SCHEME 6

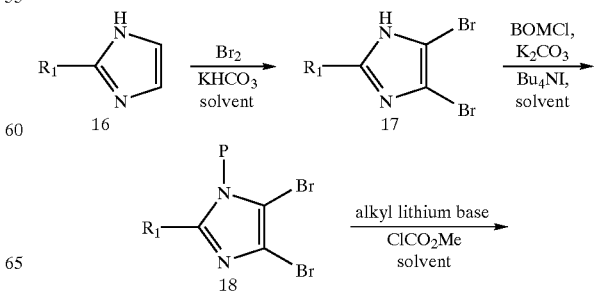

-continued

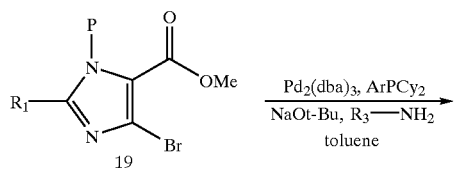

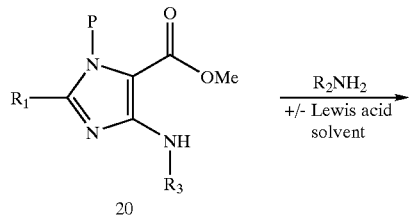

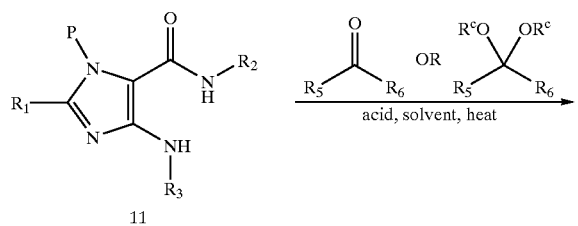

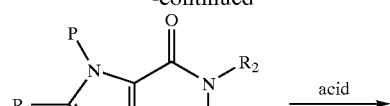

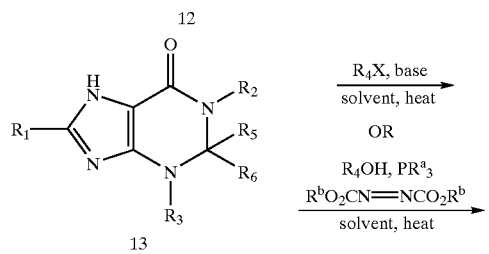

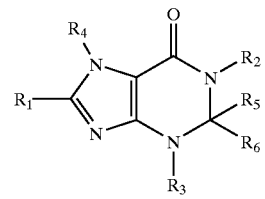

Various analogs synthesized using Schemes 1–5 are listed in Table 1.

TABLE 1

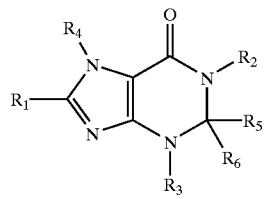

| EX | R$_1$ | R$_2$ | R$_3$ | R$_4$ | R$_5$ | R$_6$ | MP (° C.) |
|---|---|---|---|---|---|---|---|
| 1 | Et | Me | 2,4-Cl$_2$-Ph | 3-pentyl | H | H | 132–133 |
| 2 | Et | Me | 2,4-Cl$_2$-Ph | 4-heptyl | H | H | 117–118 |
| 3 | Et | Me | 2,4-Cl$_2$-Ph | 3-pentyl | Me | H | 135–136.5 |
| 4 | Et | Me | 2,4-Cl$_2$-Ph | 3-pentyl | Et | H | oil |
| 5 | Et | Me | 2,4-Cl$_2$-Ph | 4-heptyl | Me | H | 144–145.5 |
| 6 | Et | Me | 2,4-Cl$_2$-Ph | 4-heptyl | Et | H | 116.5–117.5 |
| 7 | Et | Me | 2,4-Cl$_2$-Ph | benzyloxymethyl | H | H | Amorph solid |
| 8 | Et | Me | 2,4-Cl$_2$-Ph | CH(CH$_2$OMe)Pr | H | H | oil |
| 9 | Et | Me | 2,4-Cl$_2$-Ph | CH(CH$_2$CH=CH$_2$)$_2$ | H | H | oil |
| 10 | H | Me | 2,4-Cl$_2$-Ph | 3-pentyl | H | H | oil |
| 11 | H | Me | 2,4-Cl$_2$-Ph | 4-heptyl | H | H | oil |
| 12 | Et | Me | 2,4-Cl$_2$-Ph | (4-methoxy-phenyl)methyl | H | H | 116.5–117.5 |
| 13 | Et | Me | 2,4-Cl$_2$-Ph | dicyclopropylmethyl | H | H | oil |
| 14 | Et | Me | 2,4-Cl$_2$-Ph | 2-pentyl | H | H | oil |
| 15 | Et | Me | 2,4-Cl$_2$-Ph | (2-methyl-phenyl)methyl | H | H | oil |
| 16 | Et | Me | 2,4-Cl$_2$-Ph | 1-naphthalenylmethyl | H | H | oil |
| 17 | Et | Me | 2,4-Cl$_2$-Ph | CH(CH$_2$CH$_2$OCH$_3$)$_2$ | H | H | oil |
| 18 | Et | Me | 2,4-Cl$_2$-Ph | 1-cyclopropylethyl | H | H | oil |
| 19 | Et | Me | 2,4-Cl$_2$-Ph | 1-cyclopropylpropyl | H | H | oil |
| 20 | Et | Me | 2,4-Cl$_2$-Ph | 1-cyclopropylbutyl | H | H | oil |
| 21 | Et | Me | 2,4-Cl$_2$-Ph | [1,1'-biphenyl]-4-ylmethylylmethyl | H | H | 216–217 |
| 22 | Et | Me | 2,4-Cl$_2$-Ph | CH(CH$_2$OMe)Et | H | H | |
| 23 | Et | Me | 2,4-Cl$_2$-Ph | CH(CH$_2$OMe)Me | H | H | |
| 24 | Et | Me | 2,4-Cl$_2$-Ph | CH(CH$_2$OMe)$_2$ | H | H | |
| 25 | Et | Me | 2,4-Cl$_2$-Ph | 1-cyclobutylethyl | H | H | |
| 26 | Et | Me | 2,4-Cl$_2$-Ph | 1-cyclobutylpropyl | H | H | |
| 27 | Et | Me | 2,4-Cl$_2$-Ph | CH(cBu)CH$_2$OMe | H | H | |
| 28 | Et | Me | 2,4-Cl$_2$-Ph | 1-cyclopentylethyl | H | H | |

TABLE 1-continued

| EX | R₁ | R₂ | R₃ | R₄ | R₅ | R₆ | MP (° C.) |
|---|---|---|---|---|---|---|---|
| 29 | Et | Me | 2,4-Cl₂-Ph | 1-cyclopentylpropyl | H | H | |
| 30 | Et | Me | 2,4-Cl₂-Ph | CH(cPentyl)CH₂OMe | H | H | |
| 31 | Et | Me | 2,4-Cl₂-Ph | CHOMePr | H | H | |
| 32 | Et | Me | 2,4-Cl₂-Ph | cyclobutyl | H | H | |
| 33 | Et | Me | 2,4-Cl₂-Ph | cyclopentyl | H | H | |
| 34 | Et | Me | 2,4-Cl₂-Ph | CH(Et)CH₂OH | H | H | |
| 35 | Et | Me | 2,4-Cl₂-Ph | R-2-pentyl | H | H | |
| 36 | Et | Me | 2,4-Cl₂-Ph | S-2-pentyl | H | H | |
| 37 | Et | Me | 2,4-Cl₂-Ph | R-3-heptyl | H | H | |
| 38 | Et | Me | 2,4-Cl₂-Ph | S-3-heptyl | H | H | |
| 39 | Et | Me | 2,4-Cl₂-Ph | CH(Et)CH₂NMe₂ | H | H | |
| 40 | Et | Me | 2,4-Cl₂-Ph | CH(Pr)CH₂NMe₂ | H | H | |
| 41 | Et | Me | 2,4-Cl₂-Ph | dicyclobutylmethyl | H | H | |
| 42 | Et | Me | 2,4-Cl₂-Ph | dicyclopentylmethyl | H | H | |
| 43 | Et | Me | 2,4-Cl₂-Ph | 1-cyclobutylbutyl | H | H | |
| 44 | Et | Me | 2,4-Cl₂-Ph | CH(cPr)CH₂OMe | H | H | |
| 45 | Et | Me | 2,4-Cl₂-Ph | CH(i-Pr)Et | H | H | |
| 46 | Et | Me | 2,4-Cl₂-Ph | CH(i-Pr)Pr | H | H | |
| 47 | Et | Me | 2,4-Cl₂-Ph | CH(i-Pr)CH₂OMe | H | H | |
| 48 | Et | Me | 2,4-Cl₂-Ph | CH(Et)Pr | H | H | |
| 49 | Et | Me | 2,4-Cl₂-Ph | 3-heptyl | H | H | 94–95 |
| 50 | OMe | Me | 2,4-Cl₂-Ph | 3-pentyl | H | H | |
| 51 | OMe | Me | 2,4-Cl₂-Ph | 4-heptyl | H | H | |
| 52 | OMe | Me | 2,4-Cl₂-Ph | CH(CH₂OMe)Et | H | H | |
| 53 | OMe | Me | 2,4-Cl₂-Ph | CH(CH₂OMe)Pr | H | H | |
| 54 | Et | Et | 2,4-Cl₂-Ph | 3-pentyl | H | H | |
| 55 | Et | Et | 2,4-Cl₂-Ph | 4-heptyl | H | H | |
| 56 | Et | Et | 2,4-Cl₂-Ph | CH(CH₂OMe)Et | H | H | |
| 57 | Et | Et | 2,4-Cl₂-Ph | CH(CH₂OMe)Pr | H | H | |
| 58 | Et | Pr | 2,4-Cl₂-Ph | 3-pentyl | H | H | |
| 59 | Et | Pr | 2,4-Cl₂-Ph | 4-heptyl | H | H | |
| 60 | Et | Pr | 2,4-Cl₂-Ph | CH(CH₂OMe)Et | H | H | |
| 61 | Et | Pr | 2,4-Cl₂-Ph | CH(CH₂OMe)Pr | H | H | |
| 62 | Et | cPr | 2,4-Cl₂-Ph | 3-pentyl | H | H | |
| 63 | Et | cPr | 2,4-Cl₂-Ph | 4-heptyl | H | H | |
| 64 | Et | cPr | 2,4-Cl₂-Ph | CH(CH₂OMe)Et | H | H | |
| 65 | Et | cPr | 2,4-Cl₂-Ph | CH(CH₂OMe)Pr | H | H | |
| 66 | Et | Pr | 2,4-Cl₂-Ph | 3-pentyl | H | H | |
| 67 | Et | Pr | 2,4-Cl₂-Ph | 4-heptyl | H | H | |
| 68 | Et | Pr | 2,4-Cl₂-Ph | CH(CH₂OMe)Et | H | H | |
| 69 | Et | Pr | 2,4-Cl₂-Ph | CH(CH₂OMe)Pr | H | H | |
| 70 | Et | Me | 2-Cl-4-OMe-Ph | 3-pentyl | H | H | oil |
| 71 | Et | Me | 2-Cl-4-OMe-Ph | 4-heptyl | H | H | oil |
| 72 | Et | Me | 2-Cl-4-OMe-Ph | 2-pentyl | H | H | oil |
| 73 | Et | Me | 2-Cl-4-OMe-Ph | CH(CH₂OMe)Pr | H | H | oil |
| 74 | Et | Me | 2-Cl-4-OMe-Ph | 1-cyclopropylpropyl | H | H | oil |
| 75 | Et | Me | 2-Cl-4-OMe-Ph | [1,1'-biphenyl]-4-ylmethyl | H | H | amorph solid |
| 76 | Et | Me | 2-Cl-4-OMe-Ph | dicyclopropylmethyl | H | H | |
| 77 | Et | Me | 2-Cl-4-OMe-Ph | (2-methyl-phenyl)methyl | H | H | oil |
| 78 | Et | Me | 2-Cl-4-OMe-Ph | 1-naphthalenylmethyl | H | H | |
| 79 | Et | Me | 2-Cl-4-OMe-Ph | CH(CH₂CH₂OCH₃)₂ | H | H | |
| 80 | Et | Me | 2-Cl-4-OMe-Ph | 1-cyclopropylethyl | H | H | |
| 81 | Et | Me | 2-Cl-4-OMe-Ph | 1-cyclopropylbutyl | H | H | oil |
| 82 | Et | Me | 2-Cl-4-OMe-Ph | CH(CH₂OMe)Et | H | H | |
| 83 | Et | Me | 2-Cl-4-OMe-Ph | CH(CH₂OMe)Me | H | H | |
| 84 | Et | Me | 2-Cl-4-OMe-Ph | CH(CH₂OMe)₂ | H | H | |
| 85 | Et | Me | 2-Cl-4-OMe-Ph | 1-cyclobutylethyl | H | H | oil |
| 86 | Et | Me | 2-Cl-4-OMe-Ph | 1-cyclobutylpropyl | H | H | |
| 87 | Et | Me | 2-Cl-4-OMe-Ph | CH(cBu)CH₂OMe | H | H | |
| 88 | Et | Me | 2-Cl-4-OMe-Ph | 1-cyclopentylethyl | H | H | |
| 89 | Et | Me | 2-Cl-4-OMe-Ph | 1-cyclopentylpropyl | H | H | |
| 90 | Et | Me | 2-Cl-4-OMe-Ph | CH(cPentyl)CH₂OMe | H | H | |
| 91 | Et | Me | 2-Cl-4-OMe-Ph | CHOMePr | H | H | |
| 92 | Et | Me | 2-Cl-4-OMe-Ph | cyclobutyl | H | H | |
| 93 | Et | Me | 2-Cl-4-OMe-Ph | cyclopentyl | H | H | |
| 94 | Et | Me | 2-Cl-4-OMe-Ph | CH(Et)CH₂OH | H | H | |

TABLE 1-continued

| EX | R₁ | R₂ | R₃ | R₄ | R₅ | R₆ | MP (° C.) |
|---|---|---|---|---|---|---|---|
| 95 | Et | Me | 2-Cl-4-OMe-Ph | R-2-pentyl | H | H | |
| 96 | Et | Me | 2-Cl-4-OMe-Ph | S-2-pentyl | H | H | |
| 97 | Et | Me | 2-Cl-4-OMe-Ph | R-3-heptyl | H | H | |
| 98 | Et | Me | 2-Cl-4-OMe-Ph | S-3-heptyl | H | H | |
| 99 | Et | Me | 2-Cl-4-OMe-Ph | CH(Et)CH₂NMe₂ | H | H | |
| 100 | Et | Me | 2-Cl-4-OMe-Ph | CH(Pr)CH₂NMe₂ | H | H | |
| 101 | Et | Me | 2-Cl-4-OMe-Ph | dicyclobutylmethyl | H | H | |
| 102 | Et | Me | 2-Cl-4-OMe-Ph | dicyclopentylmethyl | H | H | |
| 103 | Et | Me | 2-Cl-4-OMe-Ph | CH(CH₂CH=CH₂)₂ | H | H | |
| 104 | Et | Me | 2-Cl-4-OMe-Ph | CH(Et)Pr | H | H | |
| 105 | Et | Me | 2-Cl-4-OMe-Ph | CH(i-Pr)Et | H | H | |
| 106 | Et | Me | 2-Cl-4-OMe-Ph | CH(i-Pr)Pr | H | H | |
| 107 | Et | Me | 2-Cl-4-OMe-Ph | CH(i-Pr)CH₂OMe | H | H | |
| 108 | Et | Me | 2-Cl-4-OMe-Ph | 1-cyclobutylbutyl | H | H | |
| 109 | Et | Me | 2-Cl-4-OMe-Ph | CH(cBu)CH₂OMe | H | H | |
| 110 | Et | Me | 2-Cl-4-OMe-Ph | CH(cPr)CH₂OMe | H | H | |
| 111 | Et | cPr | 2-Cl-4-OMe-Ph | 3-pentyl | H | H | |
| 112 | Et | cPr | 2-Cl-4-OMe-Ph | 4-heptyl | H | H | |
| 113 | Et | cPr | 2-Cl-4-OMe-Ph | CH(CH₂OMe)Et | H | H | |
| 114 | Et | cPr | 2-Cl-4-OMe-Ph | CH(CH₂OMe)Pr | H | H | |
| 115 | Et | Me | 2-Cl-4-i-Pr-Ph | 3-pentyl | H | H | |
| 116 | Et | Me | 2-Cl-4-i-Pr-Ph | 4-heptyl | H | H | oil |
| 117 | Et | Me | 2-Cl-4-i-Pr-Ph | 2-pentyl | H | H | |
| 118 | Et | Me | 2-Cl-4-i-Pr-Ph | CH(CH₂OMe)Pr | H | H | |
| 119 | Et | Me | 2-Cl-4-i-Pr-Ph | 1-cyclopropylpropyl | H | H | |
| 120 | Et | Me | 2-Cl-4-i-Pr-Ph | 3-heptyl | H | H | |
| 121 | Et | Me | 2-Cl-4-i-Pr-Ph | dicyclopropylmethyl | H | H | |
| 122 | Et | Me | 2-Cl-4-i-Pr-Ph | 2-methylbenzyl | H | H | |
| 123 | Et | Me | 2-Cl-4-i-Pr-Ph | CH(CH₂CH₂OCH₃)₂ | H | H | |
| 124 | Et | Me | 2-Cl-4-i-Pr-Ph | 1-cyclopropylethyl | H | H | |
| 125 | Et | Me | 2-Cl-4-i-Pr-Ph | 1-cyclopropylbutyl | H | H | |
| 126 | Et | Me | 2-Cl-4-i-Pr-Ph | CH(CH₂OMe)Et | H | H | |
| 127 | Et | Me | 2-Cl-4-i-Pr-Ph | CH(CH₂OMe)Me | H | H | |
| 128 | Et | Me | 2-Cl-4-i-Pr-Ph | CH(CH₂OMe)₂ | H | H | |
| 129 | Et | Me | 2-Cl-4-i-Pr-Ph | 1-cyclobutylethyl | H | H | |
| 130 | Et | Me | 2-Cl-4-i-Pr-Ph | 1-cyclobutylpropyl | H | H | |
| 131 | Et | Me | 2-Cl-4-i-Pr-Ph | CH(CH₂CH=CH₂)₂ | H | H | |
| 132 | Et | Me | 2-Cl-4-i-Pr-Ph | CH(Et)Pr | H | H | |
| 133 | Et | Me | 2-Cl-4-i-Pr-Ph | CH(i-Pr)Et | H | H | oil |
| 134 | Et | Me | 2-Cl-4-i-Pr-Ph | CH(i-Pr)Pr | H | H | |
| 135 | Et | Me | 2-Cl-4-i-Pr-Ph | CH(i-Pr)CH₂OMe | H | H | |
| 136 | Et | Me | 2-Cl-4-i-Pr-Ph | 1-cyclobutylbutyl | H | H | |
| 137 | Et | Me | 2-Cl-4-i-Pr-Ph | CH(cBu)CH₂OMe | H | H | |
| 138 | Et | Me | 2-Cl-4-i-Pr-Ph | CH(cPr)CH₂OMe | H | H | |
| 139 | Et | cPr | 2-Cl-4-i-Pr-Ph | 3-pentyl | H | H | |
| 140 | Et | cPr | 2-Cl-4-i-Pr-Ph | 4-heptyl | H | H | |
| 141 | Et | cPr | 2-Cl-4-i-Pr-Ph | CH(CH₂OMe)Et | H | H | |
| 142 | Et | cPr | 2-Cl-4-i-Pr-Ph | CH(CH₂OMe)Pr | H | H | |
| 143 | Et | Me | 2,4,6-Me₃-Ph | 3-pentyl | H | H | |
| 144 | Et | Me | 2,4,6-Me₃-Ph | 4-heptyl | H | H | oil |
| 145 | Et | Me | 2,4,6-Me₃-Ph | 2-pentyl | H | H | |
| 146 | Et | Me | 2,4,6-Me₃-Ph | CH(CH₂OMe)Pr | H | H | |
| 147 | Et | Me | 2,4,6-Me₃-Ph | 1-cyclopropylpropyl | H | H | |
| 148 | Et | Me | 2,4,6-Me₃-Ph | 3-heptyl | H | H | |
| 149 | Et | Me | 2,4,6-Me₃-Ph | dicyclopropylmethyl | H | H | |
| 150 | Et | Me | 2,4,6-Me₃-Ph | 2-methylbenzyl | H | H | |
| 151 | Et | Me | 2,4,6-Me₃-Ph | CH(CH₂CH₂OCH₃)₂ | H | H | |
| 152 | Et | Me | 2,4,6-Me₃-Ph | 1-cyclopropylethyl | H | H | |
| 153 | Et | Me | 2,4,6-Me₃-Ph | 1-cyclopropylbutyl | H | H | |
| 154 | Et | Me | 2,4,6-Me₃-Ph | CH(CH₂OMe)Et | H | H | |
| 155 | Et | Me | 2,4,6-Me₃-Ph | CH(CH₂OMe)Me | H | H | |
| 156 | Et | Me | 2,4,6-Me₃-Ph | CH(CH₂OMe)₂ | H | H | |
| 157 | Et | Me | 2,4,6-Me₃-Ph | 1-cyclobutylethyl | H | H | |
| 158 | Et | Me | 2,4,6-Me₃-Ph | 1-cyclobutylpropyl | H | H | |
| 159 | Et | Me | 2,4,6-Me₃-Ph | CH(CH₂CH=CH₂)₂ | H | H | |
| 160 | Et | Me | 2,4,6-Me₃-Ph | CH(Et)Pr | H | H | |

TABLE 1-continued

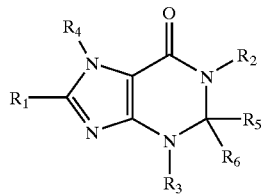

| EX | R₁ | R₂ | R₃ | R₄ | R₅ | R₆ | MP (° C.) |
|---|---|---|---|---|---|---|---|
| 161 | Et | Me | 2,4,6-Me₃-Ph | CH(i-Pr)Et | H | H | oil |
| 162 | Et | Me | 2,4,6-Me₃-Ph | CH(i-Pr)Pr | H | H | |
| 163 | Et | Me | 2,4,6-Me₃-Ph | CH(i-Pr)CH₂OMe | H | H | |
| 164 | Et | Me | 2,4,6-Me₃-Ph | 1-cyclobutylbutyl | H | H | |
| 165 | Et | Me | 2,4,6-Me₃-Ph | CH(cBu)CH₂OMe | H | H | |
| 166 | Et | Me | 2,4,6-Me₃-Ph | CH(cPr)CH₂OMe | H | H | |
| 167 | Et | cPr | 2,4,6-Me₃-Ph | 3-pentyl | H | H | |
| 168 | Et | cPr | 2,4,6-Me₃-Ph | 4-heptyl | H | H | |
| 169 | Et | cPr | 2,4,6-Me₃-Ph | CH(CH₂OMe)Et | H | H | |
| 170 | Et | cPr | 2,4,6-Me₃-Ph | CH(CH₂OMe)Pr | H | H | |
| 171 | Et | Me | 2-Cl-4-OMe-5-F-Ph | 3-pentyl | H | H | |
| 172 | Et | Me | 2-Cl-4-OMe-5-F-Ph | 4-heptyl | H | H | |
| 173 | Et | Me | 2-Cl-4-OMe-5-F-Ph | 2-pentyl | H | H | |
| 174 | Et | Me | 2-Cl-4-OMe-5-F-Ph | CH(CH₂OMe)Pr | H | H | |
| 175 | Et | Me | 2-Cl-4-OMe-5-F-Ph | 1-cyclopropylpropyl | H | H | |
| 176 | Et | Me | 2-Cl-4-OMe-5-F-Ph | 3-heptyl | H | H | |
| 177 | Et | Me | 2-Cl-4-OMe-5-F-Ph | dicyclopropylmethyl | H | H | |
| 178 | Et | Me | 2-Cl-4-OMe-5-F-Ph | 2-methylbenzyl | H | H | |
| 179 | Et | Me | 2-Cl-4-OMe-5-F-Ph | CH(CH₂CH₂OCH₃)₂ | H | H | |
| 180 | Et | Me | 2-Cl-4-OMe-5-F-Ph | 1-cyclopropylethyl | H | H | |
| 181 | Et | Me | 2-Cl-4-OMe-5-F-Ph | 1-cyclopropylbutyl | H | H | |
| 182 | Et | Me | 2-Cl-4-OMe-5-F-Ph | CH(CH₂OMe)Et | H | H | |
| 183 | Et | Me | 2-Cl-4-OMe-5-F-Ph | CH(CH₂OMe)Me | H | H | |
| 184 | Et | Me | 2-Cl-4-OMe-5-F-Ph | CH(CH₂OMe)₂ | H | H | |
| 185 | Et | Me | 2-Cl-4-OMe-5-F-Ph | 1-cyclobutylethyl | H | H | |
| 186 | Et | Me | 2-Cl-4-OMe-5-F-Ph | 1-cyclobutylpropyl | H | H | |
| 187 | Et | Me | 2-Cl-4-OMe-5-F-Ph | CH(CH₂CH=CH₂)₂ | H | H | |
| 188 | Et | Me | 2-Cl-4-OMe-5-F-Ph | CH(Et)Pr | H | H | |
| 189 | Et | Me | 2-Cl-4-OMe-5-F-Ph | CH(i-Pr)Et | H | H | |
| 190 | Et | Me | 2-Cl-4-OMe-5-F-Ph | CH(i-Pr)Pr | H | H | |
| 191 | Et | Me | 2-Cl-4-OMe-5-F-Ph | CH(i-Pr)CH₂OMe | H | H | |
| 192 | Et | Me | 2-Cl-4-OMe-5-F-Ph | 1-cyclobutylbutyl | H | H | |
| 193 | Et | Me | 2-Cl-4-OMe-5-F-Ph | CH(cBu)CH₂OMe | H | H | |
| 194 | Et | Me | 2-Cl-4-OMe-5-F-Ph | CH(cPr)CH₂OMe | H | H | |
| 195 | Et | Me | 2-Me-4-OMe-pyrid-3-yl | 3-pentyl | H | H | |
| 196 | Et | Me | 2-Me-4-OMe-pyrid-3-yl | 4-heptyl | H | H | 120–122 |
| 197 | Et | Me | 2-Me-4-OMe-pyrid-3-yl | 2-pentyl | H | H | |
| 198 | Et | Me | 2-Me-4-OMe-pyrid-3-yl | CH(CH₂₁ OMe)Pr | H | H | |
| 199 | Et | Me | 2-Me-4-OMe-pyrid-3-yl | 1-cyclopropylpropyl | H | H | |
| 200 | Et | Me | 2-Me-4-OMe-pyrid-3-yl | 3-heptyl | H | H | |
| 201 | Et | Me | 2-Me-4-OMe-pyrid-3-yl | dicyclopropylmethyl | H | H | |
| 202 | Et | Me | 2-Me-4-OMe-pyrid-3-yl | 2-methylbenzyl | H | H | |
| 203 | Et | Me | 2-Me-4-OMe-pyrid-3-yl | CH(CH₂CH₂OCH₃)₂ | H | H | |
| 204 | Et | Me | 2-Me-4-OMe-pyrid-3-yl | 1-cyclopropylethyl | H | H | |
| 205 | Et | Me | 2-Me-4-OMe-pyrid-3-yl | 1-cyclopropylbutyl | H | H | |
| 206 | Et | Me | 2-Me-4-OMe-pyrid-3-yl | CH(CH₂OMe)Et | H | H | |
| 207 | Et | Me | 2-Me-4-OMe-pyrid-3-yl | CH(CH₂OMe)Me | H | H | |
| 208 | Et | Me | 2-Me-4-OMe-pyrid-3-yl | CH(CH₂OMe)₂ | H | H | |
| 209 | Et | Me | 2-Me-4-OMe-pyrid-3-yl | 1-cyclobutylethyl | H | H | |
| 210 | Et | Me | 2-Me-4-OMe-pyrid-3-yl | 1-cyclobutylpropyl | H | H | |
| 211 | Et | Me | 2-Me-4-OMe-pyrid-3-yl | CH(CH₂CH=CH₂)₂ | H | H | |
| 212 | Et | Me | 2-Me-4-OMe-pyrid-3-yl | CH(Et)Pr | H | H | |
| 213 | Et | Me | 2-Me-4-OMe-pyrid-3-yl | CH(i-Pr)Et | H | H | |
| 214 | Et | Me | 2-Me-4-OMe-pyrid-3-yl | CH(i-Pr)Pr | H | H | |
| 215 | Et | Me | 2-Me-4-OMe-pyrid-3-yl | CH(i-Pr)CH₂OMe | H | H | |
| 216 | Et | Me | 2-Me-4-OMe-pyrid-3-yl | 1-cyclobutylbutyl | H | H | |
| 217 | Et | Me | 2-Me-4-OMe-pyrid-3-yl | CH(cBu)CH₂OMe | H | H | |
| 218 | Et | Me | 2-Me-4-OMe-pyrid-3-yl | CH(cPr)CH₂OMe | H | H | |
| 219 | Et | Me | 2-OMe-4-i-Pr-Ph | 3-pentyl | H | H | |
| 220 | Et | Me | 2-OMe-4-i-Pr-Ph | 4-heptyl | H | H | |
| 221 | Et | Me | 2-OMe-4-i-Pr-Ph | 2-pentyl | H | H | |
| 222 | Et | Me | 2-OMe-4-i-Pr-Ph | CH(CH₂OMe)Pr | H | H | |
| 223 | Et | Me | 2-OMe-4-i-Pr-Ph | 1-cyclopropylpropyl | H | H | |
| 224 | Et | Me | 2-OMe-4-i-Pr-Ph | 3-heptyl | H | H | |
| 225 | Et | Me | 2-OMe-4-i-Pr-Ph | dicyclopropylmethyl | H | H | |
| 226 | Et | Me | 2-OMe-4-i-Pr-Ph | 2-methylbenzyl | H | H | |

TABLE 1-continued

| EX | $R_1$ | $R_2$ | $R_3$ | $R_4$ | $R_5$ | $R_6$ | MP (° C.) |
|---|---|---|---|---|---|---|---|
| 227 | Et | Me | 2-OMe-4-i-Pr-Ph | CH(CH$_2$CH$_2$OCH$_3$)$_2$ | H | H | |
| 228 | Et | Me | 2-OMe-4-i-Pr-Ph | 1-cyclopropylethyl | H | H | |
| 229 | Et | Me | 2-OMe-4-i-Pr-Ph | 1-cyclopropylbutyl | H | H | |
| 230 | Et | Me | 2-OMe-4-i-Pr-Ph | CH(CH$_2$OMe)Et | H | H | |
| 231 | Et | Me | 2-OMe-4-i-Pr-Ph | CH(CH$_2$OMe)Me | H | H | |
| 232 | Et | Me | 2-OMe-4-i-Pr-Ph | CH(CH$_2$OMe)$_2$ | H | H | |
| 233 | Et | Me | 2-OMe-4-i-Pr-Ph | 1-cyclobutylethyl | H | H | |
| 234 | Et | Me | 2-OMe-4-i-Pr-Ph | 1-cyclobutylpropyl | H | H | |
| 235 | Et | Me | 2-OMe-4-i-Pr-Ph | CH(CH$_2$CH=CH$_2$)$_2$ | H | H | |
| 236 | Et | Me | 2-OMe-4-i-Pr-Ph | CH(Et)Pr | H | H | |
| 237 | Et | Me | 2-OMe-4-i-Pr-Ph | CH(i-Pr)Et | H | H | |
| 238 | Et | Me | 2-OMe-4-i-Pr-Ph | CH(i-Pr)Pr | H | H | |
| 239 | Et | Me | 2-OMe-4-i-Pr-Ph | CH(i-Pr)CH$_2$OMe | H | H | |
| 240 | Et | Me | 2-OMe-4-i-Pr-Ph | 1-cyclobutylbutyl | H | H | |
| 241 | Et | Me | 2-OMe-4-i-Pr-Ph | CH(cBu)CH$_2$OMe | H | H | |
| 242 | Et | Me | 2-OMe-4-i-Pr-Ph | CH(cPr)CH$_2$OMe | H | H | |
| 243 | Et | Me | 2-Me-4-OMe-Ph | 3-pentyl | H | H | |
| 244 | Et | Me | 2-Me-4-OMe-Ph | 4-heptyl | H | H | |
| 245 | Et | Me | 2-Me-4-OMe-Ph | 2-pentyl | H | H | |
| 246 | Et | Me | 2-Me-4-OMe-Ph | CH(CH$_2$OMe)Pr | H | H | |
| 247 | Et | Me | 2-Me-4-OMe-Ph | 1-cyclopropylpropyl | H | H | |
| 248 | Et | Me | 2-Me-4-OMe-Ph | 3-heptyl | H | H | |
| 249 | Et | Me | 2-Me-4-OMe-Ph | dicyclopropylmethyl | H | H | |
| 250 | Et | Me | 2-Me-4-OMe-Ph | 2-methylbenzyl | H | H | |
| 251 | Et | Me | 2-Me-4-OMe-Ph | CH(CH$_2$CH$_2$OCH$_3$)$_2$ | H | H | |
| 252 | Et | Me | 2-Me-4-OMe-Ph | 1-cyclopropylethyl | H | H | |
| 253 | Et | Me | 2-Me-4-OMe-Ph | 1-cyclopropylbutyl | H | H | |
| 254 | Et | Me | 2-Me-4-OMe-Ph | CH(CH$_2$OMe)Et | H | H | |
| 255 | Et | Me | 2-Me-4-OMe-Ph | CH(CH$_2$OMe)Me | H | H | |
| 256 | Et | Me | 2-Me-4-OMe-Ph | CH(CH$_2$OMe)$_2$ | H | H | |
| 257 | Et | Me | 2-Me-4-OMe-Ph | 1-cyclobutylethyl | H | H | |
| 258 | Et | Me | 2-Me-4-OMe-Ph | 1-cyclobutylpropyl | H | H | |
| 259 | Et | Me | 2-Me-4-OMe-Ph | CH(CH$_2$CH=CH$_2$)$_2$ | H | H | |
| 260 | Et | Me | 2-Me-4-OMe-Ph | CH(Et)Pr | H | H | |
| 261 | Et | Me | 2-Me-4-OMe-Ph | CH(i-Pr)Et | H | H | |
| 262 | Et | Me | 2-Me-4-OMe-Ph | CH(i-Pr)Pr | H | H | |
| 263 | Et | Me | 2-Me-4-OMe-Ph | CH(i-Pr)CH$_2$OMe | H | H | |
| 264 | Et | Me | 2-Me-4-OMe-Ph | 1-cyclobutylbutyl | H | H | |
| 265 | Et | Me | 2-Me-4-OMe-Ph | CH(cBu)CH$_2$OMe | H | H | |
| 266 | Et | Me | 2-Me-4-OMe-Ph | CH(cPr)CH$_2$OMe | H | H | |
| 267 | Et | Me | 2,5-Me$_2$-4-OMe-Ph | 3-pentyl | H | H | |
| 268 | Et | Me | 2,5-Me$_2$-4-OMe-Ph | 4-heptyl | H | H | |
| 269 | Et | Me | 2,5-Me$_2$-4-OMe-Ph | 2-pentyl | H | H | |
| 270 | Et | Me | 2,5-Me$_2$-4-OMe-Ph | CH(CH$_2$OMe)Pr | H | H | |
| 271 | Et | Me | 2,5-Me$_2$-4-OMe-Ph | 1-cyclopropylpropyl | H | H | |
| 272 | Et | Me | 2,5-Me$_2$-4-OMe-Ph | 3-heptyl | H | H | |
| 273 | Et | Me | 2,5-Me$_2$-4-OMe-Ph | dicyclopropylmethyl | H | H | |
| 274 | Et | Me | 2,5-Me$_2$-4-OMe-Ph | 2-methylbenzyl | H | H | |
| 275 | Et | Me | 2,5-Me$_2$-4-OMe-Ph | CH(CH$_2$CH$_2$OCH$_3$)$_2$ | H | H | |
| 276 | Et | Me | 2,5-Me$_2$-4-OMe-Ph | 1-cyclopropylethyl | H | H | |
| 277 | Et | Me | 2,5-Me$_2$-4-OMe-Ph | 1-cyclopropylbutyl | H | H | |
| 278 | Et | Me | 2,5-Me$_2$-4-OMe-Ph | CH(CH$_2$OMe)Et | H | H | |
| 279 | Et | Me | 2,5-Me$_2$-4-OMe-Ph | CH(CH$_2$OMe)Me | H | H | |
| 280 | Et | Me | 2,5-Me$_2$-4-OMe-Ph | CH(CH$_2$OMe)$_2$ | H | H | |
| 281 | Et | Me | 2,5-Me$_2$-4-OMe-Ph | 1-cyclobutylethyl | H | H | |
| 282 | Et | Me | 2,5-Me$_2$-4-OMe-Ph | 1-cyclobutylpropyl | H | H | |
| 283 | Et | Me | 2,5-Me$_2$-4-OMe-Ph | CH(CH$_2$CH=CH$_2$)$_2$ | H | H | |
| 284 | Et | Me | 2,5-Me$_2$-4-OMe-Ph | CH(Et)Pr | H | H | |
| 285 | Et | Me | 2,5-Me$_2$-4-OMe-Ph | CH(i-Pr)Et | H | H | |
| 286 | Et | Me | 2,5-Me$_2$-4-OMe-Ph | CH(i-Pr)Pr | H | H | |
| 287 | Et | Me | 2,5-Me$_2$-4-OMe-Ph | CH(i-Pr)CH$_2$OMe | H | H | |
| 288 | Et | Me | 2,5-Me$_2$-4-OMe-Ph | 1-cyclobutylbutyl | H | H | |
| 289 | Et | Me | 2,5-Me$_2$-4-OMe-Ph | CH(cBu)CH$_2$OMe | H | H | |
| 290 | Et | Me | 2,5-Me$_2$-4-OMe-Ph | CH(cPr)CH$_2$OMe | H | H | |
| 291 | Et | Me | 2-OMe-4-CF$_3$-Ph | 3-pentyl | H | H | |
| 292 | Et | Me | 2-OMe-4-CF$_3$-Ph | 4-heptyl | H | H | |

TABLE 1-continued

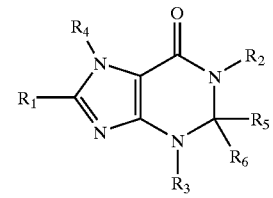

| EX | R₁ | R₂ | R₃ | R₄ | R₅ | R₆ | MP (° C.) |
|----|----|----|----|----|----|----|-----------|
| 293 | Et | Me | 2-OMe-4-CF₃-Ph | 2-pentyl | H | H | |
| 294 | Et | Me | 2-OMe-4-CF₃-Ph | CH(CH₂OMe)Pr | H | H | |
| 295 | Et | Me | 2-OMe-4-CF₃-Ph | 1-cyclopropylpropyl | H | H | |
| 296 | Et | Me | 2-OMe-4-CF₃-Ph | 3-heptyl | H | H | |
| 297 | Et | Me | 2-OMe-4-CF₃-Ph | dicyclopropylmethyl | H | H | |
| 298 | Et | Me | 2-OMe-4-CF₃-Ph | 2-methylbenzyl | H | H | |
| 299 | Et | Me | 2-OMe-4-CF₃-Ph | CH(CH₂CH₂OCH₃)₂ | H | H | |
| 300 | Et | Me | 2-OMe-4-CF₃-Ph | 1-cyclopropylethyl | H | H | |
| 301 | Et | Me | 2-OMe-4-CF₃-Ph | 1-cyclopropylbutyl | H | H | |
| 302 | Et | Me | 2-OMe-4-CF₃-Ph | CH(CH₂OMe)Et | H | H | |
| 303 | Et | Me | 2-OMe-4-CF₃-Ph | CH(CH₂OMe)Me | H | H | |
| 304 | Et | Me | 2-OMe-4-CF₃-Ph | CH(CH₂OMe)₂ | H | H | |
| 305 | Et | Me | 2-OMe-4-CF₃-Ph | 1-cyclobutylethyl | H | H | |
| 306 | Et | Me | 2-OMe-4-CF₃-Ph | 1-cyclobutylpropyl | H | H | |
| 307 | Et | Me | 2-OMe-4-CF₃-Ph | CH(CH₂CH=CH₂)₂ | H | H | |
| 308 | Et | Me | 2-OMe-4-CF₃-Ph | CH(Et)Pr | H | H | |
| 309 | Et | Me | 2-OMe-4-CF₃-Ph | CH(i-Pr)Et | H | H | |
| 310 | Et | Me | 2-OMe-4-CF₃-Ph | CH(i-Pr)Pr | H | H | |
| 311 | Et | Me | 2-OMe-4-CF₃-Ph | CH(i-Pr)CH₂OMe | H | H | |
| 312 | Et | Me | 2-OMe-4-CF₃-Ph | 1-cyclobutylbutyl | H | H | |
| 313 | Et | Me | 2-OMe-4-CF₃-Ph | CH(cBu)CH₂OMe | H | H | |
| 314 | Et | Me | 2-OMe-4-CF₃-Ph | CH(cPr)CH₂OMe | H | H | |
| 315 | Et | Me | 2-Cl-4-OCF₃-Ph | 3-pentyl | H | H | |
| 316 | Et | Me | 2-Cl-4-OCF₃-Ph | 4-heptyl | H | H | |
| 317 | Et | Me | 2-Cl-4-OCF₃-Ph | 2-pentyl | H | H | |
| 318 | Et | Me | 2-Cl-4-OCF₃-Ph | CH(CH₂OMe)Pr | H | H | |
| 319 | Et | Me | 2-Cl-4-OCF₃-Ph | 1-cyclopropylpropyl | H | H | |
| 320 | Et | Me | 2-Cl-4-OCF₃-Ph | 3-heptyl | H | H | |
| 321 | Et | Me | 2-Cl-4-OCF₃-Ph | dicyclopropylmethyl | H | H | |
| 322 | Et | Me | 2-Cl-4-OCF₃-Ph | 2-methylbenzyl | H | H | |
| 323 | Et | Me | 2-Cl-4-OCF₃-Ph | CH(CH₂CH₂OCH₃)₂ | H | H | |
| 324 | Et | Me | 2-Cl-4-OCF₃-Ph | 1-cyclopropylethyl | H | H | |
| 325 | Et | Me | 2-Cl-4-OCF₃-Ph | 1-cyclopropylbutyl | H | H | |
| 326 | Et | Me | 2-Cl-4-OCF₃-Ph | CH(CH₂OMe)Et | H | H | |
| 327 | Et | Me | 2-Cl-4-OCF₃-Ph | CH(CH₂OMe)Me | H | H | |
| 328 | Et | Me | 2-Cl-4-OCF₃-Ph | CH(CH₂OMe)₂ | H | H | |
| 329 | Et | Me | 2-Cl-4-OCF₃-Ph | 1-cyclobutylethyl | H | H | |
| 330 | Et | Me | 2-Cl-4-OCF₃-Ph | 1-cyclobutylpropyl | H | H | |
| 331 | Et | Me | 2-Cl-4-OCF₃-Ph | CH(CH₂CH=CH₂)₂ | H | H | |
| 332 | Et | Me | 2-Cl-4-OCF₃-Ph | CH(Et)Pr | H | H | |
| 333 | Et | Me | 2-Cl-4-OCF₃-Ph | CH(i-Pr)Et | H | H | |
| 334 | Et | Me | 2-Cl-4-OCF₃-Ph | CH(i-Pr)Pr | H | H | |
| 335 | Et | Me | 2-Cl-4-OCF₃-Ph | CH(i-Pr)CH₂OMe | H | H | |
| 336 | Et | Me | 2-Cl-4-OCF₃-Ph | 1-cyclobutylbutyl | H | H | |
| 337 | Et | Me | 2-Cl-4-OCF₃-Ph | CH(cBu)CH₂OMe | H | H | |
| 338 | Et | Me | 2-Cl-4-OCF₃-Ph | CH(cPr)CH₂OMe | H | H | |
| 339 | Et | Me | 2-Cl-4,5-(OMe)₂-Ph | 3-pentyl | H | H | |
| 340 | Et | Me | 2-Cl-4,5-(OMe)₂-Ph | 4-heptyl | H | H | |
| 341 | Et | Me | 2-Cl-4,5-(OMe)₂-Ph | 2-pentyl | H | H | |
| 342 | Et | Me | 2-Cl-4,5-(OMe)₂-Ph | CH(CH₂OMe)Pr | H | H | |
| 343 | Et | Me | 2-Cl-4,5-(OMe)₂-Ph | 1-cyclopropylpropyl | H | H | |
| 344 | Et | Me | 2-Cl-4,5-(OMe)₂-Ph | 3-heptyl | H | H | |
| 345 | Et | Me | 2-Cl-4,5-(OMe)₂-Ph | dicyclopropylmethyl | H | H | |
| 346 | Et | Me | 2-Cl-4,5-(OMe)₂-Ph | 2-methylbenzyl | H | H | |
| 347 | Et | Me | 2-Cl-4,5-(OMe)₂-Ph | CH(CH₂CH₂OCH₃)₂ | H | H | |
| 348 | Et | Me | 2-Cl-4,5-(OMe)₂-Ph | 1-cyclopropylethyl | H | H | |
| 349 | Et | Me | 2-Cl-4,5-(OMe)₂-Ph | 1-cyclopropylbutyl | H | H | |
| 350 | Et | Me | 2-Cl-4,5-(OMe)₂-Ph | CH(CH₂OMe)Et | H | H | |
| 351 | Et | Me | 2-Cl-4,5-(OMe)₂-Ph | CH(CH₂OMe)Me | H | H | |
| 352 | Et | Me | 2-Cl-4,5-(OMe)₂-Ph | CH(CH₂OMe)₂ | H | H | |
| 353 | Et | Me | 2-Cl-4,5-(OMe)₂-Ph | 1-cyclobutylethyl | H | H | |
| 354 | Et | Me | 2-Cl-4,5-(OMe)₂-Ph | 1-cyclobutylpropyl | H | H | |
| 355 | Et | Me | 2-Cl-4,5-(OMe)₂-Ph | CH(CH₂CH=CH₂)₂ | H | H | |
| 356 | Et | Me | 2-Cl-4,5-(OMe)₂-Ph | CH(Et)Pr | H | H | |
| 357 | Et | Me | 2-Cl-4,5-(OMe)₂-Ph | CH(i-Pr)Et | H | H | |
| 358 | Et | Me | 2-Cl-4,5-(OMe)₂-Ph | CH(i-Pr)Pr | H | H | |

TABLE 1-continued

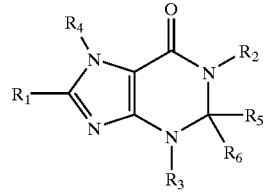

| EX | $R_1$ | $R_2$ | $R_3$ | $R_4$ | $R_5$ | $R_6$ | MP (° C.) |
|---|---|---|---|---|---|---|---|
| 359 | Et | Me | 2-Cl-4,5-(OMe)$_2$-Ph | CH(i-Pr)CH$_2$OMe | H | H | |
| 360 | Et | Me | 2-Cl-4,5-(OMe)$_2$-Ph | 1-cyclobutylbutyl | H | H | |
| 361 | Et | Me | 2-Cl-4,5-(OMe)$_2$-Ph | CH(cBu)CH$_2$OMe | H | H | |
| 362 | Et | Me | 2-Cl-4,5-(OMe)$_2$-Ph | CH(cPr)CH$_2$OMe | H | H | |
| 363 | Et | Me | 2,4-(OMe)$_2$-Ph | 3-pentyl | H | H | |
| 364 | Et | Me | 2,4-(OMe)$_2$-Ph | 4-heptyl | H | H | |
| 365 | Et | Me | 2,4-(OMe)$_2$-Ph | 2-pentyl | H | H | |
| 366 | Et | Me | 2,4-(OMe)$_2$-Ph | CH(CH$_2$OMe)Pr | H | H | |
| 367 | Et | Me | 2,4-(OMe)$_2$-Ph | 1-cyclopropylpropyl | H | H | |
| 368 | Et | Me | 2,4-(OMe)$_2$-Ph | 3-heptyl | H | H | |
| 369 | Et | Me | 2,4-(OMe)$_2$-Ph | dicyclopropylmethyl | H | H | |
| 370 | Et | Me | 2,4-(OMe)$_2$-Ph | 2-methylbenzyl | H | H | |
| 371 | Et | Me | 2,4-(OMe)$_2$-Ph | CH(CH$_2$CH$_2$OCH$_3$)$_2$ | H | H | |
| 372 | Et | Me | 2,4-(OMe)$_2$-Ph | 1-cyclopropylethyl | H | H | |
| 373 | Et | Me | 2,4-(OMe)$_2$-Ph | 1-cyclopropylbutyl | H | H | |
| 374 | Et | Me | 2,4-(OMe)$_2$-Ph | CH(CH$_2$OMe)Et | H | H | |
| 375 | Et | Me | 2,4-(OMe)$_2$-Ph | CH(CH$_2$OMe)Me | H | H | |
| 376 | Et | Me | 2,4-(OMe)$_2$-Ph | CH(CH$_2$OMe)$_2$ | H | H | |
| 377 | Et | Me | 2,4-(OMe)$_2$-Ph | 1-cyclobutylethyl | H | H | |
| 378 | Et | Me | 2,4-(OMe)$_2$-Ph | 1-cyclobutylpropyl | H | H | |
| 379 | Et | Me | 2,4-(OMe)$_2$-Ph | CH(CH$_2$CH=CH$_2$)$_2$ | H | H | |
| 380 | Et | Me | 2,4-(OMe)$_2$-Ph | CH(Et)Pr | H | H | |
| 381 | Et | Me | 2,4-(OMe)$_2$-Ph | CH(i-Pr)Et | H | H | |
| 382 | Et | Me | 2,4-(OMe)$_2$-Ph | CH(i-Pr)Pr | H | H | |
| 383 | Et | Me | 2,4-(OMe)$_2$-Ph | CH(i-Pr)CH$_2$OMe | H | H | |
| 384 | Et | Me | 2,4-(OMe)$_2$-Ph | 1-cyclobutylbutyl | H | H | |
| 385 | Et | Me | 2,4-(OMe)$_2$-Ph | CH(cBu)CH$_2$OMe | H | H | |
| 386 | Et | Me | 2,4-(OMe)$_2$-Ph | CH(cPr)CH$_2$OMe | H | H | |
| 387 | Et | Me | 2-Cl-4-OEt-Ph | 3-pentyl | H | H | |
| 388 | Et | Me | 2-Cl-4-OEt-Ph | 4-heptyl | H | H | |
| 389 | Et | Me | 2-Cl-4-OEt-Ph | 2-pentyl | H | H | |
| 390 | Et | Me | 2-Cl-4-OEt-Ph | CH(CH$_2$OMe)Pr | H | H | |
| 391 | Et | Me | 2-Cl-4-OEt-Ph | 1-cyclopropylpropyl | H | H | |
| 392 | Et | Me | 2-Cl-4-OEt-Ph | 3-heptyl | H | H | |
| 393 | Et | Me | 2-Cl-4-OEt-Ph | dicyclopropylmethyl | H | H | |
| 394 | Et | Me | 2-Cl-4-OEt-Ph | 2-methylbenzyl | H | H | |
| 395 | Et | Me | 2-Cl-4-OEt-Ph | CH(CH$_2$CH$_2$OCH$_3$)$_2$ | H | H | |
| 396 | Et | Me | 2-Cl-4-OEt-Ph | 1-cyclopropylethyl | H | H | |
| 397 | Et | Me | 2-Cl-4-OEt-Ph | 1-cyclopropylbutyl | H | H | |
| 398 | Et | Me | 2-Cl-4-OEt-Ph | CH(CH$_2$OMe)Et | H | H | |
| 399 | Et | Me | 2-Cl-4-OEt-Ph | CH(CH$_2$OMe)Me | H | H | |
| 400 | Et | Me | 2-Cl-4-OEt-Ph | CH(CH$_2$OMe)$_2$ | H | H | |
| 401 | Et | Me | 2-Cl-4-OEt-Ph | 1-cyclobutylethyl | H | H | |
| 402 | Et | Me | 2-Cl-4-OEt-Ph | 1-cyclobutylpropyl | H | H | |
| 403 | Et | Me | 2-Cl-4-OEt-Ph | CH(CH$_2$CH=CH$_2$)$_2$ | H | H | |
| 404 | Et | Me | 2-Cl-4-OEt-Ph | CH(Et)Pr | H | H | |
| 405 | Et | Me | 2-Cl-4-OEt-Ph | CH(i-Pr)Et | H | H | |
| 406 | Et | Me | 2-Cl-4-OEt-Ph | CH(i-Pr)Pr | H | H | |
| 407 | Et | Me | 2-Cl-4-OEt-Ph | CH(i-Pr)CH$_2$OMe | H | H | |
| 408 | Et | Me | 2-Cl-4-OEt-Ph | 1-cyclobutylbutyl | H | H | |
| 409 | Et | Me | 2-Cl-4-OEt-Ph | CH(cBu)CH$_2$OMe | H | H | |
| 410 | Et | Me | 2-Cl-4-OEt-Ph | CH(cpr)CH$_2$OMe | H | H | |
| 411 | Et | Me | 2,4-Me$_2$-pyrid-3-yl | 3-pentyl | H | H | |
| 412 | Et | Me | 2,4-Me$_2$-pyrid-3-yl | 4-heptyl | H | H | |
| 413 | Et | Me | 2,4-Me$_2$-pyrid-3-yl | 2-pentyl | H | H | |
| 414 | Et | Me | 2,4-Me$_2$-pyrid-3-yl | CH(CH$_2$OMe)Pr | H | H | |
| 415 | Et | Me | 2,4-Me$_2$-pyrid-3-yl | 1-cyclopropylpropyl | H | H | |
| 416 | Et | Me | 2,4-Me$_2$-pyrid-3-yl | 3-heptyl | H | H | |
| 417 | Et | Me | 2,4-Me$_2$-pyrid-3-yl | dicyclopropylmethyl | H | H | |
| 418 | Et | Me | 2,4-Me$_2$-pyrid-3-yl | 2-methylbenzyl | H | H | |
| 419 | Et | Me | 2,4-Me$_2$-pyrid-3-yl | CH(CH$_2$CH$_2$OCH$_3$)$_2$ | H | H | |
| 420 | Et | Me | 2,4-Me$_2$-pyrid-3-yl | 1-cyclopropylethyl | H | H | |
| 421 | Et | Me | 2,4-Me$_2$-pyrid-3-yl | 1-cyclopropylbutyl | H | H | |
| 422 | Et | Me | 2,4-Me$_2$-pyrid-3-yl | CH(CH$_2$OMe)Et | H | H | |
| 423 | Et | Me | 2,4-Me$_2$-pyrid-3-yl | CH(CH$_2$OMe)Me | H | H | |
| 424 | Et | Me | 2,4-Me$_2$-pyrid-3-yl | CH(CH$_2$OMe)$_2$ | H | H | |

TABLE 1-continued

[Structure: imidazo-pyrimidinone core with substituents $R_1$, $R_2$, $R_3$, $R_4$, $R_5$, $R_6$ and a carbonyl (=O)]

| EX | $R_1$ | $R_2$ | $R_3$ | $R_4$ | $R_5$ | $R_6$ | MP (° C.) |
|---|---|---|---|---|---|---|---|
| 425 | Et | Me | 2,4-Me$_2$-pyrid-3-yl | 1-cyclobutylethyl | H | H | |
| 426 | Et | Me | 2,4-Me$_2$-pyrid-3-yl | 1-cyclobutylpropyl | H | H | |
| 427 | Et | Me | 2,4-Me$_2$-pyrid-3-yl | CH(CH$_2$CH=CH$_2$)$_2$ | H | H | |
| 428 | Et | Me | 2,4-Me$_2$-pyrid-3-yl | CH(Et)Pr | H | H | |
| 429 | Et | Me | 2,4-Me$_2$-pyrid-3-yl | CH(i-Pr)Et | H | H | |
| 430 | Et | Me | 2,4-Me$_2$-pyrid-3-yl | CH(i-Pr)Pr | H | H | |
| 431 | Et | Me | 2,4-Me$_2$-pyrid-3-yl | CH(i-Pr)CH$_2$OMe | H | H | |
| 432 | Et | Me | 2,4-Me$_2$-pyrid-3-yl | 1-cyclobutylbutyl | H | H | |
| 433 | Et | Me | 2,4-Me$_2$-pyrid-3-yl | CH(cBu)CH$_2$OMe | H | H | |
| 434 | Et | Me | 2,4-Me$_2$-pyrid-3-yl | CH(cPr)CH$_2$OMe | H | H | |
| 435 | Et | Me | 2-Me-4-OMe-5-F-Ph | 4-heptyl | H | H | |
| 436 | Et | Me | 2-Me-4-OMe-5-F-Ph | 3-heptyl | H | H | |

Also provided herein are pharmaceutical compositions comprising compounds of this invention and a pharmaceutically acceptable carrier, which are media generally accepted in the art for the delivery of biologically active agents to animals, in particular, mammals. Pharmaceutically acceptable carriers are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences,* 17th ed., Mack Publishing Company, Easton, Pa., 1985, the contents of which are incorporated herein by reference.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

This invention is described in the following examples, which those of ordinary skill in the art will readily understand are not limiting on the invention as defined in the claims which follow thereafter.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, $\mu$L for microliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "α", "β", "R" and "S" are stereochemical designations familiar to those skilled in the art.

Example 1

3-(2,4-dichlorophenyl)-8-ethyl-1-methyl-7-(3-pentyl)-1,2,3,7-tetrahydro-6H-purin-6-one

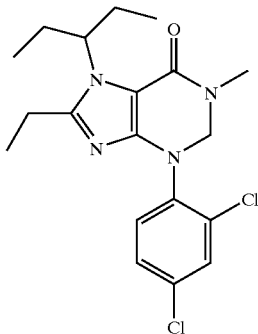

A. N-(2,4-dichlorophenyl)-N'-methyl-urea

A cooled (0° C.) solution of methylamine in EtOH (50 mL, 400 mmol, 8.0 M) in anhydrous THF (300 mL) was treated with 2,4-dichlorophenylisocyanate (25.0 g, 133 mmol). The cooling bath was removed and the mixture was warmed to 65° C. for 20 min. The reaction mixture was then cooled to 0° C. The solid was collected on a Buchner funnel, washed with cold ether, and dried under vacuum to afford N-(2,4-dichlorophenyl)-N'-methyl-urea (21.7 g, 74% yield) as a colorless solid: mp 213.5–214.5° C.; $^1$H NMR (300 MHz, DMSO-$d_6$) δ 8.17 (d, J=9.2 Hz, 1H), 8.11 (s, 1H), 7.55 (d, J=2.5 Hz, 1H), 7.32 (dd, J=8.8, 2.6 Hz, 1H), 6.91 (d, J=4.8 Hz, 1H), 2.65 (d, J=4.4 Hz, 3H); LRMS (APCI) m/e 259.9 [(M+H+CH$_3$CN)$^+$, calcd for $C_{10}H_{12}N_3OCl_2$, 260.0].

B. 6-amino-1-(2,4-dichlorophenyl)-3-methyl-2,4(1H,3H)-pyrimidinedione

A solution of N-(2,4-dichlorophenyl)-N'-methyl-urea (12.0 g, 54.8 mmol) in acetic anhydride (100 mL) was treated with cyanoacetic acid (5.6 g, 65.8 mmol). The reaction mixture was heated at 85° C. for 2.5 h. Additional cyanoacetic acid (0.90 g, 11.0 mmol) was added and the reaction mixture was stirred for 45 min. A third portion of cyanoacetic acid (0.45 g, 5.5 mmol) was added and the reaction mixture was stirred for 30 min. Excess acetic anhydride was distilled off under reduced pressure at a temperature not higher than 70° C. The residue was treated with 20% aqueous sodium hydroxide (95 mL) in portions. During the addition a spontaneous increase in temperature (65–70° C.) occurred. The reaction mixture was heated at 60° C. for 1 h during which time the product precipitated. The reaction mixture was then cooled to 0° C. The precipitate was collected on a Buchner funnel, washed with cold water, and dried at 55° C. under vacuum. The crude product was triturated in hot toluene (stirred for 1 h at 110° C.), and the solid was immediately collected on a Buchner funnel then dried under vacuum to afford a pale yellow solid (8.46 g, 54% yield): mp 249–251° C.; $^1$H NMR (300 MHz, DMSO-$d_6$) δ 7.89 (d, J=1.8 Hz, 1H), 7.59 (d, J=1.8 Hz, 2H), 6.44 (s br, 1H), 4.79 (s, 1H), 3.09 (s, 3H); LRMS (APCI) m/e 286.0 [(M+H)$^+$, calcd for $C_{11}H_{10}N_3O_2Cl_2$ 286.0].

C. 6-amino-1-(2,4-dichlorophenyl)-3-methyl-5-nitroso-2,4(1H,3H)-pyrimidinedione

To a suspension of the intermediate produced in Part B (8.0 g, 28.0 mmol) in H$_2$O (65 mL) and acetic acid (3.5 mL) was added NaNO$_2$ (2.12 g, 30.8 mmol) in portions. The reaction mixture was heated at 50° C. for 2 h during which time a purple color formed indicating formation of the nitroso derivative. Additional NaNO$_2$ (2.12 g, 30.8 mmol) was added and the reaction mixture was stirred at 65° C. for an additional 2 h. Additional NaNO$_2$ (300 mg, 4.35 mmol) was added and the reaction mixture was heated at 75° C. for another 1 h. The suspension was then cooled to 0° C. The solid was collected on a Buchner funnel, washed with cold water, and dried under vacuum at 60° C. overnight to afford the nitroso derivative as a purple solid (7.78 g, 88% yield) which was used directly in the next step without further purification: mp 230–232° C.; $^1$H NMR (300 MHz, DMSO-$d_6$) δ 12.62 (s, 1H), 8.70 (s, 1H), 7.98 (s, 1H), 7.68 (s, 2H), 3.32 (s, 3H); LRMS (APCI) m/e 314.9 [(M+H)$^+$, calcd for $C_{11}H_9N_4O_3C_2$ 315.0].

D. 5,6-diamino-1-(2,4-dichlorophenyl)-3-methyl-2,4(1H,3H)-pyrimidinedione

To a suspension of finely ground material which was produced in Part C (7.32 g, 23.2 mmol) in 25% NH$_4$OH (60 mL) was added in portions Na$_2$S$_2$O$_4$ (20.0 g, 116 mmol). A mildly exothermic reaction occurred. After the addition was complete, the reaction mixture was heated at 50° C. for 2.5 h. The purple color gradually disappeared. The reaction mixture was cooled to 0° C. The solid was collected on a Buchner funnel, washed with cold water, then dried under vacuum overnight at 60° C. to afford a pale green solid (6.40 g, 92% yield) which was used directly in the next step without further purification: mp 170–172.5° C.; $^1$H NMR (300 MHz, DMSO-$d_6$) δ 7.88 (d, J=2.2 Hz, 1H), 7.61–7.53 (m, 2H), 5.73 (s, 2H), 3.34 (s, 2H), 3.15 (s, 3H); LRMS (APCI) m/e 300.9 [(M+H)$^+$, calcd for $C_{11}H_{11}N_4O_2Cl_2$ 301.0].

E. 3-(2,4-dichlorophenyl)-8-ethyl-1-methyl-3,7-dihydro-1H-purine-2,6-dione

A suspension of the product from Part D (4.0 g, 13.3 mmol) in EtOH (32 mL) was treated with triethylorthopropionate (12.8 mL, 63.7 mmol). The reaction mixture was heated at reflux for 6 h during which time the product precipitated from the solution. The reaction mixture was then cooled to 0° C. to achieve complete precipitation. The solid was collected on a Buchner funnel, washed with cold ether, and dried under vacuum to give a colorless solid (2.97 g). The filtrate was concentrated and the residue was purified by column chromatography on silica gel (5% MeOH in CH$_2$Cl$_2$) to afford an additional 0.87 g of desried product. The total yield of desired product was 3.84 g (85% yield) as a colorless solid: mp 274.5–275.5° C.; $^1$H NMR (300 MHz, CDCl$_3$) δ 12.53 (s br, 1H), 7.61 (d, J=1.8 Hz, 1H), 7.45–7.38 (m, 2H), 3.52 (s, 3H), 2.87 (q, J=7.3 Hz, 2H), 1.38 (t, J=7.7 Hz, 3H); LRMS (APCI) m/e 339.0 [(M+H)$^+$, calcd for $C_{14}H_{13}N_4O_2Cl_2$ 339.0].

F. 3-(2,4-dichlorophenyl)-8-ethyl-1-methyl-7-(3-pentyl)-3,7-dihydro-1H-purine-2,6-dione

Method A

A solution of product from Part E (544 mg, 1.60 mmol) in anhydrous DMF (8 mL) was treated with finely ground K$_2$CO$_3$ (662 mg, 4.80 mmol). After stirring 5 min at rt, 3-methanesulfonylpentane (682 μL, 4.48 mmol) was added via syringe and the reaction mixture was heated at 80° C. for 2 h. The mixture was cooled to rt and transferred to a separatory funnel containing ether (120 mL). The organic layer was washed with water (4×15 mL), brine (15 mL), dried over MgSO$_4$, filtered, and concentrated. The solid residue was crystallized from hexane/ethyl acetete and collected on a Buchner funnel to give a colorless solid (508 mg). The filtrate was concentrated and the residue was purified by column chromatography on silica gel (25% ethyl acetate in hexanes) to give an additional 105 mg of product. The total yield of desired product was 613 mg (94% yield) as a colorless solid: mp 186–187° C.; $^1$H NMR (300 MHz, CDCl$_3$) δ 7.59 (d, J=2.2 Hz, 1H), 7.44–7.36 (m, 2H), 4.00–3.90 (m, 1H), 3.45 (s, 3H), 2.74 (q, J=7.7 Hz, 2H), 2.39–2.26 (m, 2H), 2.05–1.92 (m, 2H), 1.24 (t, J=7.3 Hz, 3H), 0.83 (t, J=7.3 Hz, 6H); HRMS (ESI) m/e 409.1212 [(M+H)$^+$, calcd for $C_{19}H_{23}N_4O_2Cl_2$ 409.1198].

Method B

A solution of product from Part E (100 mg, 0.295 mmol) in anhydrous THF (1.2 mL) was heated to 50° C. PPh$_3$ (120 mg, 0.594 mmol) and 3-pentanol (96 μL, 0.889 mmol) were added. After stirring 5 min, DEAD (102 μL, 0.648 mmol) was added rapidly via syringe and the reaction mixture was stirred 15 min at 50° C. The mixture was cooled to rt and was poured into a separatory funnel containing saturated aqueous NaHCO$_3$ (15 mL). The aqueous layer was extracted with EtOAc (3×15 mL). The combined organic layers were washed with brine, dried over MgSO$_4$. filtered, and concentrated. The residue was purified by prep plate (two 1000 μM silica gel plates, 60% ethyl acetate/40% hexanes) to afford the desired product (88 mg, 64% yield) as a colorless solid. The spectral data is identical to that reported in method A.

G. 4-[(2,4-dichlorophenyl)amino]-2-ethyl-N-methyl-1-(3-pentyl)-1H-imidazole-5-carboxamide The product produced in Part F (268 mg, 0.655 mmol), was dissolved in dioxane (1 mL). EtOH (1 mL) and aqueous NaOH (2 mL, 3 N) were added and the reaction mixture was heated at reflux for 3.5 h. The mixture was cooled to rt and transferred to a separatory funnel containing saturated aqueous NaHCO$_3$ (15 mL). The aqueous layer was extracted with EtOAc (3×15 mL). The combined organic layers were washed with brine, dried over MgSO$_4$, filtered, and concentrated. The residue was purified by column chromatography on silica gel (30% ethyl acetate in hexanes with 0.2% MeOH) to afford a colorless amorphous solid (120 mg, 48% yield) $^1$H NMR (300 MHz, CDCl$_3$) δ 7.33 (d, J=2.2 Hz, 1H), 7.07 (dd, J=8.7, 2.5 Hz, 1H), 6.91 (s br, 1H), 6.86 (d, J=8.8 Hz, 1H), 6.20 (s, 1H), 2.82 (d, J=4.7 Hz, 3H), 2.74 (q, J=7.4 Hz, 2H), 1.98–1.86 (m, 4H), 1.33 (t, J=7.7 Hz, 3H), 0.86 (t, J=7.7 Hz, 6H); HRMS (ESI) m/e 383.1423 [(M+H)$^+$; calcd for C$_{18}$H$_{25}$N$_4$OCl$_2$ 383.1405].

H. 3-(2,4-dichlorophenyl)-8-ethyl-1-methyl-7-(3-pentyl)-1,2,3,7-tetrahydro-6H-purin-6-one The product produced in Part G (35 mg, 0.091 mmol) was dissolved in toluene (5 mL) and was treated with paraformaldehyde (150 mg) and p-TsOH.H$_2$O (10 mg, 0.053 mmol). The mixture was heated at reflux for 1.25 h in a flask equipped with a Dean-Stark trap. The mixture was cooled to rt, and transferred to a separatory funnel containing saturated aqueous NaHCO$_3$ (15 mL). The aqueous layer was extracted with EtOAc (3×15 mL). The combined organic layers were washed with brine, dried over MgSO$_4$, filtered, and concentrated. The residue was purified by prep plate (1000 μM silica gel plate, 30% ethyl acetate in hexanes) to afford the title compound (29 mg, 81% yield) as a colorless solid: mp 132–133° C.; $^1$H NMR (300 MHz, CDCl$_3$) δ 7.45 (d, J=2.6 Hz, 1H), 7.16 (dd, J=8.8, 2.6 Hz, 1H), 6.99 (d, J=8.8 Hz, 1H), 4.84 (s, 2H), 2.95 (s, 3H), 2.72 (q, J=7.6 Hz, 2H), 2.35–2.18 (m, 2H), 1.99–1.90 (m, 2H), 1.27 (t, J=7.4 Hz, 3H), 0.86 (t, J=7.4 Hz, 6H); HRMS (ESI) m/e 395.1406 [(M+H)$^+$, calcd for C$_{19}$H$_{25}$N$_4$OCl$_2$ 395.1405].

Example 2

3-(2,4-dichlorophenyl)-8-ethyl-7-(4-heptyl)-1-methyl-1,2,3,7-tetrahydro-6H-purin-6-one

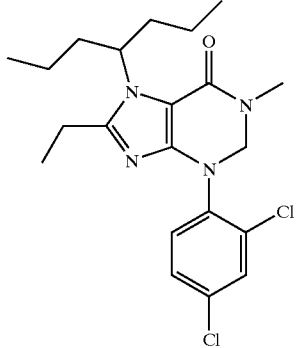

Prepared by the method described in example 1 using the appropriate starting materials to give the desired product as a solid: mp 117–118° C.; HRMS (ESI) m/e 423.1736 [(M+H)$^+$, calcd for C$_{21}$H$_{29}$N$_4$OCl$_2$ 423.1718].

Example 3

3-(2,4-dichlorophenyl)-1,2-dimethyl-8-ethyl-7-(3-pentyl)-1,2,3,7-tetrahydro-6H-purin-6-one

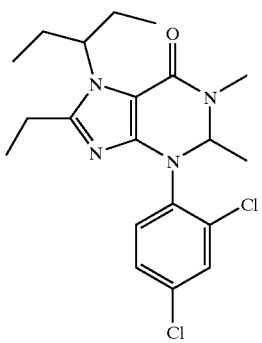

Prepared by the method described in example 1 using the appropriate starting materials to give the desired product as a solid: mp 135–136.5° C.; HRMS (ESI) m/e 409.1581 [(M+H)$^+$, calcd for C$_{20}$H$_{27}$N$_4$OCl$_2$ 409.1562].

Example 4

3-(2,4-dichlorophenyl)-2,8-diethyl-1-methyl-7-(3-pentyl)-1,2,3,7-tetrahydro-6H-purin-6-one

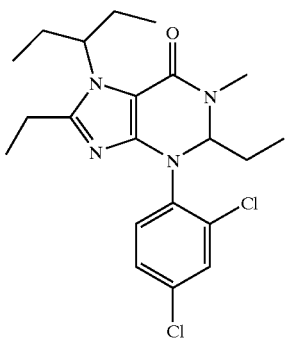

Prepared by the method described in example 1 using the appropriate starting materials to give the desired product as a solid: colorless oil; HRMS (ESI) m/e 423.1747 [(M+H)+, calcd for $C_{21}H_{29}N_4OCl_2$ 423.1718].

Example 5

3-(2,4-dichlorophenyl)-1,2-dimethyl-8-ethyl-7-(4-heptyl)-1,2,3,7-tetrahydro-6H-purin-6-one

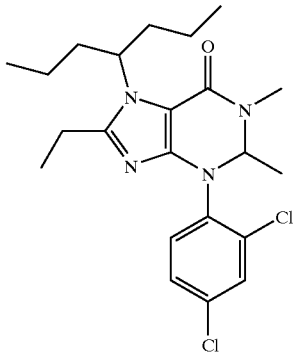

Prepared by the method described in example 1 using the appropriate starting materials to give the desired product as a solid: mp 144–145.5° C.; HRMS (ESI) m/e 437.1871 [(M+H)+, calcd for $C_{22}H_{31}N_4OCl_2$ 437.1875].

Example 6

3-(2,4-dichlorophenyl)-2,8-diethyl-7-(4-heptyl)-1-methyl-1,2,3,7-tetrahydro-6H-purin-6-one

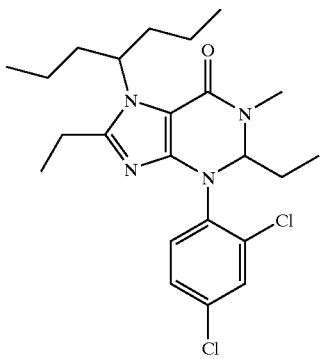

Prepared by the method described in example 1 using the appropriate starting materials to give the desired product as a colorless solid: mp 116.5–117.5° C.; HRMS (ESI) m/e 451.2040 [(M+H)+, calcd for $C_{23}H_{33}N_4OCl_2$ 451.2031].

Example 7

7-benzyloxymethyl-3-(2,4-dichlorophenyl)-8-ethyl-1-methyl-1,2,3,7-tetrahydro-6H-purin-6-one

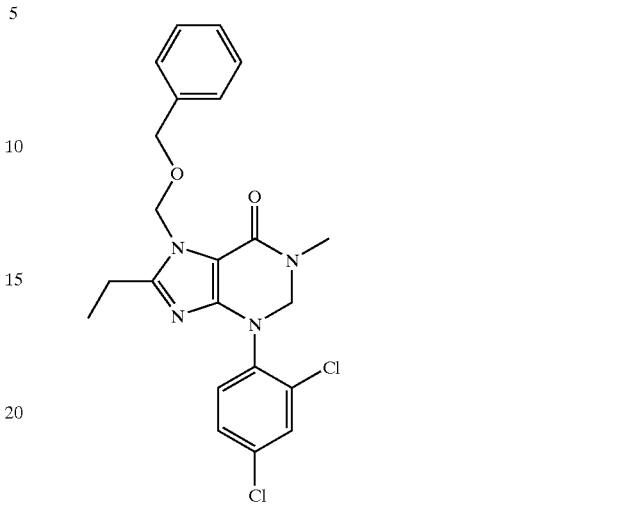

A. 7-benzyloxymethyl-3-(2,4-dichlorophenyl)-8-ethyl-1-methyl-3,7-dihydro-1H-purine-2,6-dione 3-(2,4-dichlorophenyl)-8-ethyl-1-methyl-3,7-dihydro-1H-purine-2,6-dione (6.00 g, 17.69 mmol), prepared according to the procedure in example 1, was dissolved in anhydrous DMF (80 mL). $K_2CO_3$ (6.11 g, 44.23 mmol), $Bu_4NI$ (1.31 g, 3.54 mmol) and BOMCl (4.4 mL, 31.84 mmol) were added and the reaction mixture was heated at 45° C. for 50 min. The reaction mixture was cooled to rt and was stirred with saturated aqueous $NaHCO_3$ (180 mL) for 30 min. The mixture was poured into a separatory funnel containing ether (600 mL). The organic layer was washed with $H_2O$ (4×80 mL), brine, dried over $MgSO_4$, filtered, and concentrated. The residue was purified by column chromatography on silica gel (40% ethyl acetate in hexanes) to give 7-benzyloxymethyl-3-(2,4-dichlorophenyl)-8-ethyl-1-methyl-3,7-dihydro-1H-purine-2,6-dione (5.28 g, 65% yield) as an amorphous solid: $^1H$ NMR (300 MHz, $CDCl_3$) δ 7.59 (d, J=2.2 Hz, 1H), 7.42 (dd, J=8.4, 2.2 Hz, 1H), 7.37–7.26 (m, 6H), 5.86 (ABq, $J_{AB}$=11.0, Δυ=39.7 Hz, 2H), 4.72 (s, 2H), 3.46 (s, 3H), 2.79 (q, J=7.7 Hz, 2H), 1.25 (t, J=7.6 Hz, 3H); LRMS (APCI) m/e 459.0 [(M+H)+, calcd for $C_{22}H_{21}N_4O_3Cl_2$ 459.1].

B. 1-benzyloxymethyl-4-[(2,4-dichlorophenyl)amino]-2-ethyl-N-methyl-1H-imidazole-5-carboxamide 7-benzyloxymethyl-3-(2,4-dichlorophenyl)-8-ethyl-1-methyl-3,7-dihydro-1H-purine-2,6-dione (5.20 g, 11.32 mmol) was dissolved in dioxane (25 mL) and the mixture was treated with EtOH (25 mL) and aqueous NaOH (50 mL, 3 N). The reaction mixture was heated at 60° C. for 2 h. The mixture was then cooled to rt and was transferred to a separatory funnel containing saturated aqueous $NaHCO_3$ (100 mL). The aqueous layer was extracted with EtOAc (3×100 mL). The combined organic layers were washed with brine, dried over $MgSO_4$, filtered, and concentrated. The residue was purified by column chromatography on silica gel (40% ethyl acetate in hexanes→40% ethyl acetate in hexanes with 0.2% MeOH) to afford 1-benzyloxymethyl-4-[(2,4-dichlorophenyl)amino]-2-ethyl-N-methyl-1H-imidazole-5-carboxamide (2.90 g, 59% yield) as a light yellow amorphous solid: $^1H$ NMR (300 MHz, $CDCl_3$) δ 9.35 (s, 1H), 8.41 (d, J=8.8 Hz, 1H), 7.44–7.29 (m, 7H), 7.16 (dd, J=9.1, 2.5 Hz, 1H), 5.45 (s, 2H), 4.63 (s, 2H), 2.89 (d, J=4.8 Hz, 3H); 2.65 (q, J=7.7 Hz, 2H), 1.35 (t, J=7.7 Hz, 3H); LRMS (APCI) m/e 433.1 [(M+H)+, calcd for $C_{21}H_{23}N_4O_2Cl_2$ 433.1].

C. 7-benzyloxymethyl-3-(2,4-dichlorophenyl)-8-ethyl-1-methyl-1,2,3,7-tetrahydro-6H-purin-6-one A solution of 1-benzyloxymethyl-4-[(2,4-dichlorophenyl)amino]-2-ethyl-N-methyl-1H-imidazole-5-carboxamide (2.70 g, 6.23 mmol) dissolved in toluene (100 mL) was treated with paraformaldehyde (8.0 g) and p-TsOH.H$_2$O (0.67 g, 3.52 mmol). The reaction mixture was heated at reflux for 15 min. The mixture was cooled to rt, and transferred to a separatory funnel containing saturated aqueous NaHCO$_3$ (150 mL). The aqueous layer was extracted with EtOAc (3×100 mL). The combined organic layers were washed with brine, dried over MgSO$_4$, filtered, and concentrated. The residue was purified by column chromatography on silica gel (40% ethyl acetate in hexanes) to afford 7-benzyloxymethyl-3-(2,4-dichlorophenyl)-8-ethyl-1-methyl-1,2,3,7-tetrahydro-6H-purin-6-one (1.6 g, 58% yield) as a colorless amorphous solid: $^1$H NMR (300 MHz, CDCl$_3$) δ 7.46 (d, J=2.2 Hz, 1H), 7.34–7.29 (m, 5H), 7.19 (dd, J=8.4, 2.2 Hz, 1H), 7.03 (d, J=8.8 Hz, 1H), 5.84 (s, 2H), 4.85 (s, 2H), 4.71 (s, 2H), 2.97 (s, 3H), 2.77 (q, J=7.7 Hz, 2H), 1.28 (t, J=7.7 Hz, 3H); HRMS (ESI) m/e 445.1212 [(M+H)$^+$, calcd for C$_{22}$H$_{23}$N$_4$O$_2$Cl$_2$ 445.1198].

Example 8

3-(2,4-dichlorophenyl)-8-ethyl-7-[1-(methoxymethyl)butyl]-1-methyl-1,2,3,7-tetrahydro-6H-purin-6-one

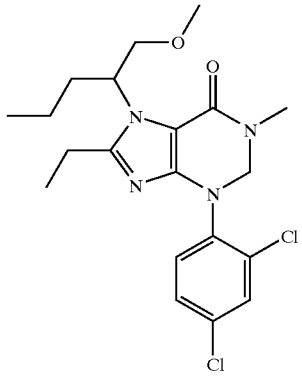

A. 3-(2,4-dichlorophenyl)-8-ethyl-1-methyl-1,2,3,7-tetrahydro-6H-purin-6-one

A solution of 7-benzyloxymethyl-3-(2,4-dichlorophenyl)-8-ethyl-1-methyl-1,2,3,7-tetrahydro-6H-purin-6-one (1.3 g, 2.92 mmol), prepared by the method described in example 7, in CHCl$_3$ (2 mL) was treated with trifluoroacetic acid (15 mL). The solution was heated at 80° C. in a pressure tube for 5 h. The mixture was then cooled to rt and was concentrated. The residue was concentrated from heptane (2×), transferred into a separatory funnel containing saturated aqueous NaHCO$_3$ (75 mL), and the aqueous layer was extracted with EtOAc (3×50 mL). The combined organic layers were washed with brine, dried over MgSO$_4$, filtered, and concentrated. The residue was purified by column chromatography on silica gel (3% methanol in CH$_2$Cl$_2$) to furnish 3-(2,4-dichlorophenyl)-8-ethyl-1-methyl-1,2,3,7-tetrahydro-6H-purin-6-one (900 mg, 95% yield) as a colorless solid: mp 200–201° C.; $^1$H NMR (300 MHz, CDCl$_3$) δ 12.05 (s, 1H), 7.47 (d, J=2.2 Hz, 1H), 7.20 (dd, J=8.8, 2.6 Hz, 1H), 7.12 (d, J=8.4 Hz, 1H), 4.90 (s, 2H), 3.02 (s, 3H), 2.79 (q, J=7.7 Hz, 2H), 1.34 (t, J=7.7 Hz, 3H); LRMS (APCI) m/e 325.0 [(M+H)$^+$, calcd for C$_{14}$H$_{15}$N$_5$OCl$_2$ 325.1].

B. 3-(2,4-dichlorophenyl)-8-ethyl-7-[1-(methoxymethyl)butyl]-1-methyl-1,2,3,7-tetrahydro-6H-purin-6-one A solution of 3-(2,4-dichlorophenyl)-8-ethyl-1-methyl-1,2,3,7-tetrahydro-6H-purin-6-one (80 mg, 0.246 mmol) in anhydrous THF (1.2 mL) was heated to 50° C. PPh$_3$ (100 mg, 0.492 mmol) and 1-methoxy-2-pentanol (87 mg, 0.738 mmol) were added. After stirring 5 min, DEAD (85 µL, 0.541 mmol) was added rapidly via syringe and the reaction mixture was stirred 25 min at 50° C. The mixture was cooled to rt and was poured into a separatory funnel containing saturated aqueous NaHCO$_3$ (15 mL). The aqueous layer was extracted with EtOAc (3×15 mL). The combined organic layers were washed with brine, dried over MgSO$_4$, filtered, and concentrated. Purification of the residue by prep plates (1000 µM silica gel plates, 50% ethyl acetate/50% hexanes) followed by further purification by reverse phase HPLC furnished the title compound (59 mg, 56% yield) as a colorless oil: $^1$H NMR (300 MHz, CDCl$_3$) δ 7.45 (d, J=2.2 Hz, 1H), 7.18 (dd, J=8.5, 2.2 Hz, 1H), 7.07 (d, J=8.4 Hz, 1H), 4.84 (ABq, J=11.4, Δυ=46.9 Hz, 2H), 4.24–4.17 (m, 2H), 3.79–3.74 (m, 1H), 3.32 (s, 3H), 2.96 (s, 3H), 2.75 (q, J=7.7 Hz, 2H), 2.21–2.05 (m, 1H), 1.95–1.81 (m, 1H), 1.30–1.20 (m, 5H), 0.92 (t, J=7.0 Hz, 3H); HRMS (ESI) m/e 425.1519 [(M+H)$^+$, calcd for C$_{20}$H$_{26}$N$_{15}$OCl$_2$ 425.1511].

Example 9

3-(2,4-dichlorophenyl)-8-ethyl-1-methyl-7-[1-(2-propenyl)-3-butenyl]-1,2,3,7-tetrahydro-6H-purin-6-one

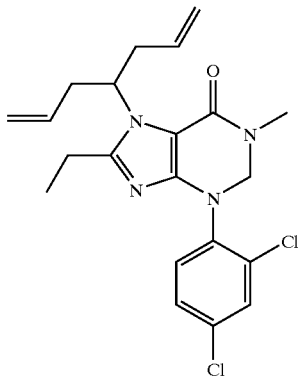

Prepared by the method described in example 8 using the appropriate starting materials except for part "B" to give the desired product. Part "B" was replaced with the following procedure. A solution of 3-(2,4-dichlorophenyl)-8-ethyl-1-methyl-1,2,3,7-tetrahydro-6H-purin-6-one (65 mg, 0.20 mmol) in anhydrous DMF (1.2 mL) was treated with finely ground K$_2$CO$_3$ (83 mg, 0.60 mmol). After stirring 5 min at rt, 4-methanesulfonyl-1,6-heptadiene (203 µL, 1.11 mmol) was added via syringe and the reaction mixture was heated at 90° C. for 4 h. The mixture was cooled to rt and transferred to a separatory funnel containing ether (50 mL). The organic layer was washed with water (4×15 mL), brine (15 mL), dried over MgSO$_4$, filtered, and concentrated. Purification of the residue by prep plate (1000 µM silica gel plate, 25% ethyl acetate in hexanes) followed by further purification by reverse phase HPLC afforded the title compound (15 mg, 18% yield) as a colorless oil; HRMS (ESI) m/e 419.1435 [(M+H)$^+$, calcd for C$_{21}$H$_{25}$N$_4$OCl$_2$ 419.1405].

Example 10

3-(2,4-dichlorophenyl)-1-methyl-7-(3-pentyl)-1,2,3,7-tetrahydro-6H-purin-6-one

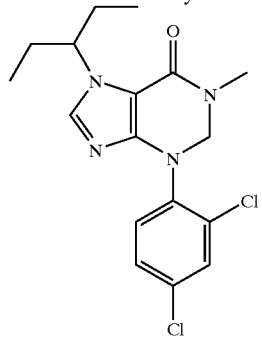

Prepared by the method described in example 1 using the appropriate starting materials to give the desired product as a colorless oil: HRMS (CI) m/e 366.1004 [M+, calcd for $C_{17}H_{20}N_4OCl_2$ 366.1014].

Example 11

3-(2,4-dichlorophenyl)-7-(4-heptyl)-1-methyl-1,2,3,7-tetrahydro-6H-purin-6-one

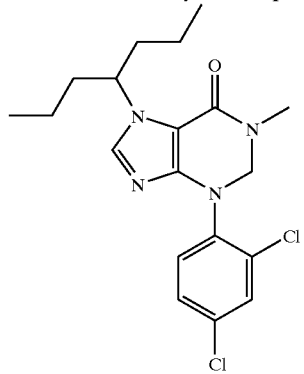

Prepared by the method described in example 1 using the appropriate starting materials to give the desired product as a colorless oil: HRMS (ESI) m/e 395.1420 [(M+H)+, calcd for $C_{19}H_{25}N_4OCl_2$ 395.1405].

Example 12

3-(2,4-dichlorophenyl)-8-ethyl-7-[(4-methoxyphenyl)methyl]-1-methyl-1,2,3,7-tetrahydro-6H-purin-6-one

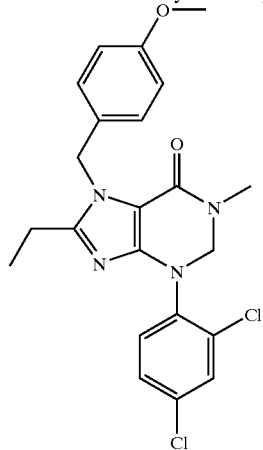

Prepared by the method described in example 1 using the appropriate starting materials to give the desired product as a colorless solid: mp 116.5–117.5° C.; HRMS (ESI) m/e 445.1200 [(M+H)+, calcd for $C_{22}H_{23}N_4O_2Cl_2$ 445.1198].

Example 13

3-(2,4-dichlorophenyl)-7-dicyclopropylmethyl-8-ethyl-1-methyl-1,2,3,7-tetrahydro-6H-purin-6-one

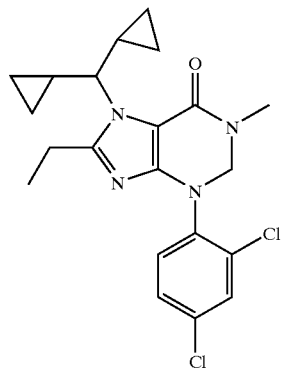

Prepared by the method described in example 8 using the appropriate starting materials to give the desired product as a colorless oil: HRMS (ESI) m/e 419.1402 [(M+H)+, calcd for $C_{21}H_{25}N_4OCl_2$ 419.1405].

Example 14

3-(2,4-dichlorophenyl)-8-ethyl-1-methyl-7-(2-pentyl)-1,2,3,7-tetrahydro-6H-purin-6-one

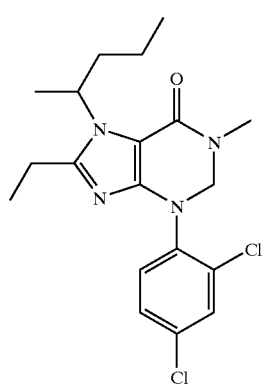

Prepared by the method described in example 8 using the appropriate starting materials to give the desired product as a colorless oil: HRMS (ESI) m/e 395.1386 [(M+H)+, calcd for $C_{19}H_{25}N_4OCl_2$ 395.1405].

Example 15

3-(2,4-dichlorophenyl)-8-ethyl-1-methyl-7-[(2-methylphenyl)methyl]-1,2,3,7-tetrahydro-6H-purin-6-one

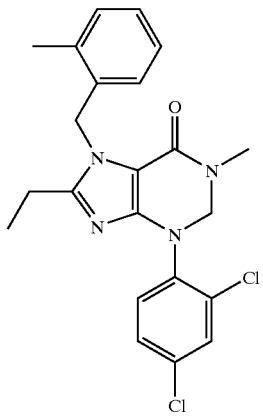

Prepared by the method described in example 8 using the appropriate starting materials to give the desired product as a colorless oil: HRMS (ESI) m/e 429.1249 [(M+H)$^+$, calcd for $C_{22}H_{23}N_4OCl_2$ 429.1249].

Example 16

3-(2,4-dichlorophenyl)-8-ethyl-1-methyl-7-(1-naphthalenylmethyl)-1,2,3,7-tetrahydro-6H-purin-6-one

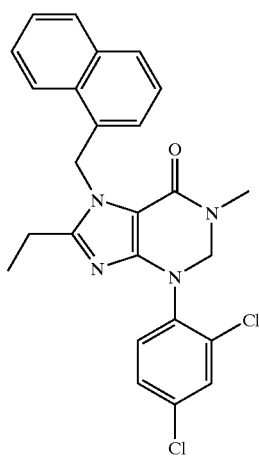

Prepared by the method described in example 8 using the appropriate starting materials to give the desired product as a colorless oil: HRMS (ESI) m/e 465.1248 [(M+H)$^+$, calcd for $C_{25}H_{23}N_4OCl_2$ 465.1249].

Example 17

3-(2,4-dichlorophenyl)-8-ethyl-7-[3-methoxy-1-(2-methoxyethyl)propyl]-1-methyl-1,2,3,7-tetrahydro-6H-purin-6-one

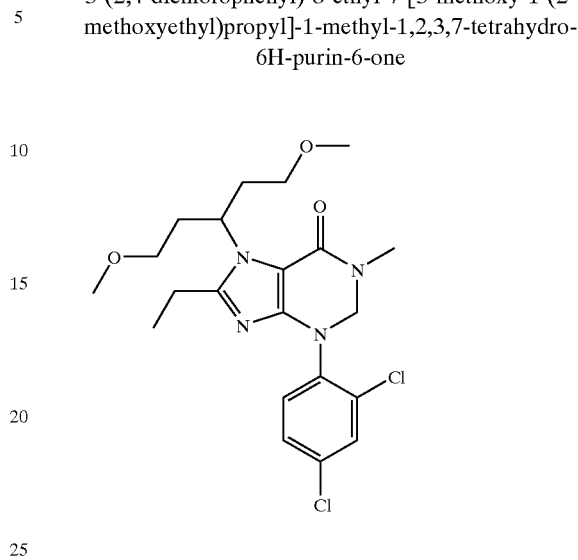

Prepared by the method described in example 8 using the appropriate starting materials to give the desired product as a colorless oil: HRMS (ESI) m/e 456.1637 [(M+H)$^+$, calcd for $C_{21}H_{29}N_4O_3Cl_2$ 456.1616].

Example 18

7-(1-cyclopropylethyl)-3-(2,4-dichlorophenyl)-8-ethyl-1-methyl-1,2,3,7-tetrahydro-6H-purin-6-one

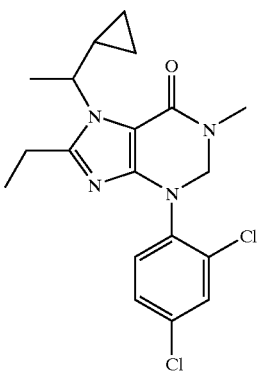

Prepared by the method described in example 8 using the appropriate starting materials to give the desired product as a colorless oil: HRMS (ESI) m/e 393.1244 [(M+H)$^+$, calcd for $C_{19}H_{23}N_4OCl_2$ 393.1249].

Example 19

7-(1-cyclopropylpropyl)-3-(2,4-dichlorophenyl)-8-ethyl-1-methyl-1,2,3,7-tetrahydro-6H-purin-6-one

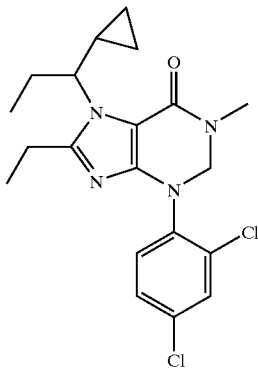

Prepared by the method described in example 8 using the appropriate starting materials to give the desired product as a colorless oil: HRMS (ESI) m/e 407.1423 [(M+H)$^+$, calcd for $C_{20}H_{25}N_4OCl_2$ 407.1405].

Example 20

7-(1-cyclopropylbutyl)-3-(2,4-dichlorophenyl)-8-ethyl-1-methyl-1,2,3,7-tetrahydro-6H-purin-6-one

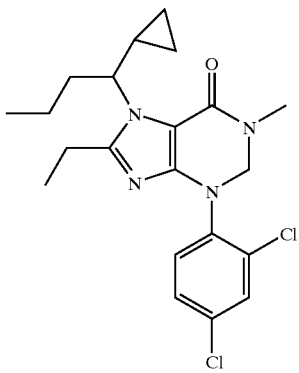

Prepared by the method described in example 8 using the appropriate starting materials to give the desired product as a colorless oil: HRMS (ESI) m/e 421.1567 [(M+H)$^+$, calcd for $C_{21}H_{27}N_4OCl_2$ 421.1562].

Example 21

7-([1,1'-biphenyl]-4-ylmethyl)-3-(2,4-dichlorophenyl)-8-ethyl-1-methyl-1,2,3,7-tetrahydro-6H-purin-6-one

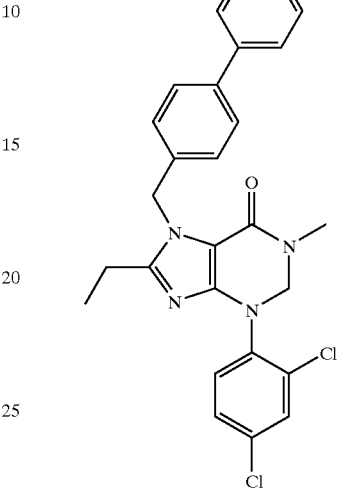

Prepared by the method described in example 8 using the appropriate starting materials to give the desired product as a colorless solid: mp 216–217° C.; HRMS (ESI) m/e 491.1400 [(M+H)$^+$, calcd for $C_{27}H_{25}N_4OCl_2$ 491.1405].

Example 49

3-(2,4-dichlorophenyl)-8-ethyl-7-(3-heptyl)-1-methyl-1,2,3,7-tetrahydro-6H-purin-6-one

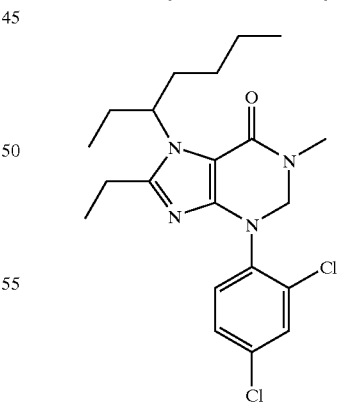

Prepared by the method described in example 1 using the appropriate starting materials to give the desired product as a colorless solid: mp 94–95° C.; HRMS (ESI) m/e 423.1723 [(M+H)$^+$, calcd for $C_{21}H_{29}N_4OCl_2$ 423.1718].

Example 70

3-(2-chloro-4-methoxyphenyl)-8-ethyl-1-methyl-7-(3-pentyl)-1,2,3,7-tetrahydro-6H-purin-6-one

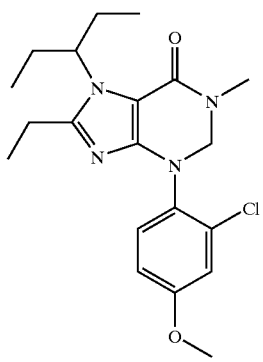

Prepared by the method described in example 8 using the appropriate starting materials to give the desired product. It was necessary to chlorinate the aryl ring after completion of part A (example 1). The following procedure was used.

A suspension of N-(4-methoxyphenyl)-N'-methyl-urea (15.00 g, 83.24 mmol) in $CH_3CN$ (120 mL) was warmed to 65° C. N-chlorosuccinimide (12.22 g, 91.56 mmol) was added and the reaction mixture was heated at 90° C. for 40 min. The mixture was cooled to 0° C., and the solid was collected on a Buchner funnel to afford the desired product (13.5 g, 75% yield) as a colorless solid: mp 184–185° C.; $^1$H NMR (300 MHz, $CDCl_3$) δ 7.85 (d, J=9.2 Hz, 1H), 7.81 (s, 1H), 7.00 (d, J=2.9 Hz, 1H), 6.86 (dd, J=9.1, 2.1 Hz, 1H), 6.58–6.57 (m, 1H), 3.72 (s, 3H), 2.63 (d, J=4.8 Hz, 3H); LRMS (APCI) m/e 215.0 [(M+H)$^+$, calcd for $C_9H_{12}N_2O_2Cl$ 215.1].

The preparation of example 70 was completed using the method described in example 8 to give the desired product as a colorless oil: HRMS (ESI) m/e 391.1904 [(M+H)$^+$, calcd for $C_{20}H_{28}N_4O_2Cl$ 391.1901].

Example 71

3-(2-chloro-4-methoxyphenyl)-8-ethyl-7-(4-heptyl)-1-methyl-1,2,3,7-tetrahydro-6H-purin-6-one

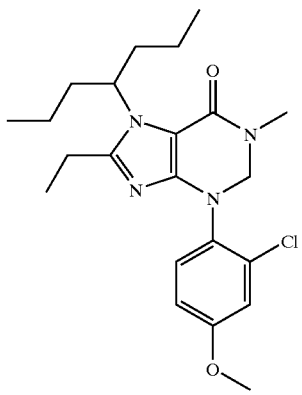

Prepared by the method described in example 9 and the chlorination procedure described in example 70 using the appropriate starting materials to give the desired product as a colorless oil: HRMS (ESI) m/e 419.2215 [(M+H)$^+$, calcd for $C_{22}H_{32}N_4O_2Cl$ 419.2214].

Example 72

3-(2-chloro-4-methoxyphenyl)-8-ethyl-1-methyl-7-(2-pentyl)-1,2,3,7-tetrahydro-6H-purin-6-one

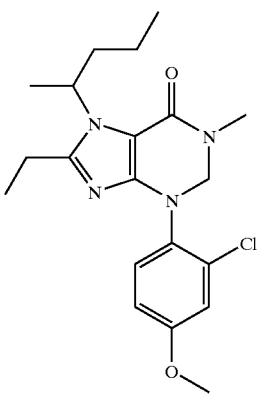

Prepared by the method described in example 70 using the appropriate starting materials to give the desired product as a colorless oil: HRMS (ESI) m/e 391.1920 [(M+H)$^+$, calcd for $C_{20}H_{28}N_4O_2Cl$ 391.1901].

Example 73

3-(2-chloro-4-methoxyphenyl)-8-ethyl-7-[1-(methoxymethyl)butyl]-1-methyl-1,2,3,7-tetrahydro-6H-purin-6-one

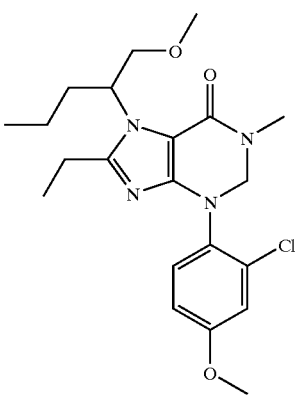

Prepared by the method described in example 70 using the appropriate starting materials to give the desired product as a colorless oil: HRMS (ESI) m/e 421.1871 [(M+H)$^+$, calcd for $C_{21}H_{30}N_4O_3Cl$ 421.2006].

Example 74

3-(2-chloro-4-methoxyphenyl)-7-(1-cyclopropylpropyl)-8-ethyl-1-methyl-1,2,3,7-tetrahydro-6H-purin-6-one

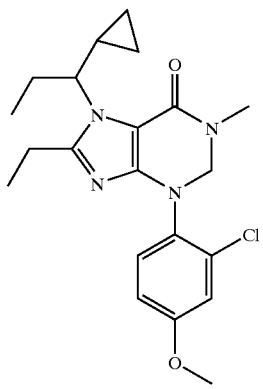

Prepared by the method described in example 70 using the appropriate starting materials to give the desired product as a colorless oil: HRMS (ESI) m/e 403.2015 [(M+H)$^+$, calcd for $C_{21}H_{27}N_4O_2Cl$ 403.1901].

Example 75

7-([1,1'-biphenyl]-4-ylmethyl)-3-(2-chloro-4-methoxyphenyl)-8-ethyl-1-methyl-1,2,3,7-tetrahydro-6H-purin-6-one

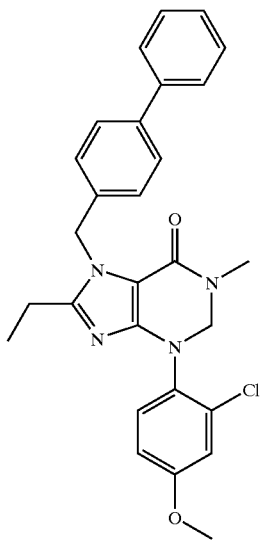

Prepared by the method described in example 70 using the appropriate starting materials to give the desired product as a colorless amorphous solid: HRMS (ESI) m/e 487.1893 [(M+H)$^+$, calcd for $C_{28}H_{28}N_4O_2Cl$ 487.1901].

Example 77

3-(2-chloro-4-methoxyphenyl)-8-ethyl-1-methyl-7-[(2-methylphenyl)methyl]-1,2,3,7-tetrahydro-6H-purin-6-one

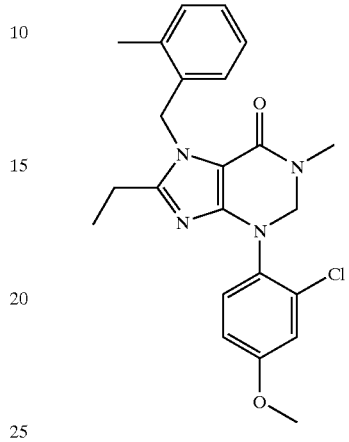

Prepared by the method described in example 70 using the appropriate starting materials to give the desired product as a colorless oil: HRMS (ESI) m/e 425.1738 [(M+H)$^+$, calcd for $C_{23}H_{26}N_4O_2Cl$ 425.1744].

Example 81

3-(2-chloro-4-methoxyphenyl)-7-(1-cyclopropylbutyl)-8-ethyl-1-methyl-1,2,3,7-tetrahydro-6H-purin-6-one

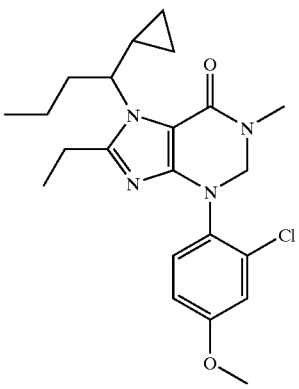

Prepared by the method described in example 70 using the appropriate starting materials to give the desired product as a colorless oil: HRMS (ESI) m/e 417.2053 [(M+H)$^+$, calcd for $C_{22}H_{30}N_4O_2Cl$ 417.2057].

Example 85

3-(2-chloro-4-methoxyphenyl)-7-(1-cyclobutylethyl)-8-ethyl-1-methyl-1,2,3,7-tetrahydro-6H-purin-6-one

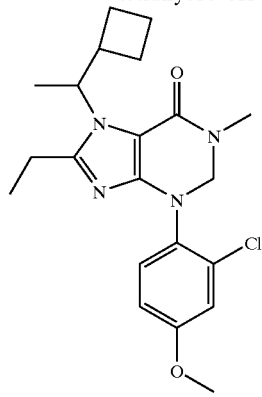

Prepared by the method described in example 70 using the appropriate starting materials to give the desired product as a colorless oil: HRMS (ESI) m/e 403.1915 [(M+H)$^+$, calcd for $C_{21}H_{28}N_4O_2Cl$ 403.1901].

Example 116

3-[2-chloro-4-isopropylphenyl]-8-ethyl-7-(4-heptyl)-1-methyl-1,2,3,7-tetrahydro-6H-purin-6-one

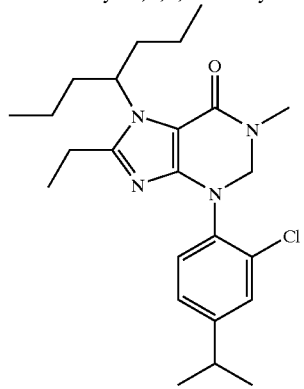

Prepared by the method described in example 71 using the appropriate starting materials to give the desired product as a colorless oil: HRMS (ESI) m/e 431.2581 [(M+H)$^+$, calcd for $C_{24}H_{36}N_4OCl$ 431.2578].

Example 133

3-[2-chloro-4-(isopropylphenyl]-8-ethyl-7-(1-ethyl-2-methylpropyl)-1-methyl-1,2,3,7-tetrahydro-6H-purin-6-one

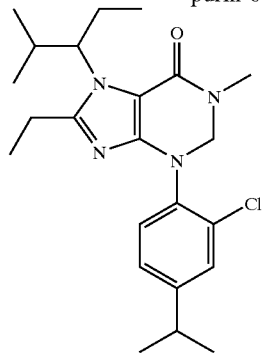

Prepared by the method described in example 71 using the appropriate starting materials to give the desired product as a colorless oil: HRMS (ESI) m/e 417.2420 [(M+H)$^+$, calcd for $C_{23}H_{34}N_4OCl$ 417.2421].

Example 144

8-ethyl-7-(4-heptyl)-1-methyl-3-(2,4,6-trimethylphenyl)-1,2,3,7-tetrahydro-6H-purin-6-one

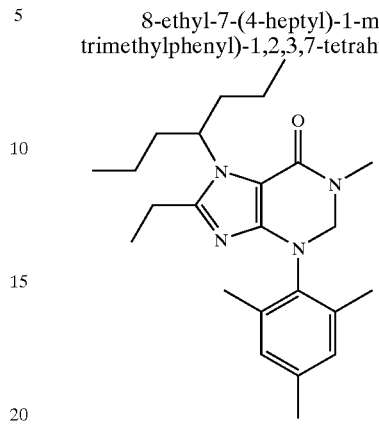

Prepared by the method described in example 9 using the appropriate starting materials to give the desired product as a colorless oil: HRMS (ESI) m/e 397.2965 [(M+H)$^+$, calcd for $C_{24}H_{37}N_4O$ 397.2967].

Example 161

8-ethyl-7-(1-ethyl-2-methylpropyl)-1-methyl-3-(2,4,6-trimethylphenyl)-1,2,3,7-tetrahydro-6H-purin-6-one

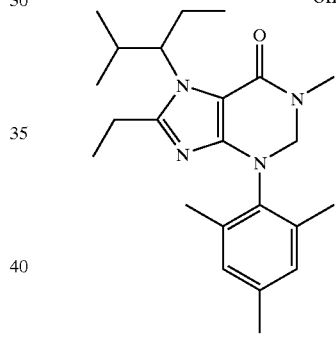

Prepared by the method described in example 9 using the appropriate starting materials to give the desired product as a colorless oil: HRMS (ESI) m/e 383.2808 [(M+H)$^+$, calcd for $C_{23}H_{35}N_4O$ 383.2811].

Example 196

8-ethyl-7-(4-heptyl)-3-(4-methoxy-2-methylpyrid-3-yl)-1-methyl-1,2,3,7-tetrahydro-6H-purin-6-one

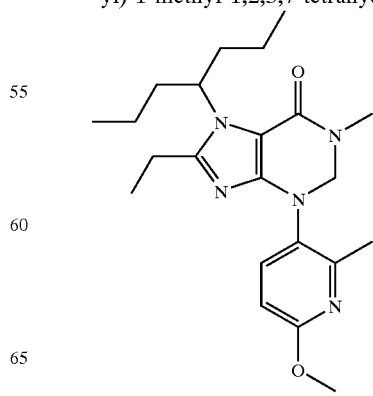

A. 8-ethyl-7-(4-heptyl)-3-[(4-methoxyphenyl)methyl]-1-methyl-3,7-dihydro-1H-purine-2,6-dione 8-ethyl-7-(4-heptyl)-3-[(4-methoxyphenyl)methyl]-1-methyl-3,7-dihydro-1H-purine-2,6-dione was prepared according to the procedure described in example 1 (P=PMB) to give a colorless solid; mp 120.5–121.5° C.; $^1$H NMR (300 MHz, CDCl$_3$) δ 7.56 (d, J=8.4 Hz, 2H), 6.85 (d, J=8.8 Hz, 2H), 5.22 (s, 2H), 4.15–4.04 (m, 1H), 3.78 (s, 3H), 3.39 (s, 3H), 2.78 (q, J=7.4 Hz, 2H), 2.27–2.18 (m, 2H), 1.88–1.78 (m, 2H), 1.41 (t, J=7.4 Hz, 3H), 1.25–1.00 (m, 4H), 0.88 (t, J=7.3 Hz, 6H); LRMS (APCI) m/e 825.3 [(2M+H)$^+$, calcd for C$_{42}$H$_{65}$N$_8$O$_6$ 825.5].

B. 8-ethyl-7-(4-heptyl)-1-methyl-3,7-dihydro-1H-purine-2,6-dione

A solution of 8-ethyl-7-(4-heptyl)-3-[(4-methoxyphenyl)methyl]-1-methyl-3,7-dihydro-1H-purine-2,6-dione (4.30 g, 10.4 mmol) in trifluoroacetic acid (20 mL) was heated at 105° C. in a sealed tube for 14 h. The mixture was cooled to rt and concentrated. The residue was transferred to a separatory funnel containing saturated aqueous NaHCO$_3$ (50 mL) and the aqueous layer was extracted with EtOAc (3×50 mL). The combined organic layers were washed with brine, dried over MgSO$_4$, filtered, and concentrated. The residue was purified by column chromatography on silica gel (5% methanol in CH$_2$Cl$_2$) to afford 8-ethyl-7-(4-heptyl)-1-methyl-3,7-dihydro-1H-purine-2,6-dione (2.96 g, 97% yield) as a colorless solid: mp 152.5–153° C.; $^1$H NMR (300 MHz, CDCl$_3$) δ 12.00 (s, 1H), 4.20–4.10 (m, 1H), 3.41 (s, 3H), 2.94 (q, J=7.3 Hz, 2H), 2.33–2.19 (m, 2H), 1.94–1.83 (m, 2H), 1.42 (t, J=7.4 Hz, 3H), 1.26–1.06 (m, 4H), 0.90 (t, J=7.3 Hz, 6H); LRMS (APCI) m/e 293.1 [(M+H)$^+$, calcd for C$_{15}$H$_{25}$N$_4$O$_2$ 293.2].

C. 8-ethyl-7-(4-heptyl)-3-(4-methoxy-2-methylpyrid-3-yl)-1-methyl-3,7-dihydro-1H-purine-2,6-dione 8-ethyl-7-(4-heptyl)-1-methyl-3,7-dihydro-1H-purine-2,6-dione (3.30 g, 11.3 mmol), 6-methoxy-2-methyl-3-pyridineboronic acid (2.84 g, 17.0 mmol), copper (II) acetate (3.07 g, 17 mmol), and 4 Å powdered molecular sieves (3.0 g) were combined in a 200 mL round bottom flask. CH$_2$Cl$_2$ (25 mL) and pyridine (1.81 mL, 22.6 mmol) were added and the reaction mixture was stirred at rt for 2 days. Additional 6-methoxy-2-methyl-3-pyridineboronic acid (1.50 g, 8.98 mmol) and copper (II) acetate (2.0 g, 11.0 mmol) was added and the reaction mixture was stirred at rt for an additional 2 days. The mixture was poured into a separatory funnel containing saturated aqueous NH$_4$Cl (100 mL) and conc NH$_4$OH (150 mL). The aqueous layer was extracted with EtOAc (4×100 mL). The combined organic layers were washed with brine, dried over MgSO$_4$, filtered, and concentrated. The residue was purified by column chromatography on silica gel (30% ethyl acetate in hexanes then 75% ethyl acetate/25% hexanes to recover starting material) to furnish 8-ethyl-7-(4-heptyl)-3-(4-methoxy-2-methylpyrid-3-yl)-1-methyl-3,7-dihydro-1H-purine-2,6-dione (1.92 g, 41% yield) and recovered starting material (1.72 g, 52% recovery). The product was isolated as a colorless solid: 87–94° C.; $^1$H NMR (300 MHz, CDCl$_3$) δ 7.45 (d, J=8.4 Hz, 1H), 6.68 (d, J=8.4 Hz, 1H), 4.17–4.08 (m, 1H), 3.95 (s, 3H), 3.47 (s, 3H), 2.73 (q, J=7.3 Hz, 2H), 2.32–2.23 (m, 1H), 2.25 (s, 3H), 1.98–1.80 (m, 3H), 1.30–1.05 (m, 4H), 1.24 (t, J=7.3 Hz, 3H), 0.94–0.88 (m, 6H); LRMS (APCI) m/e 414.6 [(M+H)$^+$, calcd for C$_{22}$H$_{32}$N$_5$O$_3$ 414.3].

D. 8-ethyl-7-(4-heptyl)-3-(4-methoxy-2-methylpyrid-3-yl)-1-methyl-1,2,3,7-tetrahydro-6H-purin-6-one 8-ethyl-7-(4-heptyl)-3-(4-methoxy-2-methylpyrid-3-yl)-1-methyl-3,7-dihydro-1H-purine-2,6-dione (1.84 g, 4.46 mmol) was dissolved in THF (50 mL) and was cooled to 0° C. Lithium aluminum hydride (8.92 mL, 8.92 mmol, 1 M in THF) was added dropwise via syringe. The cooling bath was removed and the reaction mixture was stirred at rt for 30 min. The reaction mixture was cooled to 0° C. and was quenched by the dropwise addition of H$_2$O (0.34 mL) followed by 15% aqueous NaOH (0.34 mL) then H$_2$O (1.02 mL). The mixture was filtered through a pad of Celite and was washed with EtOAc. The filtrate was poured into a separatory funnel containing saturated aqueous NaHCO$_3$ (50 mL). The layers were separated and the aqueous layer was extracted with EtOAc (3×50 mL). The combined organic layers were washed with brine, dried over MgSO$_4$, filtered, and concentrated. Two major products were formed in the reaction. The crude material was purified by column chromatography on silica gel (30% ethyl acetate in hexanes to elute the higher rf product then 50% ethyl acetate in hexanes to elute the lower rf product) to afford the higher rf product (306 mg) and the lower rf product 2-ethyl-1-(4-heptyl)-4-[(4-methoxy-2-methylpyrid-3-yl)amino]-N-methyl-1H-imidazole-5-carboxamide, 800 mg, 46% yield) as a green oil. The higher rf product was purified further by column chromatography on silica gel (2% MeOH in CH$_2$Cl$_2$) to afford 8-ethyl-7-(4-heptyl)-3-(4-methoxy-2-methylpyrid-3-yl)-1-methyl-1,2,3,7-tetrahydro-6H-purin-6-one (240 mg, 14% yield) as a pale green solid.

Data for 2-ethyl-1-(4-heptyl)-4-[(4-methoxy-2-methylpyrid-3-yl)amino]-N-methyl-1H-imidazole-5-carboxamide: green oil; $^1$H NMR (300 MHz, CDCl$_3$) δ 7.14 (s br, 1H), 7.01 (d br, J=7.3H, 1H), 6.47 (d, J=8.5 Hz, 1H), 5.42 (s br, 1H), 4.15–4.05 (m, 1H), 3.87 (s, 3H), 2.77 (d, J=5.1 Hz, 3H), 2.73 (q, J=7.3 Hz, 2H), 2.45 (s, 3H), 1.90–1.75 (m, 4H), 1.31 (t, J=7.3 Hz, 3H), 1.40–1.23 (m, 2H), 1.22–1.10 (m, 2H), 0.91 (t, J=7.4 Hz, 6H); LRMS (APCI) m/e 388.3 [(M+H)$^+$, calcd for C$_{21}$H$_{34}$N$_5$O$_2$ 388.3].

Data for 8-ethyl-7-(4-heptyl)-3-(4-methoxy-2-methylpyrid-3-yl)-1-methyl-1,2,3,7-tetrahydro-6H-purin-6-one: pale green solid; 120–122° C.; $^1$H NMR (300 MHz, CDCl$_3$) δ 7.26 (d, J=8.4 Hz, 1H), 6.54 (d, J=8.0 Hz, 1H), 4.64 (s, 2H), 3.91 (s, 3H), 2.96 (s, 3H), 2.68 (q, J=7.7 Hz, 2H), 2.48 (s, 3H), 2.30–2.10 (m, 2H), 1.95–1.80 (m, 2H), 1.37–1.15 (m, 4H), 1.24 (t, J=7.7 Hz, 3H), 0.92 (t, J=7.3 Hz, 6H); HRMS (ESI) m/e 400.2715 [(M+H)$^+$, calcd for C$_{22}$H$_{34}$N$_5$O$_2$ 400.2713].

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below.

Individual aliquots containing approximately 1×10⁸ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 µg/l aprotinin, 1 µg/ml leupeptin and 1 µg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 µg/ml to be used in the assay.

Binding assays are performed in 96 well plates; each well having a 300 µl capacity. To each well is added 50 µl of test drug dilutions (final concentration of drugs range from $10^{-10}$–$10^{-5}$ M), 100 µl of $^{125}$I-ovine-CRF (125I-o-CRF) (final concentration 150 pM) and 150 µl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a Ki value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions are initiated by the addition of 1 mM ATP/$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990).

Compounds may be tested in any species of rodent or small mammal.

Compounds of this invention have utility in the treatment of disorder and imbalances associated with abnormal levels, such as elevated levels due to hypersecretion or overexpression, of corticotropin releasing factor in patients. Thus, the present invention provides methods of treating a mammal having a disorder characterized by hypersecretion or overexpression of corticotropin releasing factor comprising administering to said mammal a therapeutically effective amount of a compound of Formula (I).

Some disorders characterised by abnormal levels of corticotropin releasing factor include depression, affective disorders, and anxiety. Some other disorders characterized by abnormal levels of CRF include, for example, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal. Thus, compounds provided herein which, because of their antagonism of CRF receptors, can alleviate the effects of CRF overexpression are expected to be useful in treating these and other disorders.

Compounds of this invention can be administered to treat the above disorders by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

The compounds of this invention may also be used as reagents or standards in the biochemical study of neurological function, dysfunction, and disease.

As those skilled in the art will appreciate, numerous changes and modifications can be made to the preferred embodiments of the invention without departing from the spirit of the invention. It is intended that all such variations fall within the scope of the invention. Throughout this specification, various groupings are employed to conveniently describe constituent variables of compounds and groups of various related moieties. It is specifically intended that each occurrence of such groups throughout this specification include every possible subcombination of the members of the groups, including the individual members thereof.

It is intended that each of the patents, applications, and printed publications mentioned in this patent document be hereby incorporated by reference in its entirety.

What is claimed is:

1. A compound of Formula (I):

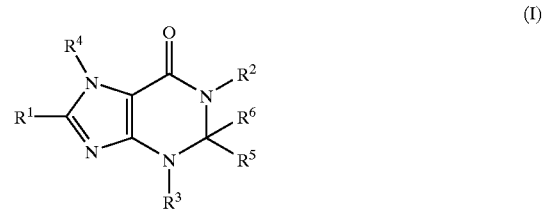

or a pharmaceutically acceptable salt form thereof, wherein:

$R^1$ is H, $C_1$–$C_4$ alkyl substituted with 0–3 $X^1$, $C_3$–$C_8$ cycloalkyl substituted with 0–3 $X^1$, $C_2$–$C_4$ alkenyl substituted with 0–3 $X^1$, or $C_2$–$C_4$ alkynyl substituted with 0–3 $X^1$;

each $X^1$ is, independently at each occurrence, CN, hydroxy, halo, or $C_1$–$C_4$ alkoxy;

alternatively, $R^1$ is CN, $C_1$–$C_4$ haloalkyl, $C_1$–$C_6$ alkyl-$NR^{1a}R^{1b}$, $NR^{1a}C(O)R^{1b}$, $C(o)NR^{1a}R^{1b}$, $OR^{1a}$, $S(O)_nR^{1a}$, or $OC(O)R^{1a}$;

each $R^{1a}$ and $R^{1b}$ is, independently, H, $C_1$–$C_4$ alkyl substituted with 0–3 $X^2$, or $C_3$–$C_6$ cycloalkyl substituted with 0–3 $X^2$;

each $X^2$ is, independently, at each occurrence, CN, hydroxy, halo, or $C_1$–$C_4$ alkoxy;

n is 0, 1 or 2;

$R^2$ is H, $C_1$–$C_6$ alkyl substituted with 0 to 4 $X^3$, $C_3$–$C_7$ cycloalkyl substituted with 0 to 4 $X^3$, $C_3$–$C_6$-cycloalkyl-$C_1$–$C_6$ alkyl substituted with 0 to 4 $X^3$, $C_3$–$C_6$-alkenyl substituted with 0 to 4 $X^3$, $C_3$–$C_6$-alkynyl substituted with 0 to 4 $X^3$, aryl substituted with 0 to 4 $X^3$, heteroaryl substituted with 0 to 4 $X^3$, or $C_5$–$C_8$ cycloalkenyl substituted with 0 to 4 $X^3$;

each $X^3$ is, independently at each occurrence, halogen, OH, $C_2$–$C_4$ alkenyl, $C_2$–$C_4$ alkynyl, $C_2$–$C_4$ cycloalkyl, $C_1$–$C_4$ haloalkyl, $CO_2R^7$ $OC(O)R^7$, $COR^7$, $OC(O)OR^7$, $CO_2H$, $OR^7$, $NR^8R^9$, $NR^7COR^9$, $NHR^7SO_2R^9$, $OC(O)NR^7R^8$, $N(COR^7)_2$, $NR^7CONR^8R^9$, $NR^7CO_2R^9$, $CONR^7R^9$, $S(O)_nR^7$, $SO_2NR^7R^9$, SN, CN, aryl, heteroaryl, or heterocyclyl;

$R^3$ is aryl substituted with 0–5 $X^{Ar}$ or heteroaryl substituted with 0–4 $X^{hAr}$;

each $X^{Ar}$ is, independently at each occurrence, phenyl, $C_1$–$C_6$ alkyl, $C_3$–$C_6$ cycloalkyl, methylenedioxy, $C_1$–$C_4$ alkoxy-$C_1$–$C_4$ alkoxy, $OR^{15}$, Br, Cl, F, I, $C_1$–$C_4$ haloalkyl, CN, $NO_2$, SN, $S(O)_nR^{16}$, $COR_{15}$, $CO_2R^{15}$, $OC(O)R^{16}$, $NR^{20}COR^{15}$, $N(COR^{15})_2$, $NR^{20}CONR^{15}R^{17}$, $NR^{20}CO_2R^{16}$, $NR^{15}R^{17}$, or $CONR^{15}R^{17}$;

each $X^{hAr}$ is, independently at each occurrence, $C_1$–$C_6$ alkyl, $C_3$–$C_6$ cycloalkyl, Br, Cl, F, I, $C_1$–$C_4$ haloalkyl, CN, nitro, $OR^{15}$, SH, $S(O)_nR^{16}$, $COR^{15}$, $CO_2R^{15}$, $OC(O)R^{16}$, $NR^{20}COR^{15}$, $N(COR^{15})_2$, $NR^{20}CONR^{15}R^{17}$, $NR^{20}CO_2R^{16}$, $NR^{15}R^{17}$, $CONR^{15}R^{17}$, $R^{20}$, $CO_2R^{21}$, $COR^2$, or $SO_2R^{21}$;

$R^4$ is $C_1$–$C_{10}$ alkyl substituted with 0–1 $X^4$ or 0–3 $X^5$, $C_2$–$C_{10}$ alkenyl substituted with 0–1 $X^4$ or 0–3 $X^5$, $C_2$–$C_{10}$ alkynyl substituted with 0–1 $X^4$ or 0–3 $X^5$, $C_3$–$C_8$ cycloalkyl substituted with 0–1 $X^4$ or 0–3 $X^5$, $C_3$–$C_6$ cycloalkyl-$C_1$–$C_6$ alkyl substituted with 0–1 $X^4$ or 0–3 $X^5$, $C_1$–$C_4$ alkoxy-$C_{1-4}$alkyl substituted with 0–1 $X^4$ or 0–3 $X^5$, aryl substituted with 0–1 $X^4$ or 0–3 $X^5$, heteroaryl substituted with 0–1 $X^4$ or 0–3 $X^5$, heterocyclyl substituted with 0–1 $X^4$ or 0–3 $X^5$, or aryl-$C_1$–$C_4$ alkyl substituted with 0–1 $X^4$ or 0–3 $X_5$;

each $X^4$ is, independently at each occurrence, CN, $S(O)_nR^{11}$, $COR^{12}$, $CO_2R^{12}$, $NR^{13}COR^{12}$, $N(COR^{12})_2$, $NR^{13}CONR^{12}R^{14}$, $NR^{13}CO_2R^{11}$, $CONR^{12}R^{14}$, 1-naphthalenyl, 1-morpholinyl, 1-piperidinyl, 1-piperazinyl, or $C_{3-8}$ cycloalkyl, wherein 0–1 carbon atoms in said $C_{3-8}$ cycloalkyl is replaced by a group selected from the group consisting of $-S(O)_n-$, $-NR^{12}-$, $-NCO_2R^{11}-$, $-NCOR^{11}-$ and $-NSO_2R^{11}-$, and wherein $N^4$ in 1-piperazinyl is substituted with 0–1 substituents selected from the group consisting of $R^{12}$, $CO_2R^{11}$, $COR^{11}$ and $SO_2R^{11}$;

each $X^5$ is, independently at each occurrence, aryl, heteroaryl, heterocyclyl, $C_1$–$C_6$ alkyl, $C_2$–$C_8$ alkenyl, $C_2$–$C_8$ alkynyl, Br, Cl, F, I, $C_{1-4}$ haloalkyl, $OR^{12}$, $NR^{12}R^{14}$, $C_1$–$C_4$ alkoxy-$C_1$–$C_4$ alkyl substituted with 0–1 $R^{10}$, or $C_3$–$C_8$ cycloalkyl optionally substituted with 0–1 $R^{10}$, and wherein 0–1 carbon atoms in said $C_3$–$C_8$ cycloalkyl is replaced by $-O-$;

each $R^5$ and $R^6$ is, independently, H, $C_1$–$C_4$ alkyl, $C_3$–$C_4$ alkenyl, or $C_3$–$C_4$ alkynyl;

each $R^7$ is, independently at each occurrence, H, $C_1$–$C_4$ alkyl substituted with 0–2 $X^6$, $C_3$–$C_6$ cycloalkyl substituted with 0–2 $X^6$, $C_3$–$C_4$ alkenyl substituted with 0–2 $X^6$, $C_3$–$C_4$ alkynyl substituted with 0–2 $X^6$, $C_1$–$C_4$ haloalkyl substituted with 0–2 $X^6$, $C_1$–$C_4$ alkyloxy-$C_1$–$C_4$ alkyl substituted with 0–2 $X^6$ or $C_3$–$C_6$ cycloalkyl-$C_1$–$C_4$ alkyl substituted with 0–2 $X^6$, wherein one carbon atom in any cycloalkyl ring is optionally replaced with O, S or $NR^8$;

each $X^6$ is, independently at each occurrence, OH, $C_1$–$C_4$ alkoxy, or halogen;

$R^8$ is H, $C_1$–$C_4$ alkyl, $C_3$–$C_6$ cycloalkyl, $C_3$–$C_6$ cycloalkyl-$C_1$–$C_4$ alkyl, or $C_1$–$C_4$ haloalkyl;

$R^9$ is H, $C_1$–$C_4$ alkyl substituted with 0–2 $X^7$, $C_3$–$C_6$ cycloalkyl substituted with 0–2 $X^7$, $C_3$–$C_4$ alkenyl substituted with 0–2 $X^7$, $C_3$–$C_4$ alkynyl substituted with 0–2 $X^7$, $C_1$–$C_4$ haloalkyl substituted with 0–2 $X^7$, aryl substituted with 0–2 $X^7$, $C_1$–$C_4$ alkyloxy-$C_1$–$C_4$ alkyl substituted with 0–2 $X^7$, or $C_3$–$C_6$ cycloalkyl-$C_1$–$C_4$ alkyl substituted with 0–2 $X^7$, wherein one carbon in any cycloalkyl ring is optionally replaced with O, S or $NR^8$;

each $X^7$ is, independently at each occurrence, $C_1$–$C_4$ alkoxy or halogen;

$R^{10}$ is H, $C_1$–$C_4$ alkyl, $C_3$–$C_6$ cycloalkyl-$C_1$–$C_4$ alkyl, or $C_3$–$C_8$ cycloalkyl;

$R^{11}$ is $C_1$–$C_4$ alkyl, $C_1$–$C_4$ haloalkyl, $C_1$–$C_4$ alkoxy-$C_1$–$C_4$ alkyl, $C_3$–$C_6$ cycloalkyl, or $C_3$–$C_6$ cycloalkyl-$C_{1-6}$ alkyl;

$R^{12}$ is H, benzyl, aryl, $C_1$–$C_4$ alkyl, $C_1$–$C_4$ haloalkyl, $C_1$–$C_4$ alkoxy-$C_1$–$C_4$ alkyl, $C_3$–$C_6$ cycloalkyl, or $C_3$–$C_6$ cycloalkyl-$C_{1-6}$ alkyl;

$R^{13}$ is H, $C_1$–$C_4$ alkyl, $C_3$–$C_7$ cycloalkyl, or $C_3$–$C_6$ cycloalkyl-$C_1$–$C_6$ alkyl;

$R^{14}$ is H, $C_1$–$C_4$ alkyl, $C_1$–$C_4$ haloalkyl, $C_1$–$C_4$ alkoxy-$C_1$–$C_4$ alkyl, $C_3$–$C_6$ cycloalkyl, or $C_3$–$C_6$ cycloalkyl-$C_1$–$C_6$ alkyl;

$R^{15}$ is H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-4}$ alkyl, $C_{1-4}$ haloalkyl, $R^{18}S(O)_n-C_{1-4}$ alkyl, or $R^{11}R^{12}N-C_{2-4}$ alkyl;

each $R^{16}$ and $R^{17}$ is, independently at each occurrence, H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, or $C_{1-4}$ haloalkyl;

alternatively, in an $NR^{15}R^{17}$ moiety, $R^{15}$ and $R^{17}$ are taken together with the nitrogen atom to which they are both attached to form 1-pyrrolidinyl, 1-morpholinyl, 1-piperidinyl, or 1-piperazinyl, wherein $N^4$ in 1-piperazinyl is substituted with 0–1 substituents selected from the group consisting of $R^{19}$, $CO_2R^{18}$, $COR^{18}$ and $SO_2R^{18}$;

$R^{18}$ is $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl-$C_{1-4}$ alkyl, heteroaryl, or heteroaryl-$C_{1-4}$ alkyl, wherein said aryl-$C_{1-4}$ alkyl is substituted with 0–1 substituents selected from the group consisting of $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{19}$ is H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl-$C_{1-4}$ alkyl, heteroaryl, or heteroaryl-$C_{1-4}$ alkyl;

$R^{20}$ is H, $C_{1-4}$ alkyl, $C_{3-7}$ cycloalkyl, $C_{3-6}$ cycloalkyl-$C_{1-6}$ alkyl, aryl substituted with 0–3 $X^8$, or aryl-$C_1$–$C_4$ alkyl substituted with 0–3 $X^8$;

each $X^8$ is, independently at each occurrence, $C_{1-4}$ alkyl, Br, Cl, F, I, $C_{1-4}$ haloalkyl, nitro, $C_{1-4}$ alkoxy, $C_{1-4}$ haloalkoxy, or dimethylamino;

$R^{21}$ is $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, or aryl-$C_1$–$C_4$ alkyl, wherein said aryl-$C_1$–$C_4$ alkyl is substituted with 0–1 $X^9$; and each $X^9$ is, independently at each occurrence, $C_{1-4}$ alkyl, Br, Cl, F, I, $C_{1-4}$ haloalkyl, nitro, $C_{1-4}$ alkoxy, $C_{1-4}$ haloalkoxy, or dimethylamino.

2. A compound according to claim 1 wherein $R^1$ is $C_1$–$C_4$ alkyl, $C_3$–$C_8$ cycloalkyl, $C_2$–$C_4$ alkenyl, or $C_2$–$C_4$ alkynyl.

3. A compound according to claim 1 wherein $R^1$ is $OR^{1a}$ and $R^{1a}$ is $C_1$–$C_4$ alkyl.

4. A compound according to claim 1 wherein $R^2$ is $C_1$–$C_6$ alkyl or $C_3$–$C_7$ cycloalkyl.

5. A compound according to claim 1 wherein $R^3$ is phenyl, naphthyl, indanyl, or indenyl, wherein said $R^3$ is substituted with 0–5 $X^{Ar}$.

6. A compound according to claim 1 wherein $R^3$ is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, indolinyl, benzodioxolanyl, or benzodioxanyl, wherein $R^3$ is substituted with 0–4 $X^{hAr}$.

7. A compound according to claim 1 wherein $R^3$ is phenyl substituted with 0–5 $X^{Ar}$ or pyridyl substituted with 0–4 $X^{hAr}$.

8. A compound according to claim 1 wherein $R^4$ is $C_1$–$C_{10}$ alkyl, $C_3$–$C_8$ cycloalkyl, or benzyl.

9. A compound according to claim 1 wherein each $R^5$ and $R^6$ is, independently, H or $C_1$–$C_4$ alkyl.

10. A compound according to claim 1 wherein $X^{Ar}$ is phenyl, $C_1$–$C_6$ alkyl, $OR^{15}$, Br, Cl, F, I, or $C_1$–$C_4$ haloalkyl.

11. A compound according to claim 1 wherein $X^{hAr}$ is Br, Cl, F, I, $C_1$–$C_6$ alkyl, or $OR^{15}$.

12. A compound of claim 1 of Formula (I):

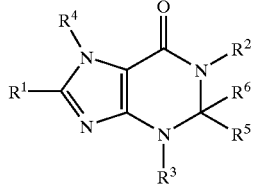

(I)

or a pharmaceutically acceptable salt form thereof, wherein:
$R^1$ is $C_1$–$C_4$ alkyl substituted with 0–3 $X^1$, $C_3$–$C_8$ cycloalkyl substituted with 0–3 $X^1$, $C_2$–$C_4$ alkenyl substituted with 0–3 $X^1$, $C_2$–$C_4$ alkynyl substituted with 0–3 $X^1$, $C_1$–$C_4$ haloalkyl, CN, $OR^{1a}$, or $S(O)_n R^{1a}$;
$R^2$ is $C_1$–$C_6$ alkyl substituted with 0 to 4 $X^3$, $C_3$–$C_7$ cycloalkyl substituted with 0 to 4 $X^3$, $C_3$–$C_6$-alkenyl substituted with 0 to 4 $X^3$, or $C_3$–$C_6$-alkynyl substituted with 0 to 4 $X^3$;
each $X^3$ is, independently at each occurrence, halogen, OH, $C_2$–$C_4$ alkenyl, $C_2$–$C_4$ alkynyl, $C_2$–$C_4$ cycloalkyl, $C_1$–$C_4$ haloalkyl, $CO_2R^7$ $OC(O)R^7$, $COR^7$, $OC(O)OR^7$, $CO_2H$, $OR^7$, $NR^8R^9$, $NR^7COR^9$, $NHR^7SO_2R^9$, $OC(O)NR^7R^8$, $N(COR^7)_2$, $NR^7CONR^8R^9$, $NR^7CO_2R^9$, $CONR^7R^9$, $S(O)_n R^7$, $SO_2NR^7R^9$, SN, or CN;
$R^3$ is phenyl substituted with 0–5 $X^{Ar}$ or pyridyl substituted with 0–4 $X^{hAr}$;
$R^4$ is $C_1$–$C_{10}$ alkyl substituted with 0–1 $X^4$ or 0–3 $X^5$, $C_2$–$C_{10}$ alkenyl substituted with 0–1 $X^4$ or 0–3 $X^5$, $C_2$–$C_{10}$ alkynyl substituted with 0–1 $X^4$ or 0–3 $X^5$, $C_3$–$C_8$ cycloalkyl substituted with 0–1 $X^4$ or 0–3 $X^5$, or aryl-$C_1$–$C_4$ alkyl substituted with 0–1 $X^4$ or 0–3 $X^5$;
each $X^4$ is, independently at each occurrence, CN, $S(O)_n R^{11}$, $CO_2R^{12}$, or 1-naphthalenyl;
each $X^5$ is, independently at each occurrence, aryl, $C_1$–$C_6$ alkyl, $C_2$–$C_8$ alkenyl, $C_1$–$C_4$ haloalkyl, $OR^{12}$, $NR^{12}R^{14}$, $C_1$–$C_4$ alkoxy-$C_{1-4}$ alkyl substituted with 0–1 $R^{10}$, or $C_3$–$C_8$ cycloalkyl optionally substituted with 0–1 $R^{10}$, and wherein 0–1 carbon atoms in said $C_3$–$C_8$ cycloalkyl is replaced by —O—; and
each $R^5$ and $R^6$ is, independently, H or $C_1$–$C_4$ alkyl.

13. A compound of claim 1 of Formula (I):

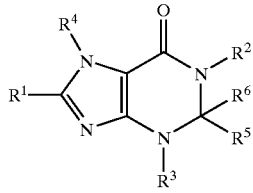

(I)

or a pharmaceutically acceptable salt form thereof, wherein:
$R^1$ is $C_1$–$C_4$ alkyl, CN, $C_1$–$C_4$ haloalkyl, or $OR^{1a}$;
$R^{1a}$ is $C_1$–$C_4$ alkyl substituted with 0–3 halo;
$R^2$ is $C_1$–$C_6$ alkyl substituted with 0 to 4 $X^3$ or $C_3$–$C_7$ cycloalkyl substituted with 0 to 4 $X^3$;
$R^3$ is phenyl substituted with 0–5 $X^{Ar}$ or pyridyl substituted with 0–4 $X^{hAr}$;
$R^4$ is $C_1$–$C_{10}$ alkyl substituted with 0–1 $X^4$ or 0–3 $X^5$, $C_2$–$C_{10}$ alkenyl substituted with 0–1 $X^4$ or 0–3 $X^5$; $C_2$–$C_{10}$ alkynyl substituted with 0–1 $X^4$ or 0–3 $X^5$; $C_3$–$C_8$ cycloalkyl substituted with 0–1 $X^4$ or 0–3 $X^5$, or aryl-$C_1$–$C_4$ alkyl substituted with 0–1 $X^4$ or 0–3 $X^5$; and each $R^5$ and $R^6$ is, independently, H or $C_1$–$C_4$ alkyl.

14. A compound according to claim 13 wherein $R^3$ is phenyl substituted with 0–3 $X^{Ar}$ or pyridyl substituted with 0–2 $X^{hAr}$.

15. A compound according to claim 13 wherein $X^{Ar}$ is selected from phenyl, $C_1$–$C_6$ alkyl, $OR^{15}$, Br, Cl, F, I, or $C_1$–$C_4$ haloalkyl.

16. A compound according to claim 13 wherein $X^{Ar}$ is selected from methyl, ethyl, propyl, methoxy, ethoxy, F, Cl, Br, $CF_3$, or $OCF_3$.

17. A compound according to claim 13 wherein $X^{hAr}$ is selected from $C_1$–$C_6$ alkyl, $C_3$–$C_6$ cycloalkyl, Br, Cl, F, I, $C_1$–$C_4$ haloalkyl, CN, or $OR^{15}$.

18. A compound according to claim 13 wherein $X^{hAr}$ is selected from methyl, ethyl, propyl, methoxy, ethoxy, F, Cl, Br, $CF_3$, or $OCF_3$.

19. A compound according to claim 13 wherein $R^4$ is substituted by 0–1 $X^4$ and $X^4$ is 1-naphthalenyl.

20. A compound of claim 1 of Formula (I):

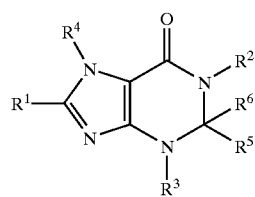

(I)

or a pharmaceutically acceptable salt form thereof, wherein:
$R^1$ is methyl, ethyl, methoxy, ethoxy, $CF_3$, or CN;
$R^2$ is methyl, ethyl, propyl, butyl, pentyl, cyclopropyl, cyclobutyl, cyclopentyl, cyclohexyl, or cycloheptyl;
$R^3$ is phenyl substituted with 0–4 $X^{Ar}$ or pyridyl substituted with 0-3 $X^{hAr}$;
each $X^{Ar}$ is, independently at each occurrence, methyl, ethyl, propyl, butyl, methoxy, ethoxy, $CF_3$, $OCF_3$, CN, Br, Cl, F, or I;
each $X^{hAr}$ is, independently at each occurrence, methyl, ethyl, propyl, butyl, methoxy, ethoxy, $CF_3$, $OCF_3$, CN, Br, Cl, F, or I;
$R^4$ is methyl, ethyl, propyl, butyl, pentyl, hexyl, heptyl, cyclopropyl, cyclobutyl, cyclopentyl, cyclohexyl, cycloheptyl, ethenyl, propenyl, butenyl, or benzyl, wherein $R^4$ is optionally substituted with one 1-naphthalenyl group;
alternatively, $R^4$ is substituted with 0–3 substituents independently selected from phenyl, methyl, ethyl, propyl, butyl, pentyl, hexyl, cyclopropyl, cyclobutyl, cyclopentyl, cyclohexyl, cycloheptyl, ethenyl, propenyl, methoxy, ethoxy, propoxy, butoxy, benzyloxy; and
each $R^5$ and $R^6$ is, independently, H, methyl, or ethyl.

21. A compound of claim 20 wherein $R^1$ is ethyl.
22. A compound of claim 20 wherein $R^1$ is methoxy.
23. A compound of claim 20 wherein $R^2$ is methyl.
24. A compound of claim 1 selected from:
3-(2,4-dichlorophenyl)-8-ethyl-1-methyl-7-(3-pentyl)-1,2,3,7-tetrahydro-6H-purin-6-one;
3-(2,4-dichlorophenyl)-8-ethyl-7-(4-heptyl)-1-methyl-1,2,3,7-tetrahydro-6H-purin-6-one;
3-(2,4-dichlorophenyl)-1,2-dimethyl-8-ethyl-7-(3-pentyl)-1,2,3, 7-tetrahydro-6H-purin-6-one;
3-(2,4-dichlorophenyl)-2,8-diethyl-1-methyl-7-(3-pentyl)-1,2,3,7-tetrahydro-6H-purin-6-one;

3-(2,4-dichlorophenyl)-1,2-dimethyl-8-ethyl-7-(4-heptyl)-1,2,3,7-tetrahydro-6H-purin-6-one;

3-(2,4-dichlorophenyl)-2,8-diethyl-7-(4-heptyl)-1-methyl-1,2,3,7-tetrahydro-6H-purin-6-one;

7-[benzyloxymethyl]-3-(2,4-dichlorophenyl)-8-ethyl-1-methyl-1,2,3,7-tetrahydro-6H-purin-6-one;

3-(2,4-dichlorophenyl)-8-ethyl-7-[1-(methoxymethyl)butyl]-1-methyl-1,2,3,7-tetrahydro-6H-purin-6-one;

3-(2,4-dichlorophenyl)-8-ethyl-1-methyl-7-[1-(2-propenyl)-3-butenyl]-1,2,3,7-tetrahydro-6H-purin-6-one;

3-(2,4-dichlorophenyl)-1-methyl-7-(3-pentyl)-1,2,3,7-tetrahydro-6H-purin-6-one;

3-(2,4-dichlorophenyl)-7-(4-heptyl)-1-methyl-1,2,3,7-tetrahydro-6H-purin-6-one;

3-(2,4-dichlorophenyl)-8-ethyl-7-[(4-methoxyphenyl)methyl]-1-methyl-1,2,3,7-tetrahydro-6H-purin-6-one;

3-(2,4-dichlorophenyl)-7-dicyclopropylmethyl-8-ethyl-1-methyl-1,2,3,7-tetrahydro-6H-purin-6-one;

3-(2,4-dichlorophenyl)-8-ethyl-1-methyl-7-(2-pentyl)-1,2,3,7-tetrahydro-6H-purin-6-one;

3-(2,4-dichlorophenyl)-8-ethyl-1-methyl-7-[(2-methylphenyl)methyl]-1,2,3,7-tetrahydro-6H-purin-6-one;

3-(2,4-dichlorophenyl)-8-ethyl-1-methyl-7-(1-naphthalenylmethyl)-1,2,3,7-tetrahydro-6H-purin-6-one;

3-(2,4-dichlorophenyl)-8-ethyl-7-[3-methoxy-1-(2-methoxyethyl)propyl]-1-methyl-1,2,3,7-tetrahydro-6H-purin-6-one;

7-(1-cyclopropylethyl)-3-(2,4-dichlorophenyl)-8-ethyl-1-methyl-1,2,3,7-tetrahydro-6H-purin-6-one;

7-(1-cyclopropylpropyl)-3-(2,4-dichlorophenyl)-8-ethyl-1-methyl-1,2,3,7-tetrahydro-6H-purin-6-one;

7-(1-cyclopropylbutyl)-3-(2,4-dichlorophenyl)-8-ethyl-1-methyl-1,2,3,7-tetrahydro-6H-purin-6-one;

7-([1,1'-biphenyl]-4-ylmethyl)-3-(2,4-dichlorophenyl)-8-ethyl-1methyl-1,2,3,7-tetrahydro-6H-purin-6-one;

3-(2,4-dichlorophenyl)-8-ethyl-7-(3-heptyl)-1-methyl-1,2,3,7-tetrahydro-6H-purin-6-one;

3-(2-chloro-4-methoxyphenyl)-8-ethyl-1-methyl-7-(3-pentyl)-1,2,3,7-tetrahydro-6H-purin-6-one;

3-(2-chloro-4-methoxyphenyl)-8-ethyl-7-(4-heptyl)-1-methyl-1,2,3,7-tetrahydro-6H-purin-6-one;

3-(2-chloro-4-methoxyphenyl)-8-ethyl-1-methyl-7-(2-pentyl)-1,2,3,7-tetrahydro-6H-purin-6-one;

3-(2-chloro-4-methoxyphenyl)-8-ethyl-7-[1-(methoxymethyl)butyl]-1-methyl-1,2,3,7-tetrahydro-6H-purin-6-one;

3-(2-chloro-4-methoxyphenyl)-7-(1-cyclopropylpropyl)-8-ethyl-1-methyl-1,2,3,7-tetrahydro-6H-purin-6-one;

7-([1,1'-biphenyl]-4-ylmethyl)-3-(2-chloro-4-methoxyphenyl)-8-ethyl-1-methyl-1,2,3,7-tetrahydro-6H-purin-6-one;

3-(2-chloro-4-methoxyphenyl)-8-ethyl-1-methyl-7-[(2-methylphenyl)methyl]-1,2,3,7-tetrahydro-6H-purin-6-one;

3-(2-chloro-4-methoxyphenyl)-7-(1-cyclopropylbutyl)-8-ethyl-1-methyl-1,2,3,7-tetrahydro-6H-purin-6-one;

3-(2-chloro-4-methoxyphenyl)-7-(1-cyclobutylethyl)-8-ethyl-1-methyl-1,2,3,7-tetrahydro-6H-purin-6-one;

3-[2-chloro-4-isopropylphenyl]-8-ethyl-7-(4-heptyl)-1-methyl-1,2,3,7-tetrahydro-6H-purin-6-one;

3-[2-chloro-4-isopropylphenyl]-8-ethyl-7-(1-ethyl-2-methylpropyl)-1-methyl-1,2,3,7-tetrahydro-6H-purin-6-one;

8-ethyl-7-(4-heptyl)-1-methyl-3-(2,4,6-trimethylphenyl)-1,2,3,7-tetrahydro-6H-purin-6-one;

8-ethyl-7-(1-ethyl-2-methylpropyl)-1-methyl-3-(2,4,6-trimethylphenyl)-1,2,3,7-tetrahydro-6H-purin-6-one; and 8-ethyl-7-(4-heptyl)-3-(4-methoxy-2-methylpyrid-3-yl)-1-methyl-1,2,3,7-tetrahydro-6H-purin-6-one, 3-(2-chloro-4-methoxyphenyl)-8-ethyl-7-(3-heptyl)-1-methyl-1,2,3,7-tetrahydro-6purin-6-one;

3-[2-chloro-4-isopropylphenyl]-8-ethyl-7-(3-heptyl)-1-methyl-1,2,3,7-tetrahydro-6H-purin-6-one;

8-ethyl-7-(3-heptyl)-3-(4-methoxy-2-methylpyrid-3-yl)-1-methyl-1,2,3,7-tetrahydro-6H-purin-6-one;

8-ethyl-7-(3-heptyl)-1-methyl-3-(2,4,6-trimethylphenyl)-1,2,3,7-tetrahydro-6H-purin-6-one;

3-(2-chloro-5-fluoro-4-methoxyphenyl)-8-ethyl-7-(4-heptyl)-1-methyl-1,2,3,7-tetrahydro-6H-purin-6-one;

3-(2-chloro-5-fluoro-4-methoxyphenyl)-8-ethyl-7-(3-heptyl)-1-methyl-1,2,3,7-tetrahydro-6H-purin-6-one;

8-ethyl-3-(5-fluoro-4-methoxy-2-methylphenyl)-7-(4-heptyl)-1-methyl-1,2,3,7-tetrahydro-6H-purin-6-one;

8-ethyl-3-(5-fluoro-4-methoxy-2-methylphenyl)-7-(3-heptyl)-1-methyl-1,2,3,7-tetrahydro-6H-purin-6-one;

3-(2-chloro-4,5-dimethoxyphenyl)-8-ethyl-7-(4-heptyl)-1-methyl-1,2,3,7-tetrahydro-6H-purin-6-one;

3-(2-chloro-4,5-dimethoxyphenyl)-8-ethyl-7-(3-heptyl)-1-methyl-1,2,3,7-tetrahydro-6H-purin-6-one;

3-(2,4-dimethoxyphenyl)-8-ethyl-7-(4-heptyl)-1-methyl-1,2,3,7-tetrahydro-6H-purin-6-one;

3-(2,4-dimethoxyphenyl)-8-ethyl-7-(4-heptyl)-1-methyl-1,2,3,7-tetrahydro-6H-purin-6-one; and 3-(2,4-dimethylpyrid-3-yl)-8-ethyl-7-(4-heptyl)-1-methyl-1,2,3,7-tetrahydro-6H-purin-6-one.

25. A pharmaceutical composition comprising a compound of claim 1 and a pharmaceutically acceptable carrier.

26. A method of treating a mammal having a disorder selected from the group consisting of affective disorder, anxiety and depression, comprising administering to said mammal a therapeutically effective amount of a compound of claim 1.

27. A method for antagonizing CRF receptors in a mammal comprising administering to said mammal a therapeutically effective amount of a compound of claim 1.

* * * * *